United States Patent
Francesco et al.

(10) Patent No.: US 6,765,009 B2
(45) Date of Patent: Jul. 20, 2004

(54) 1,4-DISUBSTITUTED BENZO-FUSED COMPOUNDS

(75) Inventors: Pier Francesco, Woodbury, CT (US); Daniel R. Goldberg, Redding, CT (US); Abdelhakim Hammach, Danbury, CT (US); Neil Moss, Ridgefield, CT (US); Kristen Mueller, St. Paul, MN (US); John Robinson Regan, Larchmont, NY (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 20 days.

(21) Appl. No.: 10/120,028

(22) Filed: Apr. 10, 2002

(65) Prior Publication Data

US 2003/0083333 A1 May 1, 2003

Related U.S. Application Data

(60) Provisional application No. 60/283,642, filed on Apr. 13, 2001.

(51) Int. Cl.[7] .................. C07D 239/34; C07D 295/192; A61K 31/505; A61K 31/5375; A61P 19/02
(52) U.S. Cl. ........................ 514/272; 544/312; 544/321; 544/332; 544/319; 544/317; 544/165; 544/300; 514/273; 514/274; 514/275; 564/49; 564/50
(58) Field of Search ................................. 544/312, 321, 544/332, 319, 317; 514/272, 273, 274, 275

(56) References Cited

FOREIGN PATENT DOCUMENTS

WO    WO 00 41698 A1    7/2000

OTHER PUBLICATIONS

Chalmers (TiPS vol. 17, pp. 166–172 Apr. 1996).*
DeLaGarza VW., Am Fam Physician, Oct. 1, 2003, vol. 68, No. 7, pp. 1365–1372.*

Gruol, D.L., et al; Physiological and Pathological Roles of Interleukin–6 in the Central Nervous System, Molecular Neurobiology, vol. 15, 1997, pp 307–339.

Holden, R.J., et al; Interleukin 1,β: A Common Cause of Alzheimer's Disease and Diabetes Mellitus; Medical Hypotheses (1995) 45, pp. 559–571.

Facts: About Nonsteroidal Anti–Inflammatory Drugs—Fact Sheet provided by the Alzheimer's Association 06/03.

Harada, A; et al; Interleukin 8 as a novel target for intervention therapy in acute inflammatory diseases; Molecular Medicine Today, Nov. 1996 pp 482–489.

Kostulas, N. et al Ischemic Stroke is Associated with a Systemic Increase of Blood Mononuclear Cells Expressing Interleukin–8 mRNA, Division of Neurology, Karolinska Institute, Huddinge University Hospital.

Hawley's Condensed Chemical Dictionary Thirteenth Edition revised by Richard J. Lewis Sr., p. 21.

\* cited by examiner

*Primary Examiner*—Mark L. Berch
*Assistant Examiner*—Kahsay Habte
(74) *Attorney, Agent, or Firm*—Robert P. Raymond; Anthony P. Bottino; Timothy X. Witkowski

(57) ABSTRACT

Disclosed are novel 1,4-disubstituted benzo-fused compounds wherein G, X, L, Q, n and Y are defined herein. The compounds are useful in pharmaceutic compositions for treating diseases or pathological conditions involving inflammation such as chronic inflammatory diseases. Also disclosed are processes of making such compounds.

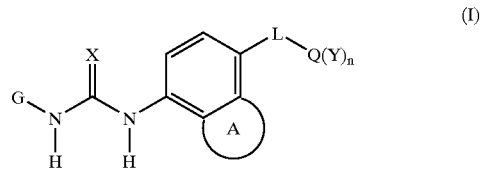

(I)

24 Claims, No Drawings

1,4-DISUBSTITUTED BENZO-FUSED COMPOUNDS

RELATED APPLICATION DATA

This application claims benefit to U.S. provisional application No. 60/283,642 filed Apr. 13, 2001.

TECHNICAL FIELD OF THE INVENTION

This invention relates to novel 1,4-disubstituted benzo-fused compounds of formula(I):

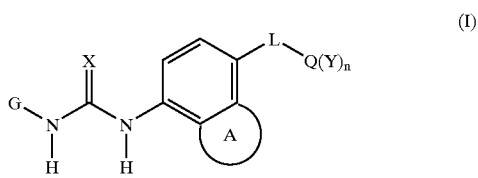

wherein A, G, X, L, Q and Y of formula(I) are defined below. The compounds of the invention inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

BACKGROUND OF THE INVENTION

Tumor necrosis factor (TNF) and interleukin-1(IL-1) are important biological entities collectively referred to as proinflammatory cytokines. These, along with several other related molecules, mediate the inflammatory response associated with the immunological recognition of infectious agents. The inflammatory response plays an important role in limiting and controlling pathogenic infections. Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28–38). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24–5, 1997). These include the treatment of rheumatoid arthritis, Crohn's disease and ulcerative colitis (Rankin, E. C. C., et al., 1997, *British J. Rheum.* 35: 334–342 and Stack, W. A., et al., 1997, *Lancet* 349: 521–524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TNFα receptor, Ro 45–2081 (Hoffman-LaRoche Inc., Nutley, N.J.) has demonstrated efficacy in various animal models of allergic lung inflammation and acute lung injury. Ro 45–2081 is a recombinant chimeric molecule constructed from the soluble 55 kDa human TNF receptor fused to the hinge region of the heavy chain IgG1 gene and expressed in eukaryotic cells (Renzetti, et al, 1997, *Inflamm. Res.* 46: S143). IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrution* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc Soc Exp Biol Med.* 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A*, 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med Hypotheses,* 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol.* 109, 54). IL-1 and TNF are both involved in periodontal disease. The destructive process associated with periodontal disease may be due to a disregulation of both IL-1 and TNF (Howells, 1995, *Oral Dis.* 1, 266).

Proinflammatory cytokines such as TNFα and IL-1β are also important mediators of septic shock and associated cardiopulmonary dysfunction, acute respiratory distress syndrome (ARDS) and multiple organ failure. In a study of patients presenting at a hospital with sepsis, a correlation was found between TNFα and IL-6 levels and septic complications (Terregino et al., 2000, *Ann. Emerg. Med.*, 35, 26). TNFα has also been implicated in cachexia and muscle degradation, associated with HIV infection (Lahdiverta et al., 1988, *Amer. J. Med.*, 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation*, 97, 242).

TNFα levels are elevated in airways of patients with chronic obstructive pulmonary disease and it may contribute to the pathogenesis of this disease (M. A. Higham et al., 2000, *Eur. Respiratory J.*, 15, 281). Circulating TNFα may also contribute to weight loss associated with this disease (N. Takabatake et al., 2000, *Amer. J. Resp. & Crit. Care Med.*,161 (4 Pt 1), 1179). Elevated TNFα levels have also been found to be associated with congestive heart failure and the level has been correlated with severity of the disease (A. M. Feldman et al., 2000, *J. Amer. College of Cardiology*, 35, 537). In addition, TNFα has been implicated in reperfusion injury in lung (Borjesson et al., 2000, *Amer. J. Physiol.*, 278, L3–12), kidney (Lemay et al., 2000, *Transplantation*, 69, 959), and the nervous system (Mitsui et al., 1999, *Brain Res.*, 844, 192).

TNFα is also a potent osteoelastogenic agent and is involved in bone resorption and diseases involving bone resorption (Abu-Amer et al., 2000, *J. Biol. Chem.*, 275, 27307). It has also been found highly expressed in chondrocytes of patients with traumatic arthritis (Melchiorri et al, 2000, *Arthritis and Rheumatism*, 41, 2165). TNFα has also been shown to play a key role in the development of glomerulonephritis (Le Hir et al., 1998, *Laboratory Investigation*, 78, 1625).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J. Hypertension*, 9, 867).

IL-1 has also been shown to induce uveitis in rats which could be inhibited with IL-1 blockers. (Xuan et al., 1998, *J. Ocular Pharmacol. and Ther.*, 14, 31). Cytokines including IL-1, TNF and GM-CSF have been shown to stimulate proliferation of acute myelogenous leukemia blasts (Bruserud, 1996, *Leukemia Res.* 20, 65). IL-1 was shown to be essential for the development of both irritant and allergic contact dermatitis.

Epicutaneous sensitization can be prevented by the administration of an anti-IL-1 monoclonal antibody before epicutaneous application of an allergen (Muller, et al., 1996, *Am J Contact Dermat.* 7, 177). Data obtained from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopheresis, granulocyte transfusion associated syndromes, and necrotizing enterocolitis. Rhinovirus triggers the production of various proinflammatory cytokines, predominantly IL-8, which results in symptomatic illnesses such as acute rhinitis (Winther et al., 1998, *Am J Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol Ther.* 1, 107). Several infectious diseases, such as influenza, indicate IL-6 and IFN alpha as key factors in both symptom formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and postmenopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.*, 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including bum-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferon γ (IFN γ) has been implicated in a number of diseases. It has been associated with increased collagen deposition that is a central histopathological feature of graft-versus-host disease (Parkman, 1998, *Curr Opin Hematol.* 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk Lymphoma.* 19, 173). The development of insulin-dependent diabetes (Type 1) can be correlated with the accumulation in pancreatic islet cells of T-cells producing IFN γ (Ablumunits, et al., 1998, *J Autoimmun.* 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFN γ following challenge with Vespula venom (Bonay, et al., 1997, *Clin Exp Immunol.* 109, 342). The expression of a number of cytokines, including IFN γ has been shown to increase following a delayed type hypersensitivity reaction thus indicating a role for IFN γ in atopic dermatitis (Szepietowski, et al., 1997, *Br J Dermatol.* 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med Hyg.* 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998, *Proc Soc Exp Biol Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin Immunopathol.* 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: the rheumatoid arthritis, tumor associated osteolysis and postmenopausal osteoporosis (Evans, et al, 1996, *J Bone Miner Res.* 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon.* 43, 277). IFN γ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther.* 10 *Suppl* 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

WO 01/01986 discloses particular compounds alleged to having the ability to inhibit TNF-alpha. The specific inhibitors disclosed are structurally distinct from the novel compounds disclosed in the present application disclosed hereinbelow. Certain compounds disclosed in WO 01/01986 are indicated to be effective in treating the following diseases: dementia associated with HIV infection, glaucoma, opticneuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalophathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas amd their use in treating cytokine diseases and proteolytic enzyme mediated disease. WO 00/41698 discloses aryl ureas said to be useful in treating p38 MAP kinase diseases.

U.S. Pat. No. 5,162,360 discloses N-substituted aryl-N'-heterocyclic substituted urea compounds which are described as being useful for treating hypercholesterolemia and atroclerosis.

The work cited above supports the principle that inhibition of cytokine production will be beneficial in the treatment of various disease states. Some protein therapeutics are in late development or have been approved for use in particular diseases. Protein therapeutics are costly to produce and have bioavailability and stability problems. Therefore a need exists for new small molecule inhibitors of cytokine production with optimized efficacy, pharmacokinetic and safety profiles.

BRIEF SUMMARY OF THE INVENTION

The work cited above supports the principle that inhibition of cytokine production will be beneficial in the treatment of various disease states.

It is therefore an object of the invention to provide novel compounds which inhibit the release of inflammatory cytokines such as interleukin-1 and tumor necrosis factor.

It is a further object of the invention to provide methods for treating diseases and pathological conditions involving inflammation such as chronic inflammatory disease, using the novel compounds of the invention.

It is yet a further object of the invention to provide processes of preparation of the above-mentioned novel compounds.

DETAILED DESCRIPTION OF THE INVENTION

In the broadest generic aspect of the invention there are provided 1,4-disubstituted benzo-fused compounds compounds of the formula (I):

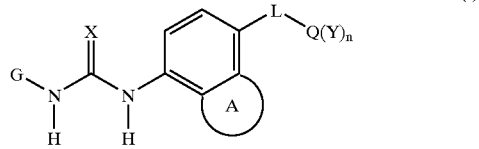

wherein:

ring A is:
fused saturated or unsaturated ring containing 3–5 carbon atoms wherein ring A or the phenyl ring to which it is fused is optionally substituted by one or more a $C_{1-6}$ branched or unbranched alkyl optionally partially or fully halogenated, acetyl, aroyl, $C_{1-6}$ branched or unbranched alkoxy optionally partially or fully halogenated, halogen, methoxycarbonyl, phenylsulfonyl, hydroxy, amino, mono- or di-($C_{1-4}$ alkyl) amino, mono- or di-($C_{1-4}$ alkyl)amino-S(O)$_2$, cyano, nitro or $H_2NSO_2$;

Preferred formula (I) compounds are those where ring A and the phenyl ring to which it is fused form:

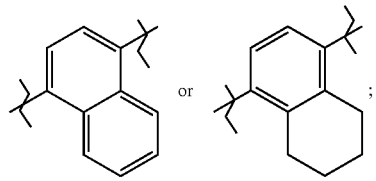

G is:
phenyl, naphthyl, benzocyclobutanyl, dihydronaphthyl, tetrahydronaphthyl, benzocycloheptanyl, benzocycloheptenyl, indanyl, indenyl;
pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzothiazolyl, benzoxazolyl, benzofuranyl, benzothiophenyl, benzopyrazolyl, dihydrobenzofuranyl, dibenzofuranyl, dihydrobenzothiophenyl, benzooxazolonyl, benz[1,4]oxazin-3-onyl, benzodioxolyl, benz[1,3]dioxol-2-onyl, benzofuran-3-onyl, tetrahydrobenzopyranyl, indolyl, 2,3-dihydro-1H-indolyl, indolinyl, indolonyl, indolinonyl, phthalimidyl, chromonyl;
oxetanyl, pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, 3,4-dihydro-2H-benz[1,4]oxazinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl or dithianyl; wherein G is substituted by one $R_3$ and further substituted by one or more $R_1$ or $R_2$;

L is:
a) —O—; —NH—; >C(O); >C(S);
$C_{1-10}$ saturated or unsaturated branched or unbranched carbon chain;
wherein one or more carbon atoms are optionally independently replaced by heteroatoms chosen from O, N and $S(O)_m$; and
wherein said L is optionally substituted with 0–2 oxo groups, one or more $C_{1-4}$ branched or unbranched alkyl optionally substituted by one or more halogen atoms, hydroxy, amino or imino; or
b) >$CR_xR_y$ wherein $R_x$ and $R_y$ are each independently hydrogen, $C_{1-4}$alkyl, heterocycle $C_{0-4}$ alkyl, heteroaryl$C_{0-4}$ alkyl or aryl$C_{0-4}$ alkyl;

Q is:
phenyl, naphthyl, pyridinyl, pyrimidinyl, pyridazinyl, imidazolyl, benzimidazolyl, furanyl, thienyl, pyranyl, thiazolyl, oxazolyl, naphthyridinyl, pyrazinyl, pyrazolyl, triazolyl, tetrazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl, 2-oxa-5-aza-bicyclo[2.2.1]heptanyl, 2-thia-5-aza-bicyclo[2.2.1]heptanyl, imidazo[4,5-b]pyridinyl, 1-oxo-λ4-thiomorpholinyl or 13-oxa-11-aza-tricyclo[7.3.1.0–2,7]trideca-2,4,6-triene which are optionally substituted with one to three $C_{1-6}$ alkyl, phenyl, $C_{1-6}$ alkoxy or hydroxy;
tetrahydropyranyl, 2-oxo-2H-pyranyl, tetrahydrofuranyl, 1,3-dioxolanone, 1,3-dioxanone, 1,4-dioxanyl, morpholinyl, thiomorpholinyl, 8-oxa-3-aza-bicyclo[3.2.1]octanyl, thiomorpholinyl sulfoxide, thiomorpholinyl sulfone, piperazinyl, piperidinyl, piperidinonyl, tetrahydropyrimidonyl, cyclohexanone, cyclohexanol, pentamethylene sulfide, pentamethylene sulfoxide, pentamethylene sulfone, tetramethylene sulfide, tetramethylene sulfoxide or tetramethylene sulfone each optionally substituted with one to three $C_{1-6}$ alkyl, phenyl, $C_{1-6}$ alkoxy or hydroxy; or Q is $C_{1-6}$ alkoxy, secondary or tertiary amine wherein the amino nitrogen is covalently bonded to $C_{1-3}$ alkyl or $C_{1-5}$ alkoxyalkyl, phenylamino, wherein the phenyl ring is optionally substituted with one to two halogen, $C_{1-6}$ alkoxy, hydroxy or mono- or di-($C_{1-3}$ alkyl)amino, $C_{1-6}$ alkyl-$S(O)_m$ or phenyl-$S(O)_m$ wherein the phenyl ring is optionally substituted with one to two halogen, $C_{1-6}$ alkoxy, hydroxy or mono- or di-($C_{1-3}$ alkyl)amino;

$R_1$ is independently:
$C_{3-10}$ branched or unbranched alkyl optionally partially or fully halogenated, and optionally substituted with one to three $C_{3-10}$ cycloalkyl, hydroxy, phenyl, naphthyl , pyridinyl, pyrimidinyl, pyrazinyl, pyridazinyl, pyrrolyl, imidazolyl, pyrazolyl, thienyl, furyl, isoxazolyl or isothiazolyl; each of the aforementioned being optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated and $NH_2C$(O) or mono- or di($C_{1-3}$)alkylaminocarbonyl;

cyclopropyl, cyclobutyl, cyclopentanyl, cyclohexanyl, cycloheptanyl, bicyclopentanyl, bicyclohexanyl or bicycloheptanyl, which are optionally partially or fully halogenated and optionally substituted with one to three $C_{1-3}$ alkyl groups optionally partially or fully halogenated, cyano, hydroxy$C_{1-3}$ alkyl or aryl;

$C_{3-10}$ branched or unbranched alkenyl optionally partially or fully halogenated, and optionally substituted with one to three $C_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl, each of the aforementioned are optionally substituted with 1 to 5 halogen, $C_{1-6}$ branched or unbranched alkyl optionally partially or fully halogenated, cyclopropyl, cyclobutyl, cyclopentanyl, cyclohexanyl, cycloheptanyl, bicyclopentanyl, bicyclohexanyl or bicycloheptanyl, hydroxy, cyano, $C_{1-3}$ alkoxy optionally partially or fully halogenated, $NH_2C(O)$ or mono- or di($C_{1-3}$) alkylaminocarbonyl; cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

N-morpholinyl;

cyano, halogen;

methoxycarbonyl, ethoxycarbonyl or propoxycarbonyl; silyl containing three $C_{1-4}$ independently branched or unbranched alkyl groups optionally partially or fully halogenated;

$C_{1-6}$ branched or unbranched alkyl-C(O), $C_{1-6}$ branched or unbranched-$S(O)_m$;

$C_{2-6}$ alkynyl branched or unbranched carbon chain optionally partially or fully halogenated, wherein one or more methylene groups are optionally replaced by O, NH and $S(O)_m$ and wherein said alkynyl group is optionally independently substituted with 0–2 oxo groups, pyrroldinyl, pyrrolyl, one or more $C_{1-4}$ branched or unbranched alkyl optionally substituted by one or more halogen atoms, nitrile, morpholinyl, piperidinyl, piperazinyl, imidazolyl, phenyl, pyridinyl, tetrazolyl, or $C_{1-4}$ branched or unbranched alkylamino optionally substituted by one or more halogen atoms;

$R_2$ is independently:

a $C_{1-6}$ branched or unbranched alkyl optionally partially or fully halogenated, acetyl, aroyl, $C_{1-4}$ branched or unbranched alkoxy optionally partially or fully halogenated, halogen, methoxycarbonyl or phenylsulfonyl;

hydroxy, amino, or mono- or di-($C_{1-4}$ alkyl)amino, cyano, halogen;

$OR_5$;

nitro; or mono- or di-($C_{1-4}$ alkyl)amino-$S(O)_2$ optionally partially or fully halogenated, or $H_2NSO_2$;

each $R_3$ is independently:

(J)$_p$—L'—$S(O)_m$—NH— or (J)$_p$—L'—O—C(O)—NH—, wherein for $R_3$:

L' is a bond or $C_{1-10}$ saturated or unsaturated branched or unbranched carbon chain;

wherein one or more carbon atoms are optionally independently replaced by heteroatoms chosen from O, N and $S(O)_m$; and wherein said L' is optionally substituted with 0–2 oxo groups, one or more $C_{1-4}$ branched or unbranched alkyl optionally substituted by one or more halogen atoms, hydroxy, amino or imino;

J is:

cyclopropyl, cyclobutyl, cyclopentyl, cyclohexyl, cycloheptyl, bicyclopentanyl, bicyclohexanyl or bicycloheptanyl;

cyclobutenyl, cyclopentenyl, cyclohexenyl, cyclohexadienyl, cycloheptenyl, cycloheptadienyl, bicyclohexenyl or bicycloheptenyl;

phenyl, naphthyl, morpholinyl, pyridinyl, piperidinyl, piperazinyl, pyrimidinyl, pyrazinyl, pyridazinyl, pyrrolyl, pyrrolidinyl, imidazolyl, pyrazolyl, thiazolyl, oxazoyl, [1,3,4]oxadiazol, triazolyl, tetrazolyl, thienyl, furyl, dioxolanyl, tetrahydrofuryl, isoxazolyl, isothiazolyl, quinolinyl, isoquinolinyl, indolyl, benzimidazolyl, benzofuranyl, benzoxazolyl, benzisoxazolyl, benzopyrazolyl, benzothiofuranyl, cinnolinyl, pterindinyl, phthalazinyl, naphthypyridinyl, quinoxalinyl, quinazolinyl, purinyl or indazolyl, a fused aryl selected from benzocyclobutanyl, indanyl, indenyl, dihydronaphthyl, tetrahydronaphthyl, benzocycloheptanyl and benzocycloheptenyl, or J is a fused heteroaryl selected from cyclopentenopyridinyl, cyclohexanopyridinyl, cyclopentanopyrimidinyl, cyclohexanopyrimidinyl, cyclopentanopyrazinyl, cyclohexanopyrazinyl, cyclopentanopyridazinyl, cyclohexanopyridazinyl, cyclopentanoquinolinyl, cyclohexanoquinolinyl, cyclopentanoisoquinolinyl, cyclohexanoisoquinolinyl, cyclopentanoindolyl, cyclohexanoindolyl, cyclopentanobenzimidazolyl, cyclohexanobenzimidazolyl, cyclopentanobenzoxazolyl, cyclohexanobenzoxazolyl, cyclopentanoimidazolyl, cyclohexanoimidazolyl, cyclopentanothienyl and cyclohexanothienyl;

each J is optionally substituted by one to three $R_4$;

each $R_4$ is independently $C_{1-6}$ alkyl, aryl$C_{0-6}$ alkyl, heterocycle$C_{0-6}$ alkyl, heteroaryl$C_{0-6}$ alkyl each optionally substituted by halogen, hydroxy, carboxy, oxo, nitro or nitrile, or $R_4$ is amino optionally mono- or di-substituted by $C_{1-6}$ alkyl, $C_{0-6}$ alkylaryl, $C_{0-6}$ alkylheterocycle or $C_{0-6}$ alkylheteroaryl, halogen, hydroxy, carboxy, oxo, nitro or nitrile; wherein if p is 0, then L' cannot be a bond;

each $R_5$ or $R_6$ is independently:

hydrogen, aryl$C_{0-3}$ alkyl optionally subtituted by halogen, $C_{1-3}$ alkyl or di$C_{1-5}$ alkyl amino, or $R_5$ or $R_6$ are $C_{1-3}$ acyl, aroyl or $C_{1-6}$ branched or unbranched alkyl optionally substituted by $C_{1-5}$ alkoxy, hydroxy, mono- or di-$C_{1-3}$ alkylaminocarbonyl or mono or di$C_{1-3}$ alkyl amino wherein said $C_{1-6}$ alkyl optionally partially or fully halogenated;

or $R_5$ and $R_6$ taken together optionally form a heterocyclic or heteroaryl ring;

Y, which covalently attached to Q, is a bond, —O—, >C(O), —NH—, —C(O)—NH—, —S—, $C_{1-5}$ alkyl branched or unbranched, $C_{1-3}$ alkyl(OH), $C_{2-5}$ alkenyl, $C_{1-3}$ acyl, heterocycle selected from morpholinyl, piperzinyl, piperidinyl, pyrrolidinyl or tetrahydrofuryl, heteroaryl selected from pyridinyl, pyrimidinyl, pyrazinyl, pyridazinyl, pyrrolyl, imidazolyl, pyrazolyl, thienyl, furyl, isoxazolyl, thiazolyl, oxazolyl, triazolyl, tetrazolyl, isothiazolyl, quinolinyl, isoquinolinyl, indolyl, benzimidazolyl, benzofuranyl, benzoxazolyl, benzisoxazolyl, benzopyrazolyl, benzothiofuranyl, quinoxalinyl, quinazolinyl or indazolyl or aryl each alkyl, alkenyl, acyl, heterocycle, heteroaryl and aryl are optionally substituted by one to three hydroxy, oxo, $C_{1-4}$ alkyl, $C_{1-3}$ alkoxy, $C_{1-4}$ acyl, $C_{1-5}$ alkoxycarbonyl, $NR_5R_6$ or $NR_5R_6$—C(O)—;

wherein each Y is optionally further covalently attached to NR$_5$R$_6$, C$_{1-4}$ alkyl, C$_{3-7}$ cycloalkylC$_{0-4}$ alkyl, C$_{1-4}$ alkoxy, aryloxy, hydroxy, arylC$_{0-4}$ alkyl, heteroarylC$_{0-4}$ alkyl or heterocycleC$_{0-4}$ alkyl as wherein the heteroaryl and heterocycle moieties are as hereinabove described for Y and the heterocycle, heteroaryl and aryl moieties are optionally substituted by one to three hydroxy, oxo, C$_{1-3}$ alkyl, C$_{1-3}$ alkoxy, C$_{1-5}$ alkoxycarbonyl, NR$_5$R$_6$ or NR$_5$R$_6$—C(O)—;

m, n and p are each independently 0, 1 or 2;

X is O or S; and the pharmaceutically acceptable derivatives thereof.

In a first subgeneric aspect of the invention there is provided compounds of the formula(I) as described in the broadest generic aspect immediately above, and wherein n is 0;

ring A and the phenyl ring to which it is fused form:

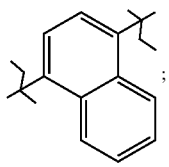

G is phenyl, pyridinyl, pyridonyl, piperidinyl, tetrahydropyranyl, naphthyl, quinolinyl, isoquinolinyl, pyrazinyl, benzimidazolyl, benzoxazolyl, benzooxazolonyl, benzofuranyl, benzothiophenyl, benzopyrazolyl, dihydrobenzofuranyl, dihydrobenzothiophenyl, 3,4-dihydro-2H-benz[1,4]oxazinyl, indanyl, indenyl, indolyl, indolinyl, indolonyl, 2,3-dihydro-1H-indolyl or indolinonyl, wherein G is substituted by one R$_3$ and further substituted by one or more R$_1$ or R$_2$;

L is:
—O—, >C(O), >C(S), —OCH$_2$—, —CH$_2$—, —CH$_2$CH$_2$—, —CH$_2$CH$_2$CH$_2$—, —C(CH$_3$)$_2$—, —CH(OH)—, —CH$_2$CH(OH)—, —CH(OH)CH$_2$—, —OCH$_2$CH$_2$—, —OCH$_2$CH$_2$CH$_2$—, —OCH$_2$CH$_2$(CH$_3$)—, —OCH$_2$(CH$_3$)CH$_2$—, —OCH$_2$C(O)—, —CH=CH—CH$_2$— or —CH=CHCH$_2$CH$_2$, —NH—, —NHCH$_2$—, —NHCH$_2$CH$_2$—, —S(O)$_m$—, —S(O)$_m$CH$_2$—, —S(O)$_m$CH$_2$CH$_2$— and —S(O)$_m$CH$_2$CH$_2$CH$_2$—;

Q is:
pyrimidinyl or morpholinyl each mono- or disubstituted by C$_{1-3}$ alkyl or phenyl, or Q is phenyl, pyridinyl, pyridazinyl, imidazolyl, thiazolyl, oxazolyl, pyrazinyl, pyrazolyl, tetrahydropyranyl, piperazinyl, piperidinyl, triazolyl, 2-oxo-2H-pyran-4-yl, 2-oxa-5-aza-bicyclo[2.2.1]heptanyl, 2-thia-5-aza-bicyclo[2.2.1]heptanyl, 1-oxo-λ4-thiomorpholinyl or 13-oxa-11-aza-tricyclo[7.3.1.0–2,7]trideca-2,4,6-triene;

R$_1$ is independently:
C$_{3-5}$ branched or unbranched alkyl optionally partially or fully halogenated and optionally substituted with one to three C$_{3-6}$ cycloalkyl, hydroxy or phenyl;
N-morpholinyl;
cyclopropyl, cyclobutyl, cyclopentanyl, cyclohexanyl, bicyclopentanyl or bicyclohexanyl optionally partially or fully halogenated and optionally substituted with one to three C$_{1-3}$ alkyl groups optionally partially or fully halogenated, cyano, hydroxyC$_{1-3}$ alkyl or phenyl;

R$_2$ is independently:
a C$_{1-6}$ branched or unbranched alkyl optionally partially or fully halogenated or C$_{1-4}$ branched or unbranched alkoxy optionally partially or fully halogenated R$_3$ is
(J)$_{0-1}$—L'—S(O)$_m$—NH— or (J)$_{0-1}$—L'—O—C(O)—NH—, wherein for R$_3$:
L' is
a bond, C$_{1-5}$ alkyl, hydroxy C$_{1-5}$ alkyl, C$_{2-4}$ alkenyl, amidoC$_{1-5}$ alkyl;

J is:
cyclopropyl, cyclobutyl, cyclopentyl, cyclohexyl, cycloheptyl, bicyclopentanyl, bicyclohexanyl or bicycloheptanyl, phenyl, naphthyl, morpholinyl, piperidinyl, piperazinyl, pyridinyl, pyrimidinyl, pyrazinyl, pyridazinyl, pyrrolyl, pyrrolidinyl, imidazolyl, pyrazolyl, thiazolyl, oxazolyl, thienyl, furyl, dioxolanyl, tetrahydrofuryl, isoxazolyl and isothiazolyl,
cyclobutenyl, cyclopentenyl, cyclohexenyl, cyclohexadienyl, cycloheptenyl, cycloheptadienyl, bicyclohexenyl or bicycloheptenyl;

each of the above J is optionally substituted by one to two R$_4$;

R$_4$ is oxo or mono- or di-C$_{1-3}$ alkylamino;

Y is not present;

m is 2;

and

X is O.

In yet another embodiment of the invention there is provided compounds of the formula(I) as described immediately above, and wherein:

G is
phenyl, pyridinyl, pyridonyl, naphthyl, quinolinyl, isoquinolinyl, pyrazinyl, benzothiophenyl, dihydrobenzofuranyl, dihydrobenzothiophenyl, indanyl, indolyl, indolinyl, indolonyl, indolinonyl, piperidinyl or tetrahydropyranyl, wherein G is substituted by one R$_3$ and further substituted by one to three R$_1$ or R$_2$;

L' is
a bond, C$_{1-5}$ alkyl, hydroxy C$_{1-5}$ alkyl, C$_{2-4}$ alkenyl, amidoC$_{1-5}$ alkyl.

In yet still another embodiment of the invention there is provided compounds of the formula(I) as described immediately above, and wherein G is phenyl, pyridinyl, pyridonyl, naphthyl, quinolinyl, isoquinolinyl, dihydrobenzofuranyl, indanyl, indolinyl, indolonyl or indolinonyl wherein G is substituted by one R$_3$ and further substituted by one to three R$_1$ or R$_2$;

L is:
—O—, >C(O), —C(CH$_3$)$_2$—, —O—CH$_2$—, —CH$_2$—, —OCH$_2$CH$_2$—, —OCH$_2$CH$_2$CH$_2$—, —OCH$_2$CH$_2$(CH$_3$)—, —OCH$_2$(CH$_3$)CH$_2$—, —NH—, —NHCH$_2$—, —NHCH$_2$CH$_2$—, —S(O)$_m$—, —S(O)$_m$CH$_2$—, —S(O)$_m$CH$_2$CH$_2$—, —S(O)$_m$CH$_2$CH$_2$CH$_2$—, —CH$_2$CH$_2$—, —CH$_2$CH$_2$CH$_2$— or —OCH$_2$C(O)—;

each R$_1$ is independently:
C$_{3-5}$ branched or unbranched alkyl optionally partially or fully halogenated and optionally substituted with phenyl or R$_1$ is N-morpholinyl;
cyclopropyl, cyclopentanyl, cyclohexanyl or bicyclopentanyl optionally substituted with one to three methyl groups optionally be partially or fully halogenated, cyano, hydroxymethyl or phenyl;

Q is
morpholinyl or pyrimidinyl each mono- or di-substituted by C$_{1-3}$ alkyl or phenyl, or Q is phenyl, imidazolyl, tetrahydropyranyl, pyridinyl, 2-oxo-2H-pyran-4-yl, 2-oxa-5-aza-bicyclo[2.2.1]heptanyl, 2-thia-5-aza-bicyclo[2.2.1]heptanyl, 1-oxo-λ4-thiomorpholinyl, triazolyl or 13-oxa-11-aza-tricyclo[7.3.1.0–2,7]trideca-2,4,6-triene;

In another embodiment of the invention there is provided of the formula(I) as described immediately above, and wherein G is phenyl substituted by one R$_3$ and further independently substituted by one to two R$_1$ or R$_2$;

and

L is:
—O—, >C(O) or —C(CH₃)₂—;

Q is morpholinyl or pyrimidinyl each mono- or di-substituted by C$_{1-3}$ alkyl or phenyl, or Q is pyridinyl, 2-oxo-2H-pyran-4-yl, 2-oxa-5-aza-bicyclo[2.2.1]heptanyl, 2-thia-5-aza-bicyclo[2.2.1]heptanyl, 1-oxo-λ4-thiomorpholinyl, triazolyl or 13-oxa-11-aza-tricyclo[7.3.1.0–2,7]trideca-2,4,6-triene;

R₃ is
L'—S(O)₂—NH or (J)$_{0-1}$—L'—O—C(O)—NH wherein L' is C$_{1-3}$ alkyl.

In yet another embodiment of the invention there is provided of the formula(I) as described in the fourth embodiment above, and wherein R₁ is
tert-butyl optionally partially or fully halogenated;

R₂ is independently:
C$_{1-3}$ alkyl or C$_{1-3}$ alkoxy;

Q is N-morpholinyl or pyrimidin-4-yl each mono- or di-substituted by methyl or phenyl, or Q is pyridin-4yl, 2-oxo-2H-pyran-4-yl, 2-oxa-5-aza-bicyclo[2.2.1]heptanyl, 2-thia-5-aza-bicyclo[2.2.1]heptanyl, 1-oxo-λ4-thiomorpholine-4-yl, triazol-2-yl or 13-oxa-11-aza-tricyclo[7.3.1.0–2,7]trideca-2,4,6-triene.

In another embodiment of the invention there is provided of the formula(I) as described immediately above, and wherein L is —O—, >C(O) or —C(CH₃)₂—;
and
R₃ is C$_{1-3}$ alkyl-S(O)₂—NH— or C$_{1-3}$ alkyl—O—C(O)—NH—.

In an ultimately preferred embodiment of the invention there is provided of the formula(I) as described immediately above, and wherein
R₃ is CH₃—S(O)₂—NH— or CH₃—O—C(O)—NH—.

The following are representative compounds of the formula (I) where n is 0 which can be made by the methods disclosed herein:

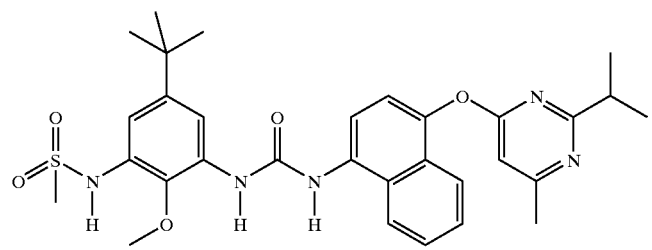

N-(5-tert-Butyl-3-{3-[4-(2-isopropyl-6-methyl-pyrimidin-4-yloxy)-naphthalen-1-yl]-ureido}-2-methoxy-phenyl)-methanesulfonamide;

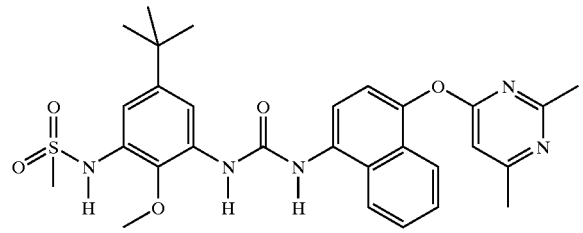

N-(5-tert-Butyl-3-{3-[4-(2,6-dimethyl-pyrimidin-4-yloxy)-naphthalen-1-yl]-ureido}-2-methoxy-phenyl)-methanesulfonamide;

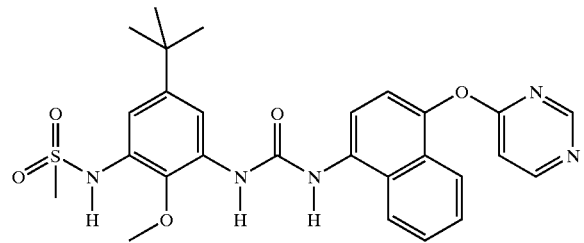

N-(5-tert-Butyl-2-methoxy-3-{3-[4-(pyrimidin-4-yloxy)-naphthalen-1-yl]-ureido}-phenyl)-methanesulfonamide;

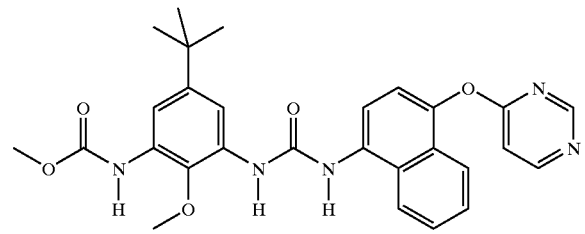

(5-tert-Butyl-2-methoxy-3-{3-[4-(pyrimidin-4-yloxy)-naphthalen-1-yl]-ureido}-phenyl)-carbamic acid methyl ester;

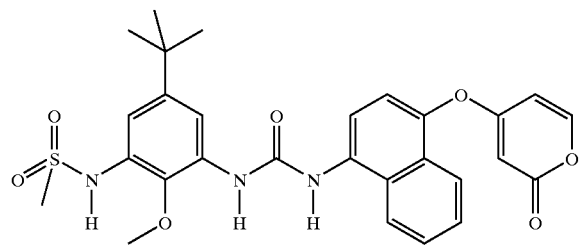

N-(5-tert-Butyl-2-methoxy-3-{3-[4-(2-oxo-2H-pyran-4-yloxy)-naphthalen-1-yl]-ureido}-phenyl)-methanesulfonamide;

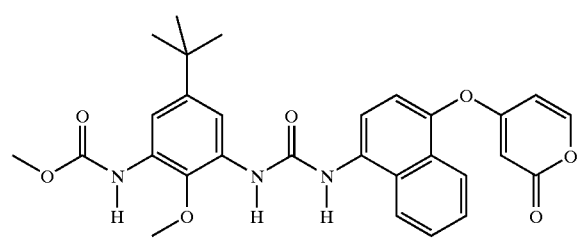

(5-tert-Butyl-2-methoxy-3-{3-[4-(2-oxo-2H-pyran-4-yloxy)-naphthalen-1-yl]-ureido}-phenyl)-carbamic acid methyl ester;

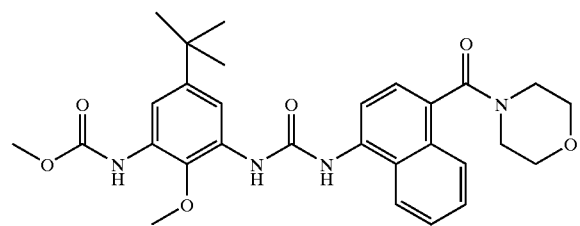

(5-tert-Butyl-2-methoxy-3-{3-[4-(morpholine-4-carbonyl)-naphthalen-1-yl]-ureido}-phenyl)-carbamic acid methyl ester;

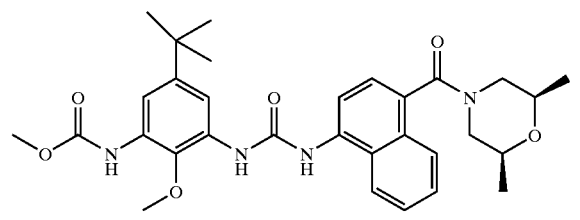

(5-tert-Butyl-3-{3-[4-(cis-2,6-dimethyl-morpholine-4-carbonyl)-naphthalen-1-yl]-ureido}-2-methoxy-phenyl)-carbamic acid methyl ester;

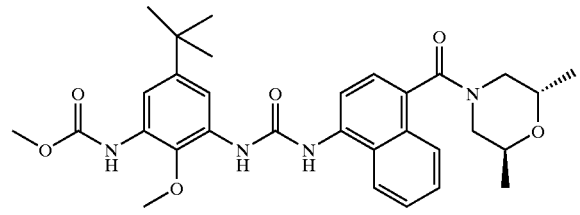

(5-tert-Butyl-3-{3-[4-(trans-2,6-dimethyl-morpholine-4-carbonyl)-naphthalen-1-yl]-ureido}-2-methoxy-phenyl)-carbamic acid methyl ester;

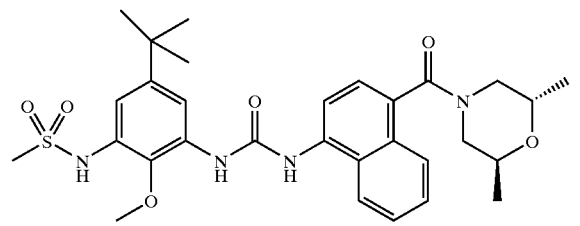

N-(5-tert-Butyl-3-{3-[4-trans-2,6-dimethyl-morpholine-4-carbonyl)-naphthalen-1-yl]-ureido}-2-methoxy-phenyl)-methanesulfonamide;

-continued

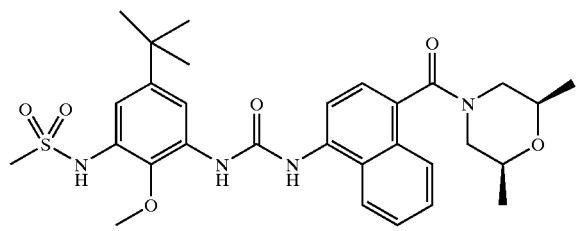

N-(5-tert-Butyl-3-{3-[4-(cis-2,6-dimethyl-morpholine-4-carbonyl)-naphthalen-1-yl]-ureido}-2-methoxy-phenyl)-methanesulfonamide;

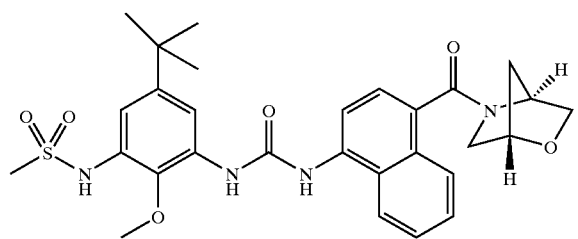

N-(5-tert-Butyl-2-methoxy-3-{3-[4-(2-oxa-5-aza-bicyclo-[2.2.1]heptane-5-carbonyl)-naphthalen-1-yl]-ureido}-phenyl)-methanesulfonamide;

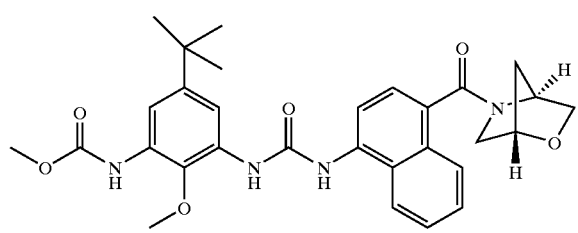

(5-tert-Butyl-2-methoxy-3-{3-[4-(2-oxa-5-aza-bicyclo-[2.2.1]heptane-5-carbonyl)-naphthalen-1-yl]-ureido}-phenyl)-carbamic acid methyl ester;

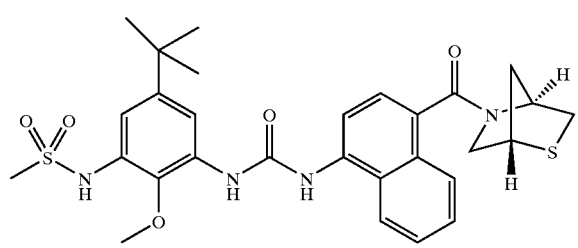

N-(5-tert-Butyl-2-methoxy-3-{3-[4-(2-thia-5-aza-bicyclo-[2.2.1]heptane-5-carbonyl)-naphthalen-1-yl]-ureido}-phenyl)-methanesulfonamide;

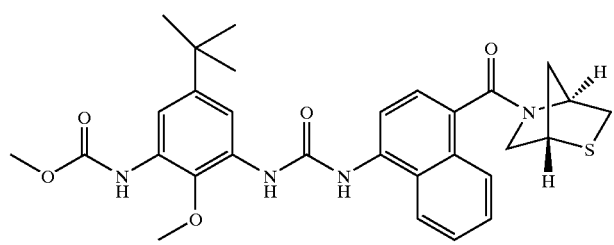

N-(5-tert-Butyl-2-methoxy-3-{3-[4-(2-thia-5-aza-bicyclo-[2.2.1]heptane-5-carbonyl)-naphthalen-1-yl]-ureido}-phenyl)-carbamic acid methyl ester;

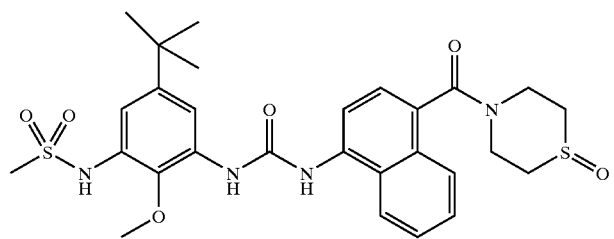

N-(5-tert-Butyl-2-methoxy-3-{3-[4-(1-oxo-λ4-thiomorpholine-4-carbonyl)-naphthalen-1-yl]-ureido}-phenyl)-methanesulfonamide;

-continued

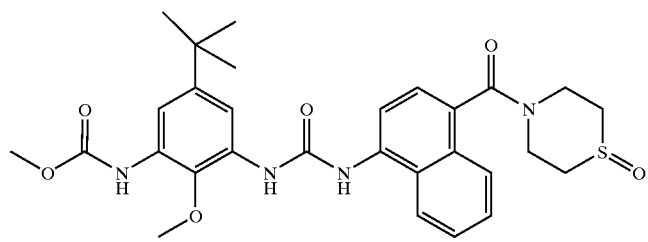

N-(5-tert-Butyl-2-methoxy-3-{3-[4-(1-oxo-λ4-thiomorpholine-4-carbonyl)-naphthalen-1-yl]-ureido}-phenyl)-carbamic acid methyl ester;

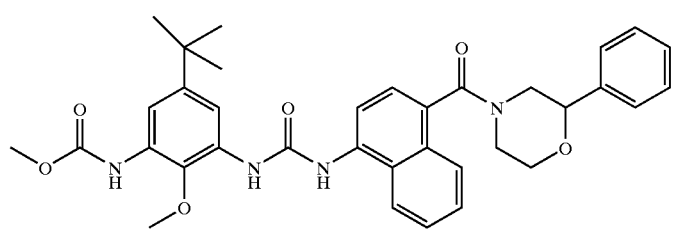

(5-tert-Butyl-2-methoxy-3-{3-[4-(2-phenyl-morpholine-4-carbonyl)-naphthalen-1-yl]-ureido}-phenyl)-carbamic acid methyl ester;

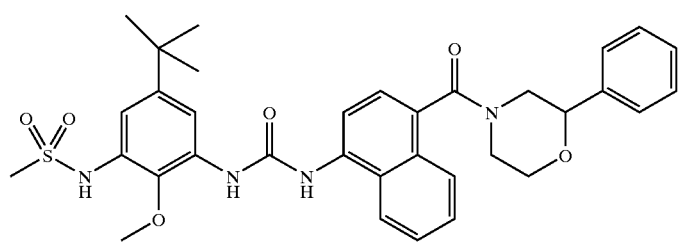

(5-tert-Butyl-2-methoxy-3-{3-[4-(2-phenyl-morpholine-4-carbonyl)-naphthalen-1-yl]-ureido}-phenyl)-methanesulfonamide;

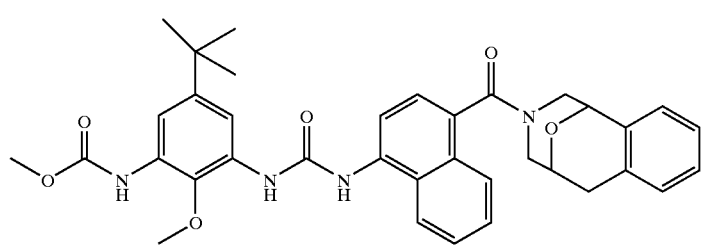

(5-tert-Butyl-2-methoxy-3-{3-[4-(13-oxa-11-aza-tricyclo[7.3.1.0-2,7]trideca-2(7),3,5-triene-11-carbonyl)-naphthalen-1-yl]-ureido}-phenyl)-carbamic acid methyl ester;

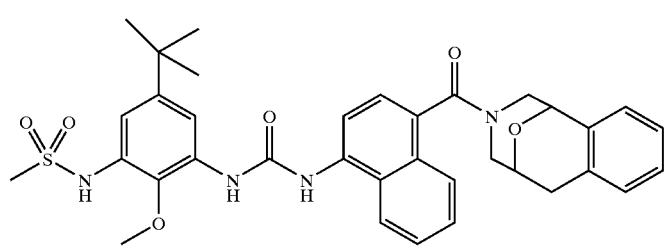

(5-tert-Butyl-2-methoxy-3-{3-[4-(13-oxa-11-aza-tricyclo[7.3.1.0-2,7]trideca-2(7),3,5-triene-11-carbonyl)-naphthalen-1-yl]-ureido}-phenyl)-methanesulfonamide;

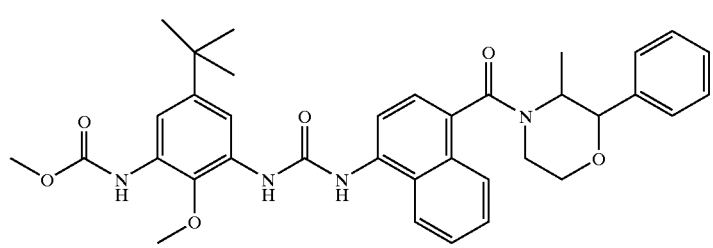

(5-tert-Butyl-2-methoxy-3-{3-[4-(3-methyl-2-phenyl-morpholine-4-carbonyl)-naphthalen-1-yl]-ureido}-phenyl)-carbamic acid methyl ester;

-continued

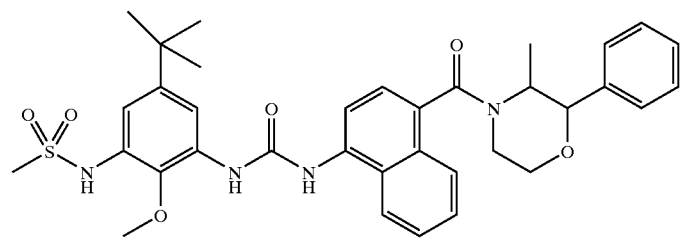

(5-tert-Butyl-2-methoxy-3-{3-[4-(3-methyl-2-phenyl-morpholine-4-carbonyl)-naphthalen-1-yl]-ureido}-phenyl)-methanesulfonamide;

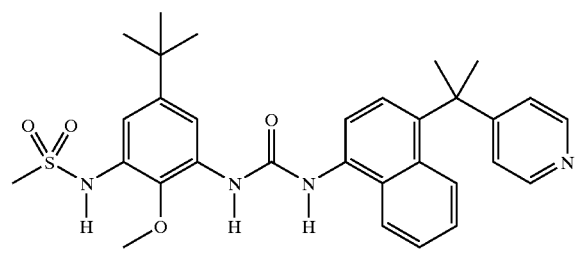

N-(5-tert-Butyl-2-methoxy-3-{3-[4-(1-methyl-1-pyridin-4-yl-ethyl)naphthalen-1-yl]ureido}-phenyl)methanesulfonamide

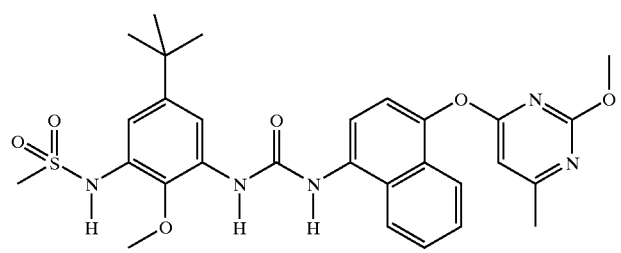

N-(5-tert-Butyl-2-methoxy-3-{3-[4-(2-methoxy-6-methyl-pyrimidin-4-yloxy)-naphthalen-1-yl]-ureido}-phenyl)-methanesulfonamide;

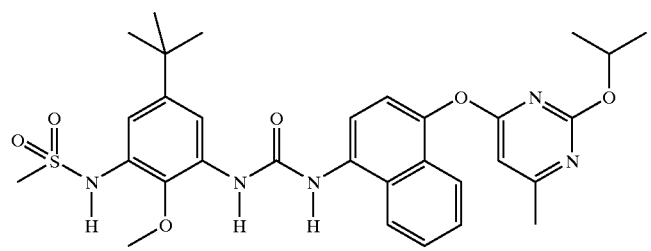

N-(5-tert-Butyl-3-{3-[4-(2-isopropoxy-6-methyl-pyrimidin-4-yloxy)-naphthalen-1-yl]-ureido}-2-methoxy-phenyl)-methanesulfonamide;

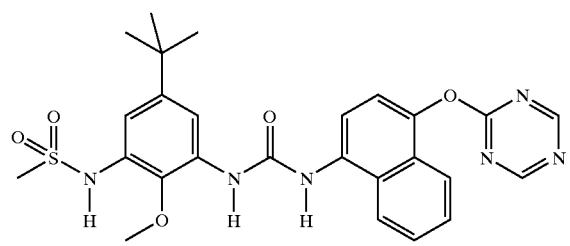

N-(5-tert-Butyl-2-methoxy-3-{3-[4-([1,3,5]triazin-2-yloxy)-naphthalen-1-yl]-ureido}-phenyl)-methanesulfonamide;

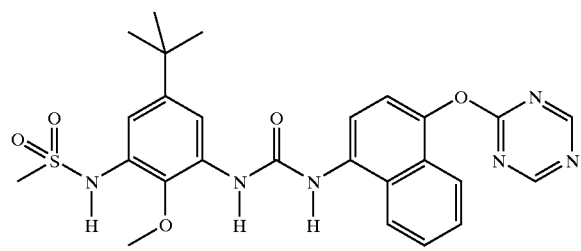

N-(5-tert-Butyl-2-methoxy-3-{3-[4-([1,3,5]triazin-2-yloxy)-naphthalen-1-yl]-ureido}-phenyl)-methanesulfonamide;

-continued

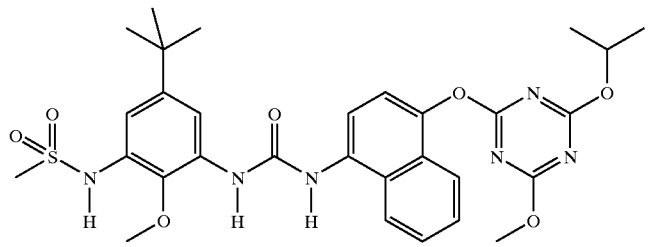

N-(5-tert-Butyl-3-{3-[4-(4-isopropoxy-6-methoxy-[1,3,5]triazin-2-yloxy)-naphthalen-1-yl]-ureido}-2-methoxy-phenyl)-methanesulfonamide and the pharmaceutically acceptable derivatives thereof.

the pharmace acceptable detivatives thereof. In a second subgeneric aspect of the invention there is proveded compounds of the
formula(I) as described in the broadest generic aspect, and wherein
n is 1;
ring A and the phenyl ring to which it is fused form:

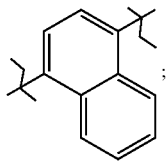

G is
phenyl, pyridinyl, pyridonyl, naphthyl, quinolinyl, isoquinolinyl, pyrazinyl, piperidinyl, tetrahydropyranyl, benzimidazolyl, benzoxazolyl, benzooxazolonyl, benzofuranyl, benzothiophenyl, benzopyrazolyl, dihydrobenzofuranyl, dihydrobenzothiophenyl, 3,4-dihydro-2H-benz[1,4]oxazinyl, indanyl, indenyl, indolyl, indolinyl, indolonyl, 2,3-dihydro-1H-indolyl or indolinonyl, wherein G is substituted by one $R_3$ and further substituted by one or more $R_1$ or $R_2$;
L is:
—O—, —OCH$_2$—, —CH$_2$—, —CH(OH)—, —CH$_2$—CH(OH)—, —CH(OH)CH$_2$—, —OCH$_2$CH$_2$—, O—CH$_2$CH$_2$CH$_2$—, —OCH$_2$CH$_2$(CH$_3$)—, —OCH$_2$(CH$_3$)CH$_2$—, —CH$_2$CH$_2$—, —CH$_2$CH$_2$CH$_2$—, —OCH$_2$C(O)—, —CH=CHCH$_2$— or —CH=CHCH$_2$CH$_2$—, —NH—, —NHCH$_2$—, —NHCH$_2$CH$_2$—, —S(O)$_m$—, —S(O)$_m$CH$_2$—, —S(O)$_m$CH$_2$CH$_2$— and —S(O)$_m$CH$_2$CH$_2$CH$_2$—;
Q is:
phenyl, pyridinyl, pyrimidinyl, pyridazinyl, imidazolyl, tetrahydropyranyl, thiazolyl, oxazolyl, pyrazinyl, pyrazolyl, morpholinyl, thiomorpholinyl, piperazinyl or piperidinyl;
$R_1$ is independently:
$C_{3-5}$ branched or unbranched alkyl optionally partially or fully halogenated, and optionally substituted with one to three $C_{3-6}$ cycloalkyl, hydroxy and phenyl; N-morpholinyl; cyclopropyl, cyclobutyl, cyclopentanyl, cyclohexanyl, bicyclopentanyl or bicyclohexanyl optionally partially or fully halogenated and optionally substituted with one to three $C_{1-3}$ alkyl groups optionally partially or fully halogenated, cyano, hydroxy$C_{1-3}$ alkyl or phenyl;
$R_2$ is independently:
a $C_{1-6}$ branched or unbranched alkyl optionally partially or fully halogenated or $C_{1-4}$ branched or unbranched alkoxy optionally partially or fully halogenated;
$R_3$ is
$(J)_{0-1}$—L'—S(O)$_m$—NH— or $(J)_{0-1}$—L'—O—C(O)—NH—, wherein for $R_3$:
L' is
a bond, $C_{1-5}$ alkyl, hydroxy $C_{1-5}$ alkyl, $C_{2-4}$ alkenyl, amido$C_{1-5}$ alkyl;
J is:
cyclopropyl, cyclobutyl, cyclopentyl, cyclohexyl, cycloheptyl, bicyclopentanyl, bicyclohexanyl or bicycloheptanyl, phenyl, naphthyl, morpholinyl, piperidinyl, piperazinyl, pyridinyl, pyrimidinyl, pyrazinyl, pyridazinyl, pyrrolyl, pyrrolidinyl, imidazolyl, pyrazolyl, thiazolyl, oxazolyl, thienyl, furyl, dioxolanyl, tetrahydrofuryl, isoxazolyl and isothiazolyl,
cyclobutenyl, cyclopentenyl, cyclohexenyl, cyclohexadienyl, cycloheptenyl, cycloheptadienyl, bicyclohexenyl or bicycloheptenyl;
each of the above J is optionally substituted by one to two $R_4$;
$R_4$ is oxo or mono- or di-$C_{1-3}$ alkylamino;
Y is
a bond, —O—, >C(O), —NH—, —C(O)—NH—, —S—, $C_{1-5}$ alkyl branched or unbranched, $C_{2-5}$ alkenyl, $C_{1-3}$ acyl, $C_{1-3}$ alkyl(OH), heterocycle selected from morpholinyl, piperazinyl, piperidinyl, pyrrolidinyl and tetrahydrofuranyl, heteroaryl selected from pyridinyl, pyrimidinyl, pyrazinyl, pyridazinyl, pyrrolyl, imidazolyl, pyrazolyl, thienyl, furyl, isoxazolyl, thiazolyl, oxazolyl and isothiazolyl or aryl each alkyl, alkenyl, acyl, heterocycle, heteroaryl and aryl are optionally substituted by one to three hydroxy, oxo, $C_{1-3}$ alkyl, $C_{1-3}$ alkoxy, $C_{1-5}$ alkoxycarbonyl, $NR_5R_6$ or $NR_5R_6$—C(O)—;
wherein each Y is further covalently attached to $NR_5R_6$, $C_{1-3}$ alkyl, $C_{3-6}$ cycloalkyl$C_{0-2}$alkyl, hydroxy, $C_{1-3}$ alkoxy, phenoxy, phenyl$C_{0-4}$ alkyl, piperazinyl$C_{0-4}$ alkyl, piperidinyl $C_{0-4}$alkyl, pyrrolidinyl$C_{0-4}$ alkyl, morpholinyl$C_{0-4}$ alkyl, tetrahydrofuranyl$C_{0-4}$ alkyl or pyridinyl $C_{0-4}$alkyl, each abovelisted heterocycle, heteroaryl and phenyl is optionally substituted by one to three hydroxy, oxo, $C_{1-4}$ alkyl, $C_{1-3}$ alkoxy, $C_{1-5}$ alkoxycarbonyl, $NR_5R_6$—C(O)— or $C_{1-4}$ acyl, each $R_5$ and $R_6$ are independently hydrogen, phenyl$C_{0-3}$alkyl optionally subtituted by halogen, $C_{1-3}$ alkyl or di$C_{1-5}$ alkyl amino, or $R_5$ and $R_6$ are $C_{1-2}$ acyl, benzoyl or $C_{1-4}$ branched or unbranched alkyl optionally substituted by $C_{1-4}$ alkoxy, hydroxy or mono or di$C_{1-3}$ alkyl amino;
m is 2;
and
X is O.
In yet another embodiment of the invention there is provided compounds of the formula(I) as described immediately above, and wherein:
G is phenyl, pyridinyl, pyridonyl, naphthyl, quinolinyl, isoquinolinyl, pyrazinyl, benzothiophenyl, dihydrobenzofuranyl, dihydrobenzothiophenyl, indanyl, indolyl, indolinyl, indolonyl, indolinonyl, piperidinyl or tetrahydropyranyl, wherein G is substituted by one $R_3$ and further substituted by one to three $R_1$ or $R_2$;

L' is
a bond, $C_{1-5}$ alkyl, hydroxy $C_{1-5}$ alkyl, $C_{2-4}$ alkenyl, amido$C_{1-5}$ alkyl.

In yet still another embodiment of the invention there is provided compounds of the formula(I) as described immediately above, and wherein G is phenyl, pyridinyl, pyridonyl, naphthyl, quinolinyl, isoquinolinyl, dihydrobenzofuranyl, indanyl, indolinyl, indolonyl or indolinonyl, wherein G is substituted by one $R_3$ and further substituted by one to three $R_1$ or $R_2$;

L is:
—O—, —OCH$_2$—, —CH$_2$—, —CH$_2$CH$_2$—, —CH$_2$CH$_2$CH$_2$—, —OCH$_2$CH$_2$—, —OCH$_2$CH$_2$CH$_2$—, —OCH$_2$CH$_2$(CH$_3$)—, —OCH$_2$(CH$_3$)CH$_2$—, —NH—, —NHCH$_2$—, —NHCH$_2$CH$_2$—, —S(O)$_m$—, —S(O)$_m$CH$_2$—, —S(O)$_m$CH$_2$CH$_2$—, —S(O)$_m$CH$_2$CH$_2$CH$_2$— or —OCH$_2$C(O)—;

each $R_1$ is independently:
$C_{3-5}$ branched or unbranched alkyl optionally partially or fully halogenated, and optionally substituted with phenyl;
N-morpholinyl;
cyclopropyl, cyclopentanyl, cyclohexanyl or bicyclopentanyl optionally substituted with one to three methyl groups optionally partially or fully halogenated, cyano, hydroxymethyl or phenyl;

Q is
phenyl, pyridinyl, pyrimidinyl, imidazolyl, tetrahydropyranyl or morpholinyl;

Y is
a bond, —O—, —S—, >C(O), —NH—, —C(O)—NH—, —CH(C$_{1-2}$ alkyl)-;
or Y is $C_{1-2}$ alkyl, $C_{1-2}$ alkyl(OH), $C_{2-4}$ alkenyl, $C_{1-2}$ acyl, imidazolyl, pyrazolyl, pyrrolidinyl, thienyl, isoxazolyl, thiazolyl, oxazolyl, isothiazolyl or phenyl each optionally substituted by one to two hydroxy, oxo, $C_{1-3}$ alkyl, $C_{1-3}$ alkoxy, $C_{1-5}$ alkoxycarbonyl, NR$_5$R$_6$ or NR$_5$R$_6$—C(O)—;
wherein each Y is further covalently attached to NR$_5$R$_6$, $C_{1-3}$ alkyl, $C_{3-6}$ cycloalkylC$_{0-2}$alkyl, hydroxy, $C_{1-3}$ alkoxy, phenoxy, phenylC$_{0-4}$ alkyl, piperazinylC$_{0-4}$ alkyl, piperidinylC$_{0-4}$ alkyl, pyrrolidinylC$_{0-4}$ alkyl, morpholinylC$_{0-4}$ alkyl, tetrahydrofuranylC$_{0-4}$ alkyl or pyridinylC$_{0-4}$ alkyl each abovelisted heterocycle, heteroaryl or phenyl is optionally substituted by one to two $C_{1-5}$ alkoxycarbonyl, NR$_5$R$_6$—C(O)—, $C_{1-4}$ alkyl, $C_{1-4}$ acyl or hydroxy;
each $R_5$ and $R_6$ are independently hydrogen, phenylC$_{0-3}$ alkyl optionally subtituted by halogen or $C_{1-3}$ alkyl, acetyl, benzoyl or $C_{1-4}$ branched or unbranched alkyl optionally substituted by $C_{1-3}$ alkoxy, hydroxy, mono or diC$_{1-3}$ alkyl amino.

In another embodiment of the invention there is provided of the formula(I) as described immediately above, and wherein G is phenyl substituted by one $R_3$ and further independently substituted by one to two $R_1$ or $R_2$;
and
L is:
—O—, —NH—, —CH$_2$— or —S(O)$_m$—;
Q is pyridinyl or phenyl;
$R_3$ is
(J)$_{0-1}$—L'—S(O)$_2$—NH or (J)$_{0-1}$—L'—O—C(O)—NH
wherein
L' is $C_{1-5}$alkyl;
wherein J is cyclobutenyl, N-morpholinyl, N-piperidinyl, N-piperazinyl or N-pyrrolidinyl, each J is optionally substituted by one to two $R_4$;

In yet another embodiment of the invention there is provided of the formula(I) as described in the fourth embodiment above, and wherein L is:
—O— or —CH$_2$—;
$R_1$ is
tert-butyl optionally partially or fully halogenated;
$R_2$ is independently:
$C_{1-3}$ alkyl or $C_{1-3}$ alkoxy;
Q is pyridinyl attached to L at the pyridin-4yl position or phenyl which has Y attached at the meta position;
Y is
a bond, —O—, —S—, >C(O), —CH(CH$_3$)—, —CH(OH)—, —NH—, —C(O)—NH—;
or Y is —CH$_2$—, —CH=CHCH$_2$—, imidazolyl, thiazolyl, pyrrolidinyl, oxazolyl or phenyl each optionally substituted by one hydroxy, oxo, $C_{1-3}$ alkyl, $C_{1-3}$ alkoxy, $C_{1-5}$ alkoxycarbonyl, NR$_5$R$_6$ or NR$_5$R$_6$—C(O)—;
wherein each Y is further covalently attached to NR$_5$R$_6$, $C_{1-3}$ alkyl, $C_{3-6}$ cycloalkylC$_{0-2}$alkyl, $C_{1-3}$ alkoxy, phenoxy, hydroxy, phenylC$_{0-4}$ alkyl, piperazinylC$_{0-4}$ alkyl, piperidinylC$_{0-4}$ alkyl, pyrrolidinylC$_{0-4}$ alkyl, morpholinylC$_{0-4}$ alkyl, tetrahydrofuranylC$_{0-4}$ alkyl or pyridinylC$_{0-4}$ alkyl, each abovelisted heterocycle, heteroaryl or phenyl is optionally substituted by one to two $C_{1-5}$ alkoxycarbonyl, NR$_5$R$_6$—C(O)—, $C_{1-3}$ alkyl, $C_{1-3}$ acyl, halogen or hydroxy;
each $R_5$ and $R_6$ are independently hydrogen, phenylC$_{0-3}$ alkyl optionally subtituted by halogen or $C_{1-3}$ alkyl, acetyl, benzoyl or $C_{1-4}$ branched or unbranched alkyl optionally substituted by $C_{1-2}$ alkoxy, hydroxy or mono or diC$_{1-3}$ alkyl amino.

In another embodiment of the invention there is provided of the formula(I) as described immediately above, and wherein L is —O—;
Y is
a bond, —O—, —S—, —S(O)—, —S(O)$_2$—, —CH$_2$—, —CH(OH)—, —CH(CH$_3$)—, —NH—, —C(O)—NH—, >C(O), =CH=CHCH$_2$—;
or Y is imidazolyl, thiazolyl, pyrrolidinyl, oxazolyl or phenyl each optionally substituted by one hydroxy, oxo, $C_{1-3}$ alkyl, $C_{1-3}$ alkoxy, $C_{1-5}$ alkoxycarbonyl, NR$_5$R$_6$ or NR$_5$R$_6$—C(O)—;
wherein each Y is further covalently attached to NR$_5$R$_6$, methyl, ethyl, methoxy, phenoxy, hydroxy, $C_{3-6}$ cycloalkylC$_{0-2}$alkyl, phenylC$_{0-1}$ alkyl, piperazinylC$_{0-2}$ alkyl, piperidinyl, pyrrolidinylC$_{0-1}$ alkyl, morpholinylC$_{0-2}$ alkyl tetrahydrofuranylC$_{0-2}$ alkyl or pyridinyl, each abovelisted heterocycle, heteroaryl or phenyl is optionally substituted by one to two $C_{3-5}$ alkoxycarbonyl, acetyl, N-methylamide, N-ethylamide, methyl, ethyl, halogen or hydroxy;
each $R_5$ and $R_6$ are independently hydrogen, phenyl, benzyl each optionally subtituted by chlorine, bromine, fluorine or $C_{1-2}$ alkyl, acetyl, benzoyl or $C_{1-4}$ branched or unbranched alkyl optionally substituted by methoxy, hydroxy or mono or diC$_{1-3}$ alkyl amino; and
$R_3$ is $C_{1-3}$ alkyl-S(O)$_2$—NH— or $C_{1-3}$ alkyl-O—C(O)—NH—.

In an ultimately preferred embodiment of the invention there is provided of the formula(I) as described immediately above, and wherein $R_3$ is CH$_3$—S(O)$_2$—NH— or CH$_3$—O—C(O)—NH—.

The following are representative compounds of the formula (I) where n is 1 which can be made by the methods disclosed herein:

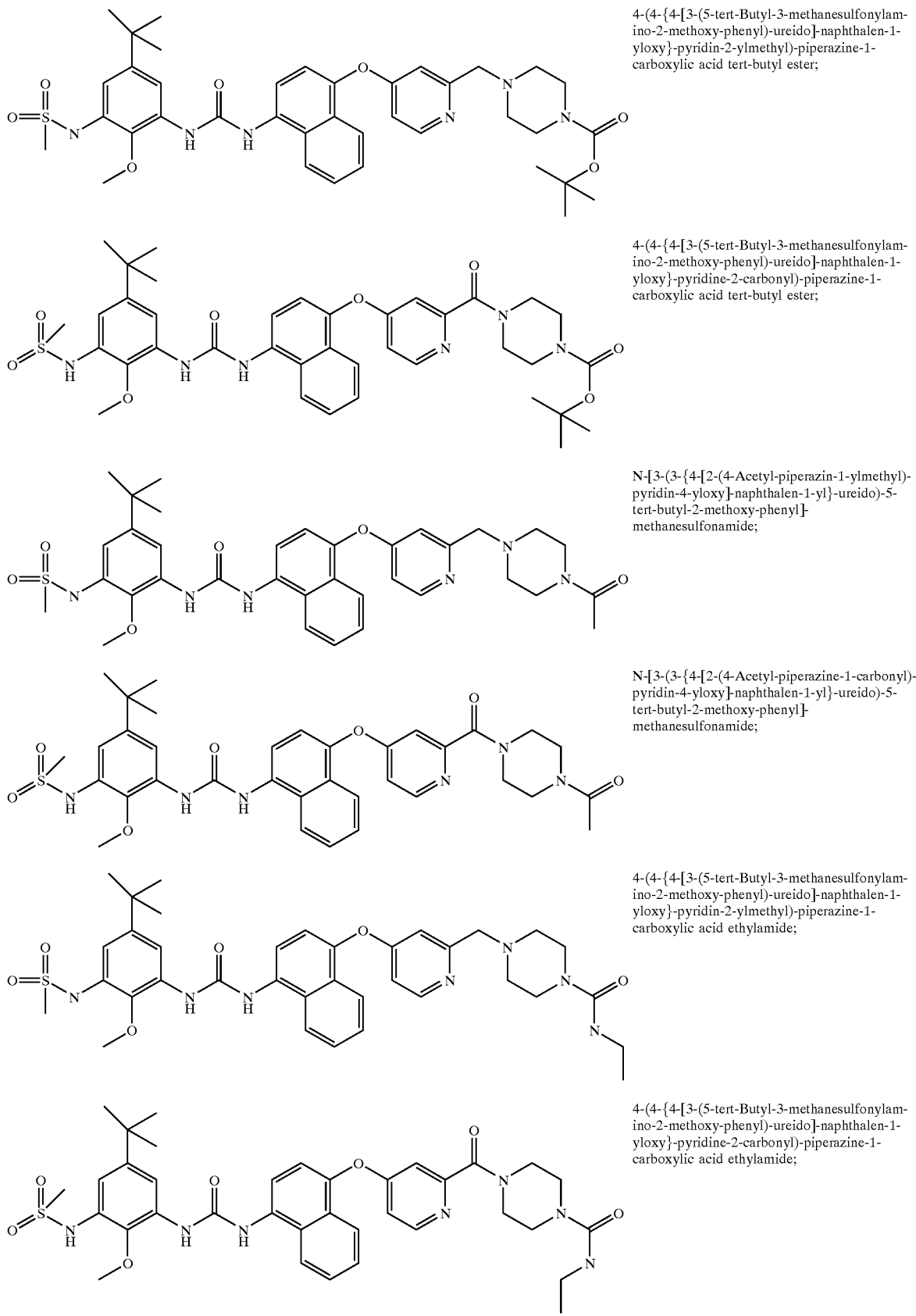

4-(4-{4-[3-(5-tert-Butyl-3-methanesulfonylamino-2-methoxy-phenyl)-ureido]-naphthalen-1-yloxy}-pyridin-2-ylmethyl)-piperazine-1-carboxylic acid tert-butyl ester;

4-(4-{4-[3-(5-tert-Butyl-3-methanesulfonylamino-2-methoxy-phenyl)-ureido]-naphthalen-1-yloxy}-pyridine-2-carbonyl)-piperazine-1-carboxylic acid tert-butyl ester;

N-[3-(3-{4-[2-(4-Acetyl-piperazin-1-ylmethyl)-pyridin-4-yloxy]-naphthalen-1-yl}-ureido)-5-tert-butyl-2-methoxy-phenyl]-methanesulfonamide;

N-[3-(3-{4-[2-(4-Acetyl-piperazine-1-carbonyl)-pyridin-4-yloxy]-naphthalen-1-yl}-ureido)-5-tert-butyl-2-methoxy-phenyl]-methanesulfonamide;

4-(4-{4-[3-(5-tert-Butyl-3-methanesulfonylamino-2-methoxy-phenyl)-ureido]-naphthalen-1-yloxy}-pyridin-2-ylmethyl)-piperazine-1-carboxylic acid ethylamide;

4-(4-{4-[3-(5-tert-Butyl-3-methanesulfonylamino-2-methoxy-phenyl)-ureido]-naphthalen-1-yloxy}-pyridine-2-carbonyl)-piperazine-1-carboxylic acid ethylamide;

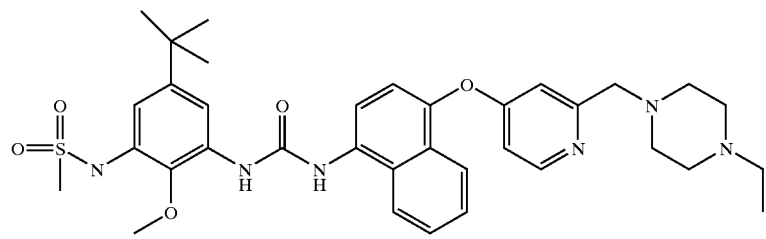

N-[5-tert-Butyl-3-(3-{4-[2-(4-ethyl-piperazin-1-ylmethyl)-pyridin-4-yloxy]-naphthalen-1-yl}-ureido)-2-methoxy-phenyl]-methanesulfonamide;

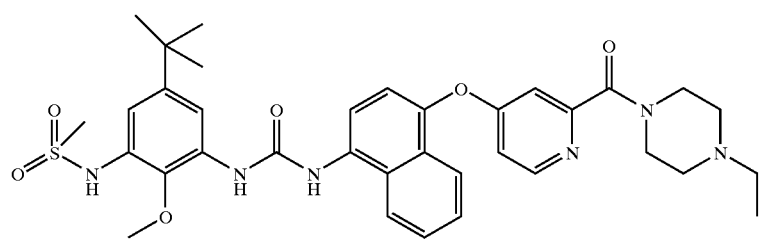

N-[5-tert-Butyl-3-(3-{4-[2-(4-ethyl-piperazine-1-carbonyl)-pyridin-4-yloxy]-naphthalen-1-yl}-ureido)-2-methoxy-phenyl]-methanesulfonamide;

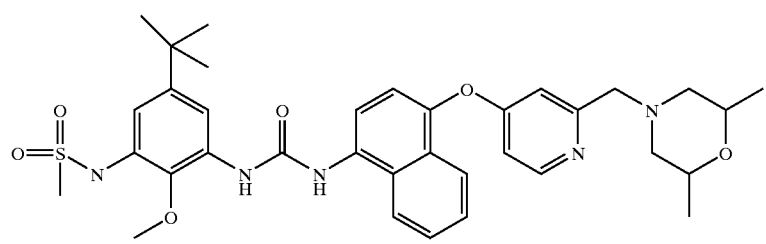

N-[5-tert-Butyl-3-(3-{4-[2-(2,6-dimethyl-morpholin-4-ylmethyl)-pyridin-4-yloxy]-naphthalen-1-yl}-ureido)-2-methoxy-phenyl]-methanesulfonamide;

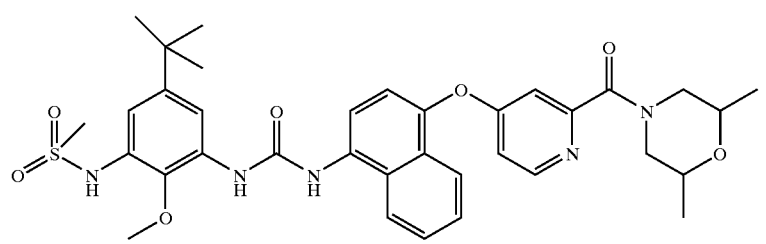

N-[5-tert-Butyl-3-(3-{4-[2-(2,6-dimethyl-morpholine-4-carbonyl)-pyridin-4-yloxy]-naphthalen-1-yl}-ureido)-2-methoxy-phenyl]-methanesulfonamide;

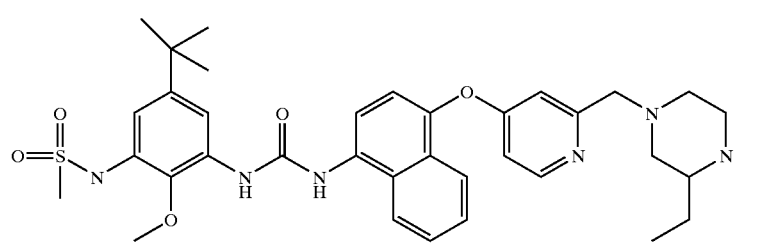

N-[5-tert-Butyl-3-(3-{4-[2-(3-ethyl-piperazin-1-ylmethyl)-pyridin-4-yloxy]-naphthalen-1-yl}-ureido)-2-methoxy-phenyl]-methanesulfonamide;

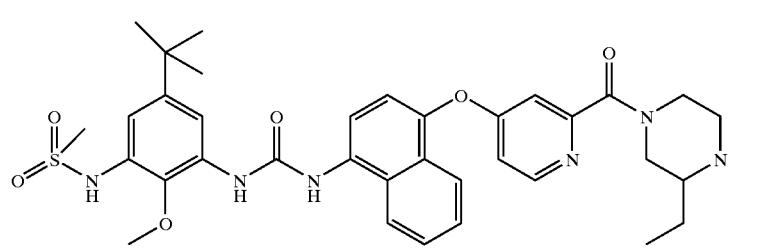

N-[5-tert-Butyl-3-(3-{4-[2-(3-ethyl-piperazine-1-carbonyl)-pyridin-4-yloxy]-naphthalen-1-yl}-ureido)-2-methoxy-phenyl]-methanesulfonamide;

-continued

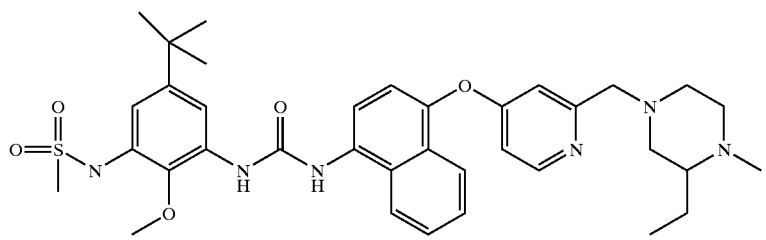

N-[5-tert-Butyl-3-(3-{4-[2-(3-ethyl-4-methyl-piperazin-1-ylmethyl)-pyridin-4-yloxy]-naphthalen-1-yl}-ureido)-2-methoxy-phenyl]-methanesulfonamide;

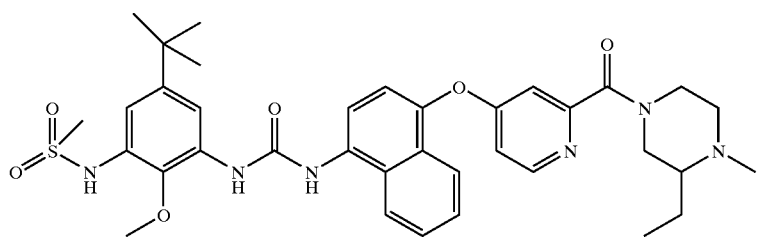

N-[5-tert-Butyl-3-(3-{4-[2-(3-ethyl-4-methyl-piperazine-1-carbonyl)-pyridin-4-yloxy]-naphthalen-1-yl}-ureido)-2-methoxy-phenyl]-methanesulfonamide;

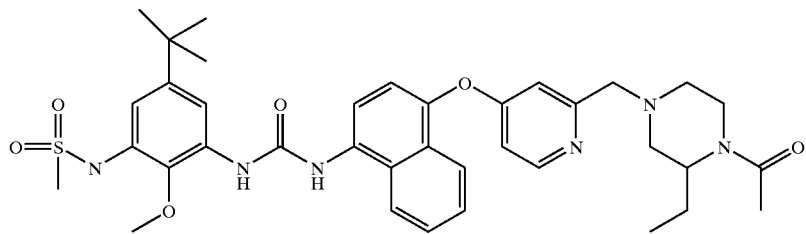

N-[3-(3-{4-[2-(4-Acetyl-3-ethyl-piperazin-1-ylmethyl)-pyridin-4-yloxy]-naphthalen-1-yl}-ureido)-5-tert-butyl-2-methoxy-phenyl]-methanesulfonamide;

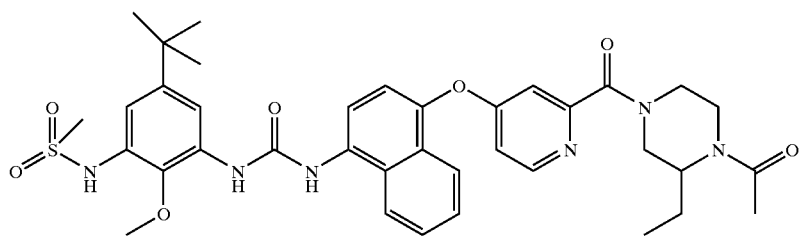

N-[3-(3-{4-[2-(4-Acetyl-3-ethyl-piperazine-1-carbonyl)-pyridin-4-yloxy]-naphthalen-1-yl}-ureido)-5-tert-butyl-2-methoxy-phenyl]-methanesulfonamide;

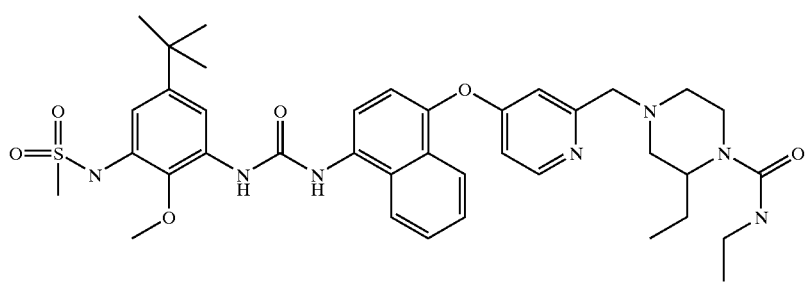

4-(4-{4-[3-(5-tert-Butyl-3-methanesulfonylam-ino-2-methoxy-phenyl)-ureido]-naphthalen-1-yloxy}-pyridin-2-ylmethyl)-2-ethyl-piperazine-1-carboxylic acid ethylamide;

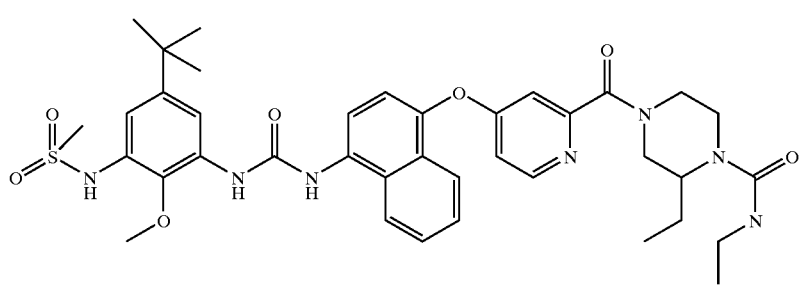

4-(4-{4-[3-(5-tert-Butyl-3-methanesulfonylam-ino-2-methoxy-phenyl)-ureido]-naphthalen-1-yloxy}-pyridine-2-carbonyl)-2-ethyl-piperazine-1-carboxylic acid ethylamide;

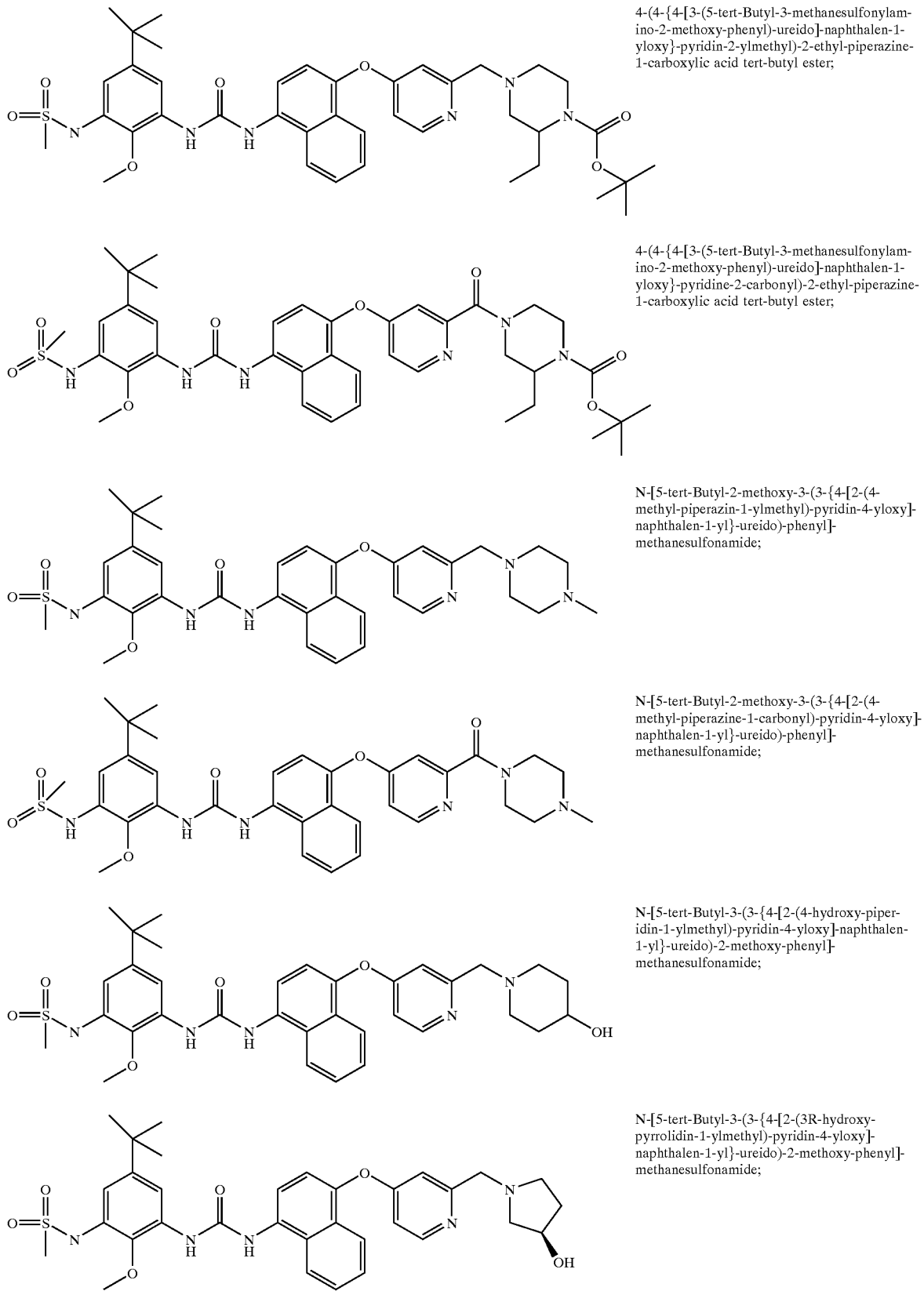

4-(4-{4-[3-(5-tert-Butyl-3-methanesulfonylamino-2-methoxy-phenyl)-ureido]-naphthalen-1-yloxy}-pyridin-2-ylmethyl)-2-ethyl-piperazine-1-carboxylic acid tert-butyl ester;

4-(4-{4-[3-(5-tert-Butyl-3-methanesulfonylamino-2-methoxy-phenyl)-ureido]-naphthalen-1-yloxy}-pyridine-2-carbonyl)-2-ethyl-piperazine-1-carboxylic acid tert-butyl ester;

N-[5-tert-Butyl-2-methoxy-3-(3-{4-[2-(4-methyl-piperazin-1-ylmethyl)-pyridin-4-yloxy]-naphthalen-1-yl}-ureido)-phenyl]-methanesulfonamide;

N-[5-tert-Butyl-2-methoxy-3-(3-{4-[2-(4-methyl-piperazine-1-carbonyl)-pyridin-4-yloxy]-naphthalen-1-yl}-ureido)-phenyl]-methanesulfonamide;

N-[5-tert-Butyl-3-(3-{4-[2-(4-hydroxy-piperidin-1-ylmethyl)-pyridin-4-yloxy]-naphthalen-1-yl}-ureido)-2-methoxy-phenyl]-methanesulfonamide;

N-[5-tert-Butyl-3-(3-{4-[2-(3R-hydroxy-pyrrolidin-1-ylmethyl)-pyridin-4-yloxy]-naphthalen-1-yl}-ureido)-2-methoxy-phenyl]-methanesulfonamide;

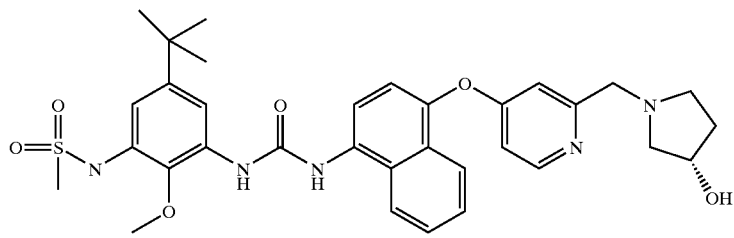

N-[5-tert-Butyl-3-(3-{4-[2-(3S-hydroxy-pyrrolidin-1-ylmethyl)-pyridin-4-yloxy]-naphthalen-1-yl}-ureido)-2-methoxy-phenyl]-methanesulfonamide;

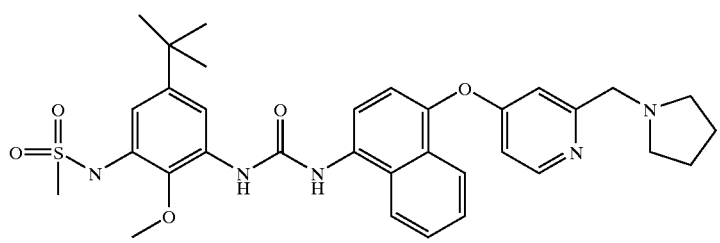

N-(5-tert-Butyl-2-methoxy-3-{3-[4-(2-pyrrolidin-1-ylmethyl-pyridin-4-yloxy)-naphthalen-1-yl]-ureido}-phenyl)-methanesulfonamide;

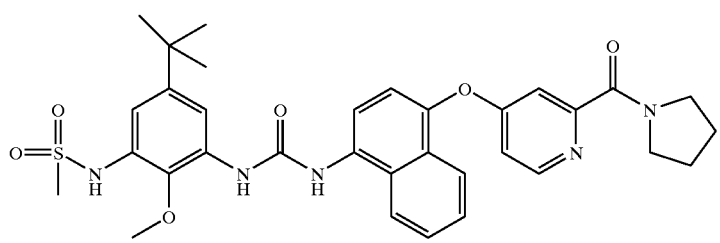

N-[5-tert-Butyl-2-methoxy-3-(3-{4-[2-(pyrrolidine-1-carbonyl)-pyridin-4-yloxy]-naphthalen-1-yl}-ureido)-phenyl]-methanesulfonamide;

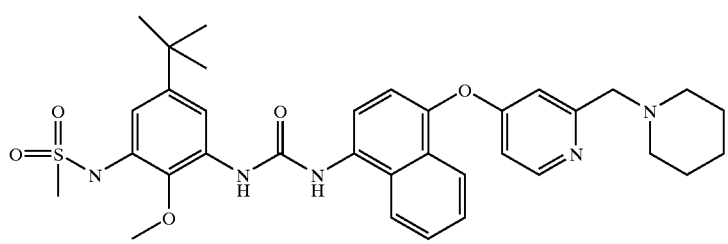

N-(5-tert-Butyl-2-methoxy-3-{3-[4-(2-piperidin-1-ylmethyl-pyridin-4-yloxy)-naphthalen-1-yl]-ureido}-phenyl)-methanesulfonamide;

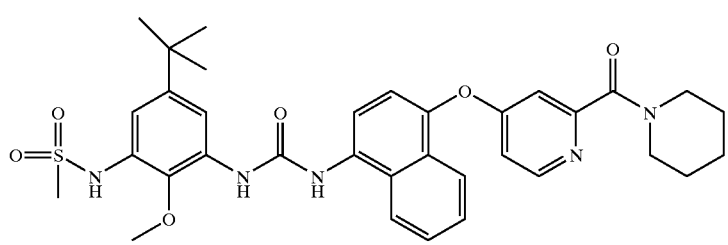

N-[5-tert-Butyl-2-methoxy-3-(3-{4-[2-(piperidine-1-carbonyl)-pyridin-4-yloxy]-naphthalen-1-yl}-ureido)-phenyl]-methanesulfonamide;

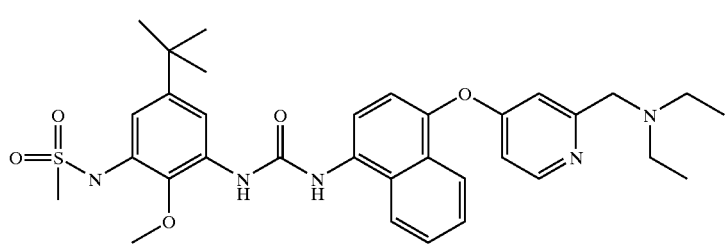

N-(5-tert-Butyl-3-{3-[4-(2-diethylaminomethyl-pyridin-4-yloxy)-naphthalen-1-yl]-ureido}-2-methoxy-phenyl)-methanesulfonamide;

-continued

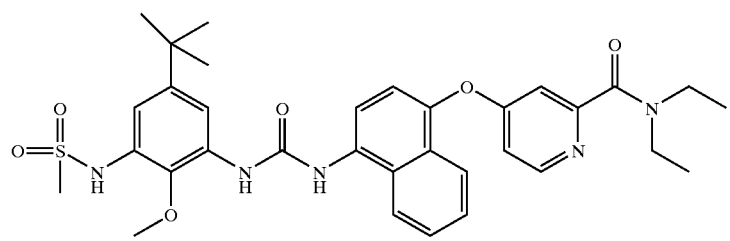

4-{4-[3-(5-tert-Butyl-3-methanesulfonylamino-2-methoxy-phenyl)-ureido]-naphthalen-1-yl-oxy}-pyridine-2-carboxylic acid diethylamide;

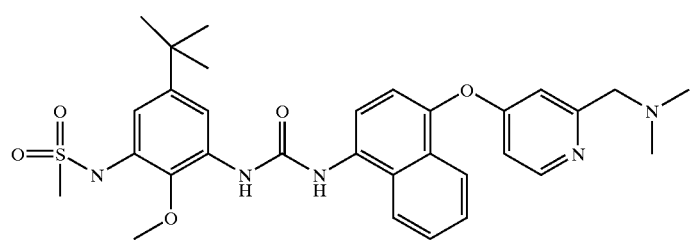

N-(5-tert-Butyl-3-{3-[4-(2-dimethylamino-methyl-pyridin-4-yloxy)-naphthalen-1-yl]-ureido}-2-methoxy-phenyl)-methanesulfonamide;

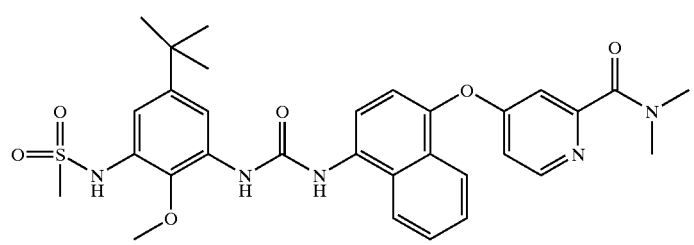

4-{4-[3-(5-tert-Butyl-3-methanesulfonylamino-2-methoxy-phenyl)-ureido]-naphthalen-1-yloxy}-pyridine-2-carboxylic acid dimethylamide;

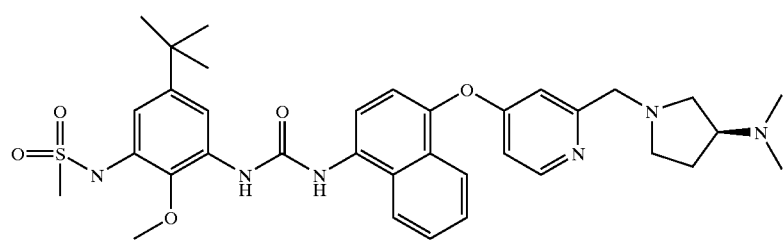

N-[5-tert-Butyl-3-(3-{4-[2-(3S-dimethylam-ino-pyrrolidin-1-ylmethyl)-pyridin-4-yloxy]-naphthalen-1-yl}-ureido)-2-methoxy-phenyl]-methanesulfonamide;

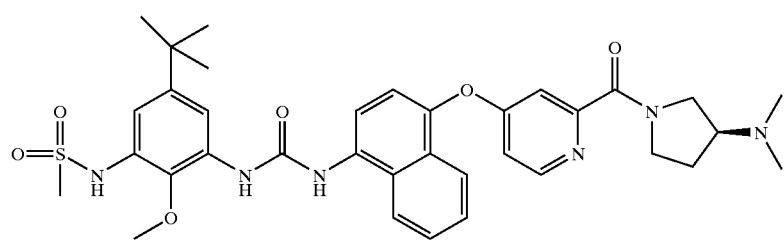

N-[5-tert-Butyl-3-(3-{4-[2-(3S-dimethylamino-pyrrolidine-1-carbonyl)-pyridin-4-yloxy]-naphthalen-1-yl}-ureido)-2-methoxy-phenyl]-methanesulfonamide;

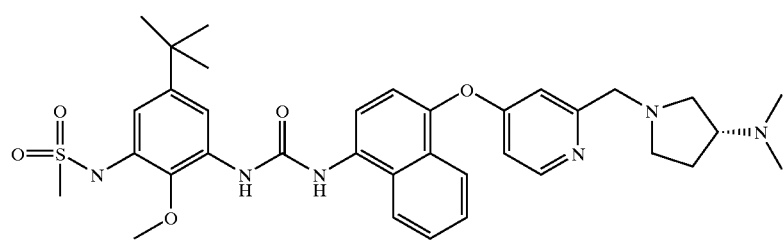

N-[5-tert-Butyl-3-(3-{4-[2-(3R-dimethylamino-pyrrolidin-1-ylmethyl)-pyridin-4-yloxy]-naphthalen-1-yl}-ureido)-2-methoxy-phenyl]-methanesulfonamide;

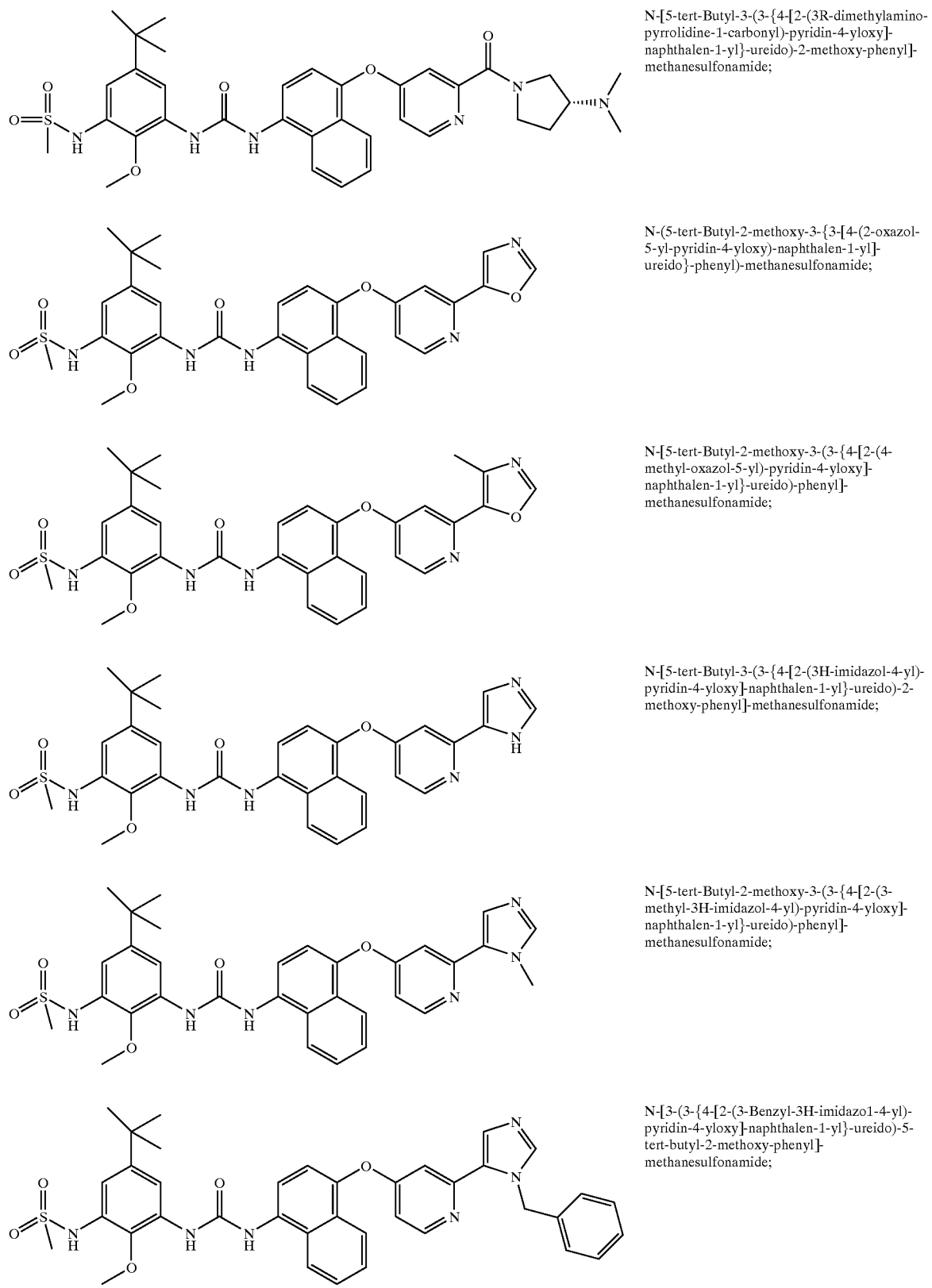

N-[5-tert-Butyl-3-(3-{4-[2-(3R-dimethylamino-pyrrolidine-1-carbonyl)-pyridin-4-yloxy]-naphthalen-1-yl}-ureido)-2-methoxy-phenyl]-methanesulfonamide;

N-(5-tert-Butyl-2-methoxy-3-{3-[4-(2-oxazol-5-yl-pyridin-4-yloxy)-naphthalen-1-yl]-ureido}-phenyl)-methanesulfonamide;

N-[5-tert-Butyl-2-methoxy-3-(3-{4-[2-(4-methyl-oxazol-5-yl)-pyridin-4-yloxy]-naphthalen-1-yl}-ureido)-phenyl]-methanesulfonamide;

N-[5-tert-Butyl-3-(3-{4-[2-(3H-imidazol-4-yl)-pyridin-4-yloxy]-naphthalen-1-yl}-ureido)-2-methoxy-phenyl]-methanesulfonamide;

N-[5-tert-Butyl-2-methoxy-3-(3-{4-[2-(3-methyl-3H-imidazol-4-yl)-pyridin-4-yloxy]-naphthalen-1-yl}-ureido)-phenyl]-methanesulfonamide;

N-[3-(3-{4-[2-(3-Benzyl-3H-imidazol-4-yl)-pyridin-4-yloxy]-naphthalen-1-yl}-ureido)-5-tert-butyl-2-methoxy-phenyl]-methanesulfonamide;

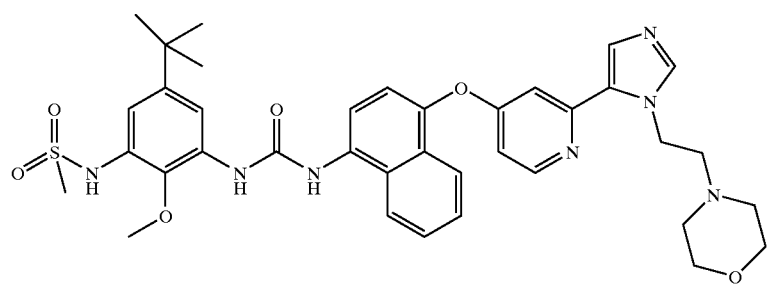

N-{5-tert-Butyl-2-methoxy-3-[3-(4-{2-[3-(2-morpholin-4-yl-ethyl)-3H-imidazol-4-yl]-pyridin-4-yloxy}-naphthalen-1-yl)-ureido]-phenyl}-methanesulfonamide;

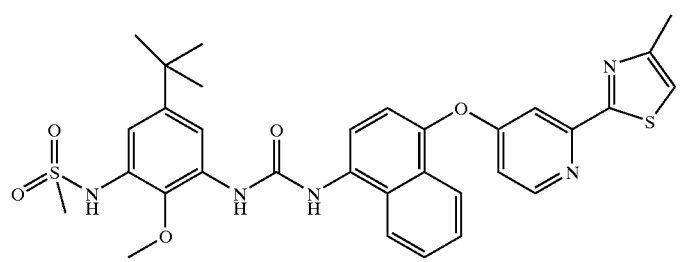

N-[5-tert-Butyl-2-methoxy-3-(3-{4-[2-(4-methyl-thiazol-2-yl)-pyridin-4-yloxy]-naphthalen-1-yl}-ureido)-phenyl]-methanesulfonamide;

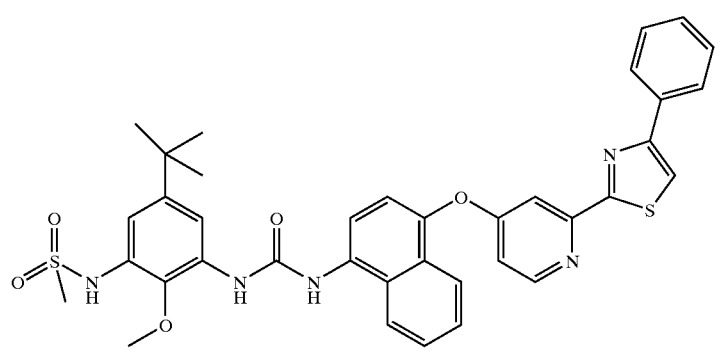

N-[5-tert-Butyl-2-methoxy-3-(3-{4-[2-(4-phenyl-thiazol-2-yl)-pyridin-4-yloxy]-naphthalen-1-yl}-ureido)-phenyl]-methanesulfonamide;

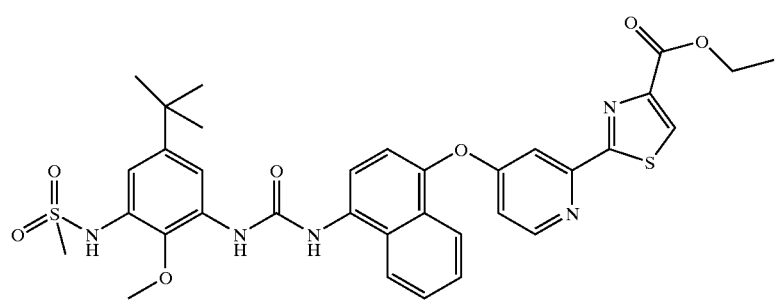

2-(4-{4-[3-(5-tert-Butyl-3-methanesulfonyl-amino-2-methoxy-phenyl)-ureido]-naphthalen-1-yloxy}-pyridin-2-yl)-thiazole-4-carboxylic acid ethyl ester;

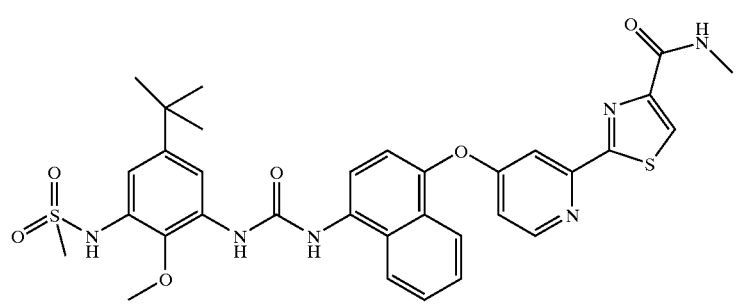

2-(4-{4-[3-(5-tert-Butyl-3-methanesulfonyl-amino-2-methoxy-phenyl)-ureido]-naphthalen-1-yloxy}-pyridin-2-yl)-thiazole-4-carboxylic acid methylamide;

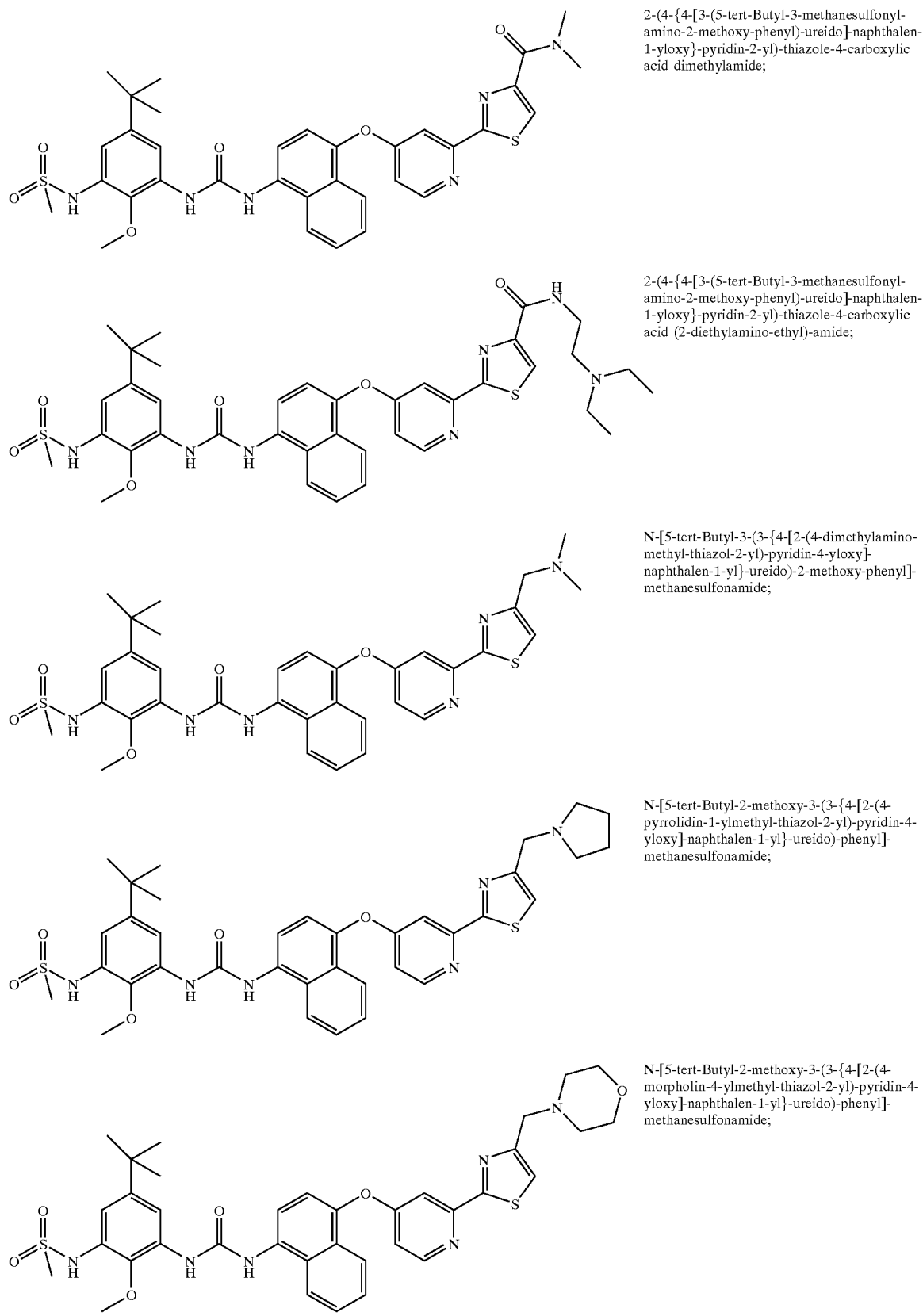

2-(4-{4-[3-(5-tert-Butyl-3-methanesulfonyl-amino-2-methoxy-phenyl)-ureido]-naphthalen-1-yloxy}-pyridin-2-yl)-thiazole-4-carboxylic acid dimethylamide;

2-(4-{4-[3-(5-tert-Butyl-3-methanesulfonyl-amino-2-methoxy-phenyl)-ureido]-naphthalen-1-yloxy}-pyridin-2-yl)-thiazole-4-carboxylic acid (2-diethylamino-ethyl)-amide;

N-[5-tert-Butyl-3-(3-{4-[2-(4-dimethylamino-methyl-thiazol-2-yl)-pyridin-4-yloxy]-naphthalen-1-yl}-ureido)-2-methoxy-phenyl]-methanesulfonamide;

N-[5-tert-Butyl-2-methoxy-3-(3-{4-[2-(4-pyrrolidin-1-ylmethyl-thiazol-2-yl)-pyridin-4-yloxy]-naphthalen-1-yl}-ureido)-phenyl]-methanesulfonamide;

N-[5-tert-Butyl-2-methoxy-3-(3-{4-[2-(4-morpholin-4-ylmethyl-thiazol-2-yl)-pyridin-4-yloxy]-naphthalen-1-yl}-ureido)-phenyl]-methanesulfonamide;

-continued

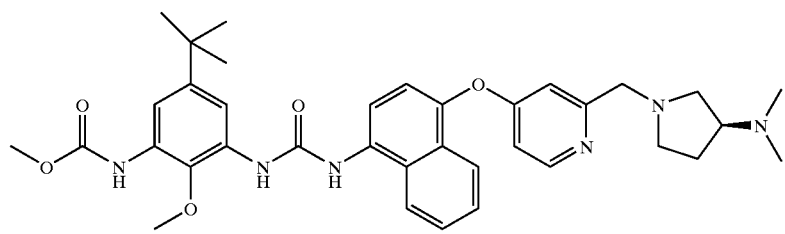
[5-tert-Butyl-3-(3-{4-[2-(3S-dimethylamino-pyrrolidin-1-ylmethyl)-pyridin-4-yloxy]-naphthalen-1-yl}-ureido)-2-methoxy-phenyl]-carbamic acid methyl ester;

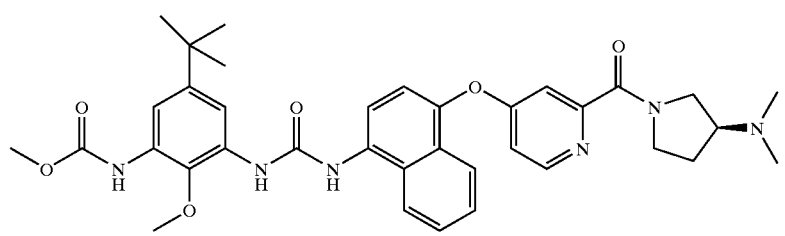
[5-tert-Butyl-3-(3-{4-[2-(3S-dimethylamino-pyrrolidine-1-carbonyl)-pyridin-4-yloxy]-naphthalen-1-yl}-ureido)-2-methoxy-phenyl]-carbamic acid methyl ester;

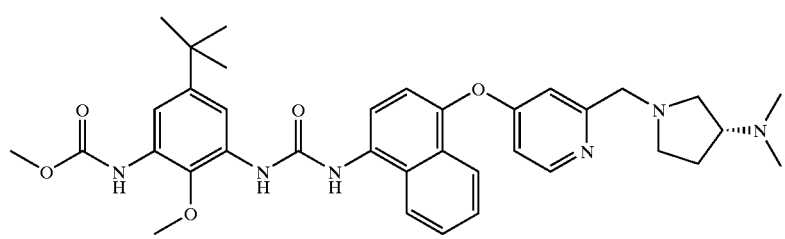
[5-tert-Butyl-3-(3-{4-[2-(3R-dimethylamino-pyrrolidin-1-ylmethyl)-pyridin-4-yloxy]-naphthalen-1-yl}-ureido)-2-methoxy-pheny]-carbamic acid methyl ester;

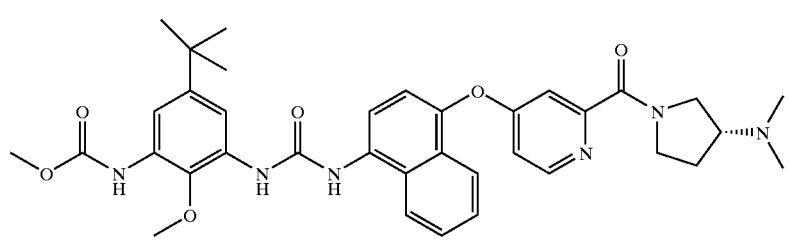
[5-tert-Butyl-3-(3-{4-[2-(3R-dimethylamino-pyrrolidine-1-carbonyl)-pyridin-4-yloxy]-naphthalen-1-yl}-ureido)-2-methoxy-phenyl]-carbamic acid methyl ester;

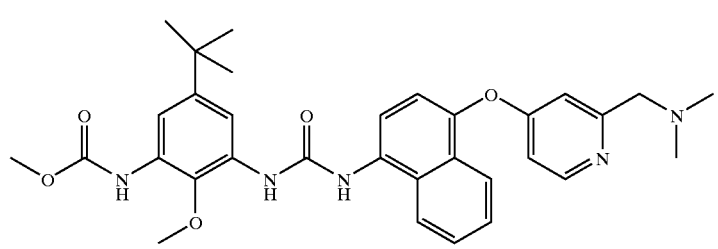
(5-tert-Butyl-3-{3-[4-(2-dimethylaminomethyl-pyridin-4-yloxy)-naphthalen-1-yl]-ureido}-2-methoxy-phenyl)-carbamic acid methyl ester;

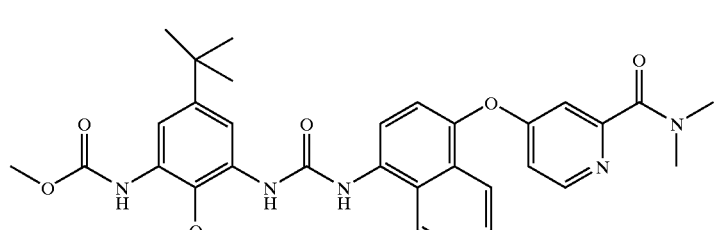
(5-tert-Butyl-3-{3-[4-(2-dimethylcarbamoyl-pyridin-4-yloxy)-naphthalen-1-yl]-ureido}-2-methoxy-phenyl)-carbamic acid methyl ester;

-continued

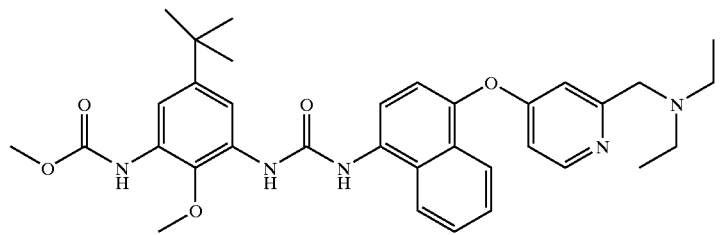

(5-tert-Butyl-3-{3-[4-(2-diethylaminomethyl-pyridin-4-yloxy)-naphthalen-1-yl]-ureido}-2-methoxy-phenyl)-carbamic acid methyl ester;

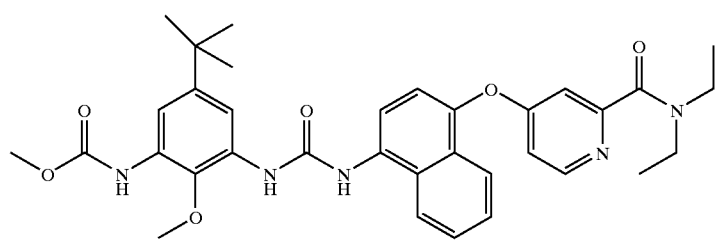

(5-tert-Butyl-3-{3-[4-(2-diethylcarbamoyl-pyridin-4-yloxy)-naphthalen-1-yl]-ureido}-2-methoxy-phenyl)-carbamic acid methyl ester;

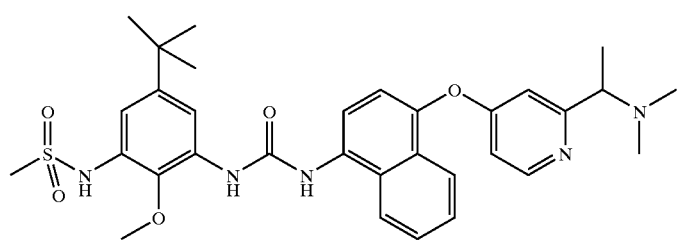

N-[5-tert-Butyl-3-(3-{4-[2-(1-dimethylamino-ethyl)-pyridin-4-yloxy]-naphthalen-1-yl}-ureido)-2-methoxy-phenyl]-methanesulfonamide;

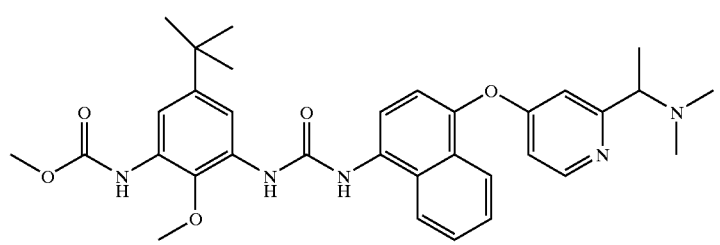

[5-tert-Butyl-3-(3-{4-[2-(1-dimethylamino-ethyl)-pyridin-4-yloxy]-naphthalen-1-yl}-ureido)-2-methoxy-phenyl]-carbamic acid methyl ester;

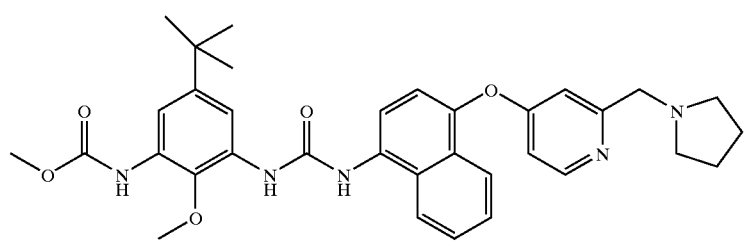

(5-tert-Butyl-2-methoxy-3-{3-[4-(2-pyrrolidin-1-ylmethyl-pyridin-4-yloxy)-naphthalen-1-yl]-ureido}-phenyl)-carbamic acid methyl ester;

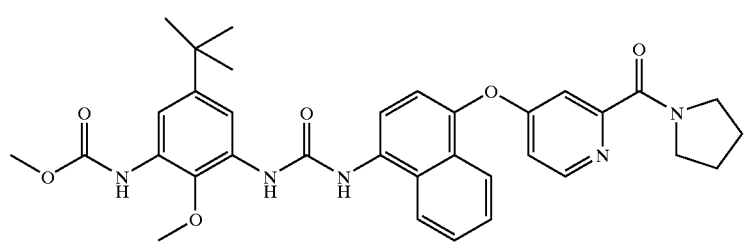

[5-tert-Butyl-2-methoxy-3-(3-{4-[2-(pyrrolidine-1-carbonyl)-pyridin-4-yloxy]-naphthalen-1-yl}-ureido)-phenyl]-carbamic acid methyl ester;

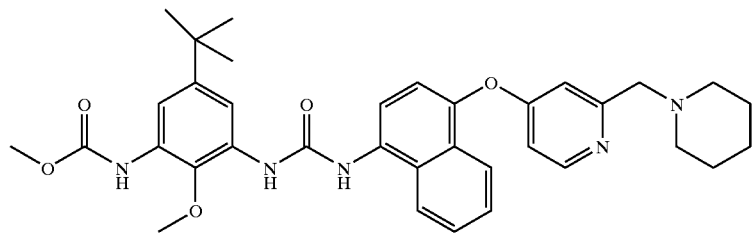

(5-tert-Butyl-2-methoxy-3-{3-[4-(2-piperidin-1-ylmethyl-pyridin-4-yloxy)-naphthalen-1-yl]-ureido}-phenyl)-carbamic acid methyl ester;

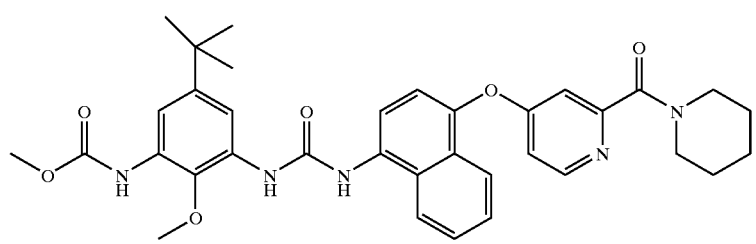

[5-tert-Butyl-2-methoxy-3-(3-{4-[2-(piperidine-1-carbonyl)-pyridin-4-yloxy]-naphthalen-1-yl}-ureido)-phenyl]-carbamic acid methyl ester;

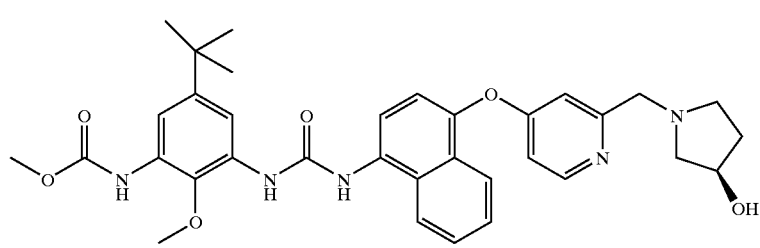

[5-tert-Butyl-3-(3-{4-[2-(3R-hydroxy-pyrrolidin-1-ylmethyl)-pyridin-4-yloxy]-naphthalen-1-yl}-ureido)-2-methoxy-phenyl]-carbamic acid methyl ester;

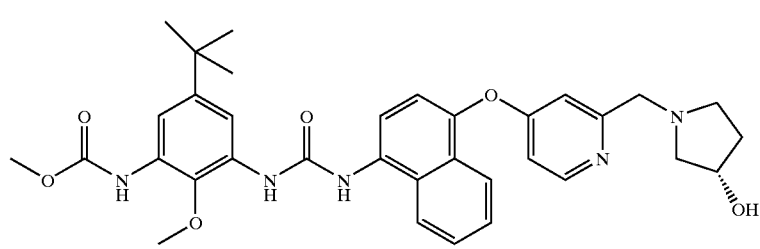

[5-tert-Butyl-3-(3-{4-[2-(3S-hydroxy-pyrrolidin-1-ylmethyl)-pyridin-4-yloxy]-naphthalen-1-yl}-ureido)-2-methoxy-phenyl]-carbamic acid methyl ester;

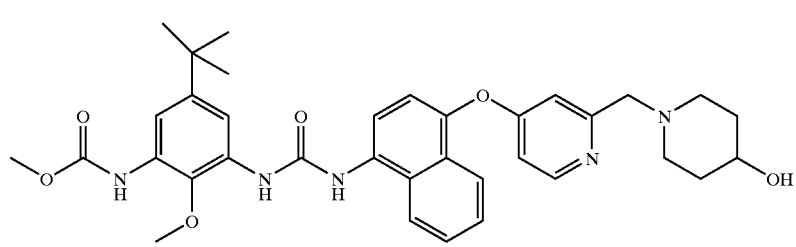

[5-tert-Butyl-3-(3-{4-[2-(4-hydroxy-piperidin-1-ylmethyl)-pyridin-4-yloxy]-naphthalen-1-yl}-ureido)-2-methoxy-phenyl]-carbamic acid methyl ester;

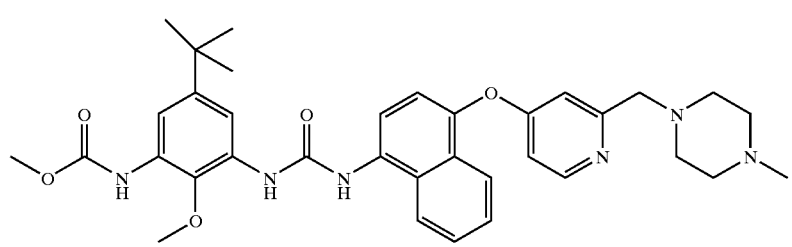

[5-tert-Butyl-2-methoxy-3-(3-{4-[2-(4-methyl-piperazin-1-ylmethyl)-pyridin-4-yloxy]-naphthalen-1-yl}-ureido)-phenyl]-carbamic acid methyl ester;

-continued

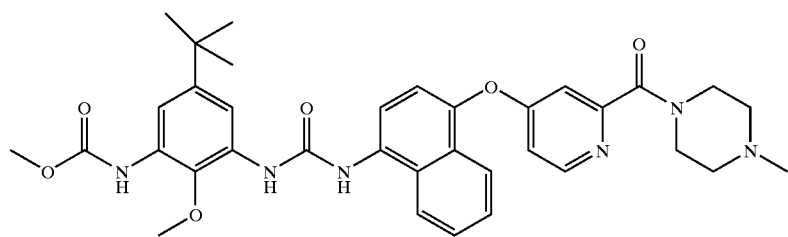

[5-tert-Butyl-2-methoxy-3-(3-{4-[2-(4-methyl-piperazine-1-carbonyl)-pyridin-4-yloxy]-naphthalen-1-yl}-ureido)-phenyl]-carbamic acid methyl ester;

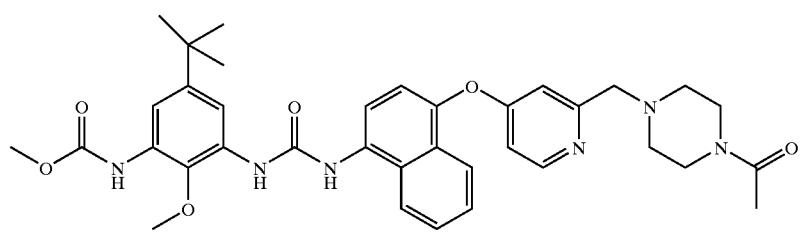

[3-(3-{4-[2-(4-Acetyl-piperazin-1-ylmethyl)-pyridin-4-yloxy]-naphthalen-1-yl}-ureido)-5-tert-butyl-2-methoxy-phenyl]-carbamic acid methyl ester;

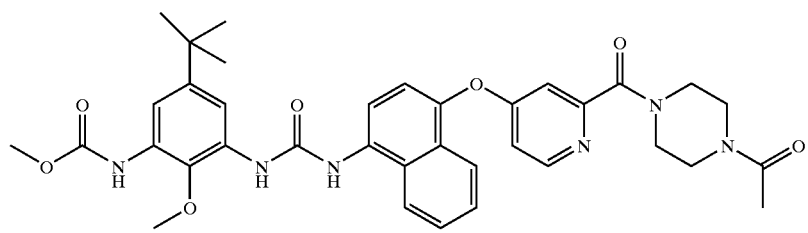

[3-(3-{4-[2-(4-Acetyl-piperazine-1-carbonyl)-pyridin-4-yloxy]-naphthalen-1-yl}-ureido)-5-tert-butyl-2-methoxy-phenyl]-carbamic acid methyl ester;

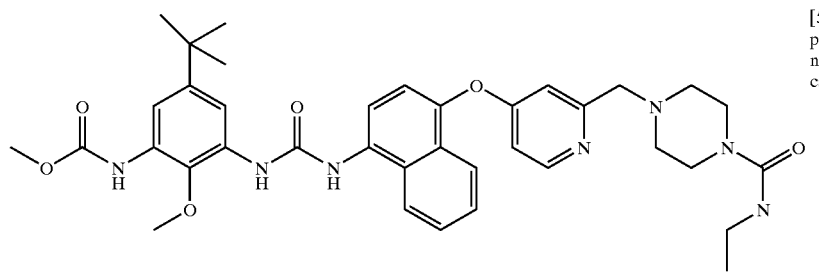

[5-tert-Butyl-3-(3-{4-[2-(4-ethylcarbamoyl-piperazin-1-ylmethyl)-pyridin-4-yloxy]-naphthalen-1-yl}-ureido)-2-methoxy-phenyl]-carbamic acid methyl ester;

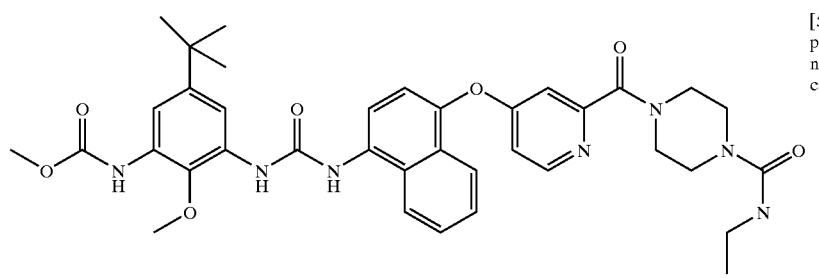

[5-tert-Butyl-3-(3-{4-[2-(4-ethylcarbamoyl-piperazine-1-carbonyl)-pyridin-4-yloxy]-naphthalen-1-yl}-ureido)-2-methoxy-phenyl]-carbamic acid methyl ester;

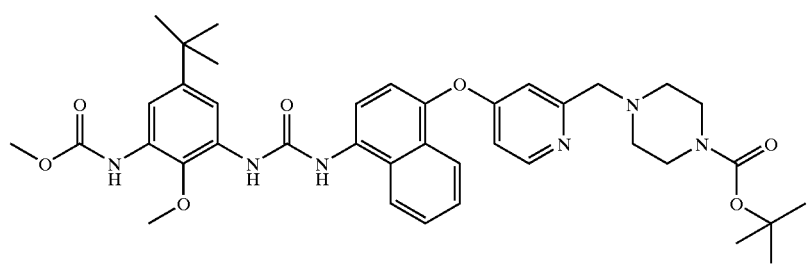

4-(4-{4-[3-(5-tert-Butyl-2-methoxy-3-methoxy-carbonylamino-phenyl)-ureido]-naphthalen-1-yloxy}-pyridine-2-carbonyl)-piperazine-1-carboxylic acid tert-butyl ester;

-continued

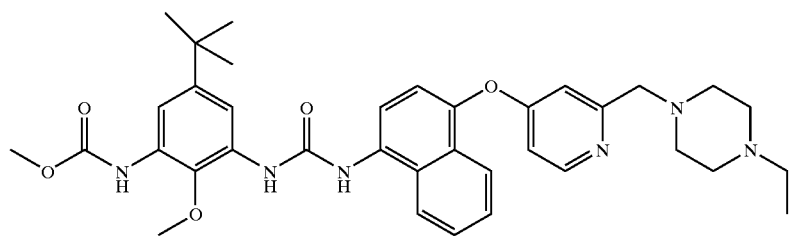

[5-tert-Butyl-3-(3-{4-[2-(4-ethyl-piperazin-1-ylmethyl)-pyridin-4-yloxy]-naphthalen-1-yl}-ureido)-2-methoxy-phenyl]-carbamic acid methyl ester;

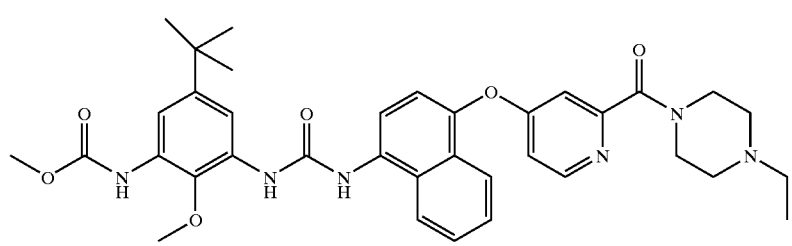

[5-tert-Butyl-3-(3-{4-[2-(4-ethyl-piperazine-1-carbonyl)-pyridin-4-yloxy]-naphthalen-1-yl}-ureido)-2-methoxy-phenyl]-carbamic acid methyl ester;

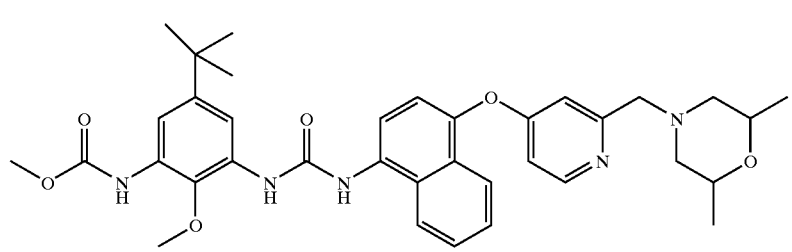

[5-tert-Butyl-3-(3-{4-[2-(2,6-dimethyl-morpholin-4-ylmethyl)-pyridin-4-yloxy]-naphthalen-1-yl}-ureido)-2-methoxy-phenyl]-carbamic acid methyl ester;

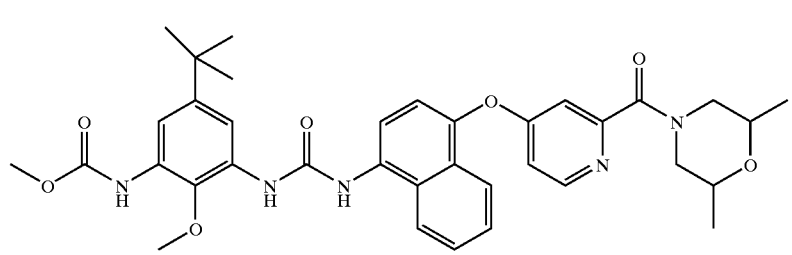

[5-tert-Butyl-3-(3-{4-[2-(2,6-dimethyl-morpholine-4-carbonyl)-pyridin-4-yloxy]-naphthalen-1-yl}-ureido)-2-methoxy-phenyl]-carbamic acid methyl ester;

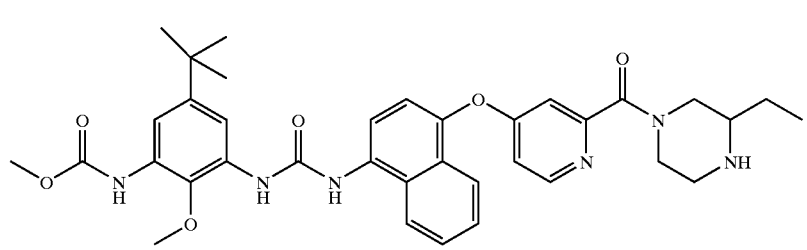

[5-tert-Butyl-3-(3-{4-[2-(3-ethyl-piperazine-1-carbonyl)-pyridin-4-yloxy]-naphthalen-1-yl}-ureido)-2-methoxy-phenyl]-carbamic acid methyl ester;

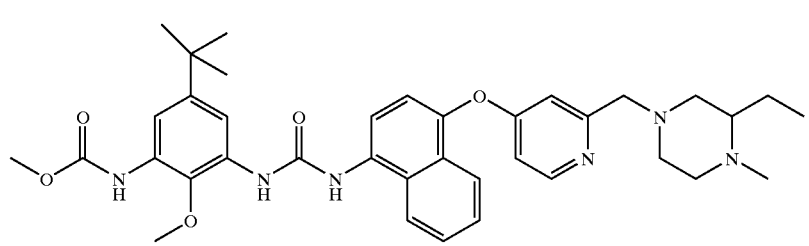

[5-tert-Butyl-3-(3-{4-[2-(3-ethyl-4-methyl-piperazin-1-ylmethyl)-pyridin-4-yloxy]-naphthalen-1-yl}-ureido)-2-methoxy-phenyl]-carbamic acid methyl ester;

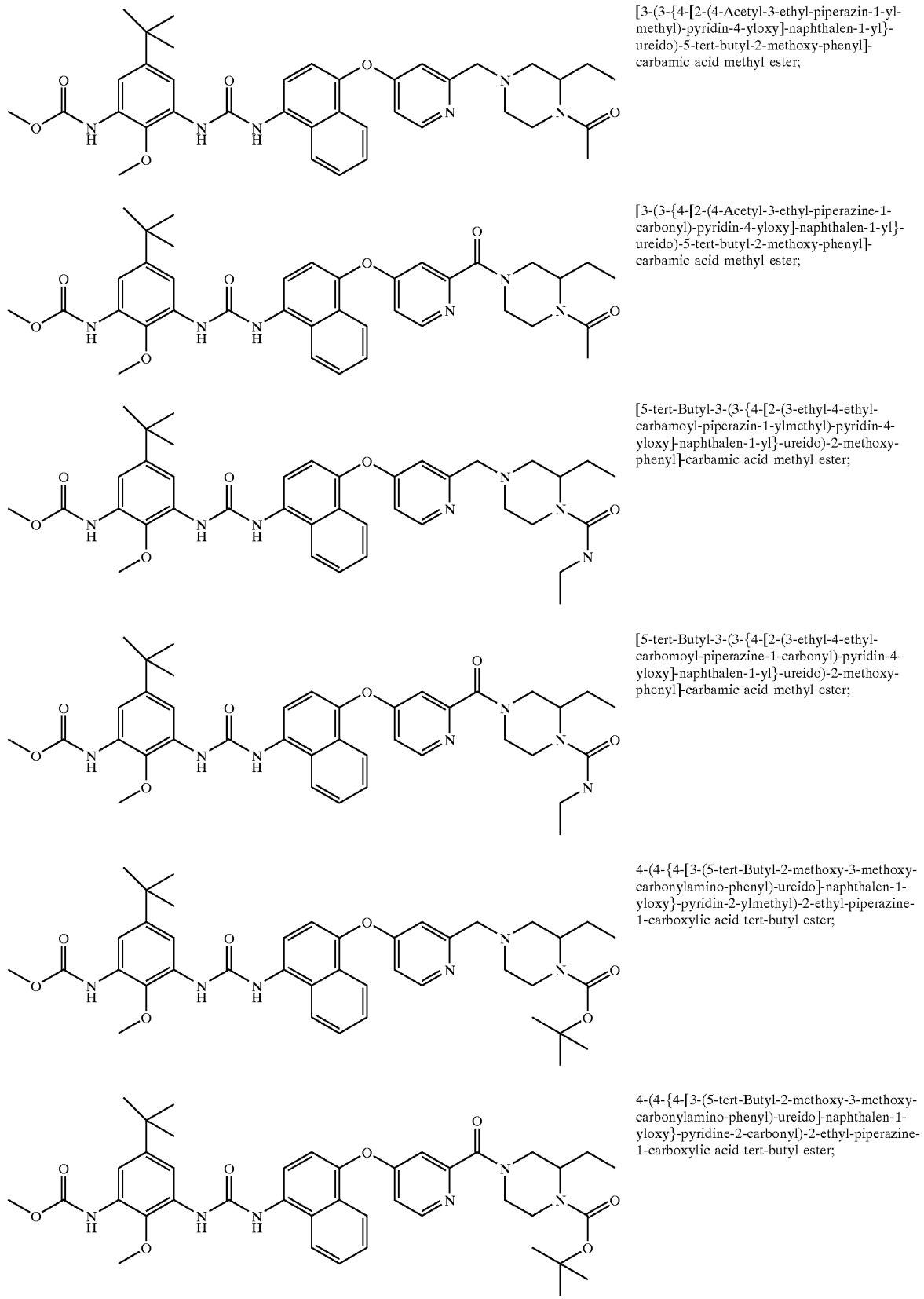

[3-(3-{4-[2-(4-Acetyl-3-ethyl-piperazin-1-yl-methyl)-pyridin-4-yloxy]-naphthalen-1-yl}-ureido)-5-tert-butyl-2-methoxy-phenyl]-carbamic acid methyl ester;

[3-(3-{4-[2-(4-Acetyl-3-ethyl-piperazine-1-carbonyl)-pyridin-4-yloxy]-naphthalen-1-yl}-ureido)-5-tert-butyl-2-methoxy-phenyl]-carbamic acid methyl ester;

[5-tert-Butyl-3-(3-{4-[2-(3-ethyl-4-ethyl-carbamoyl-piperazin-1-ylmethyl)-pyridin-4-yloxy]-naphthalen-1-yl}-ureido)-2-methoxy-phenyl]-carbamic acid methyl ester;

[5-tert-Butyl-3-(3-{4-[2-(3-ethyl-4-ethyl-carbomoyl-piperazine-1-carbonyl)-pyridin-4-yloxy]-naphthalen-1-yl}-ureido)-2-methoxy-phenyl]-carbamic acid methyl ester;

4-(4-{4-[3-(5-tert-Butyl-2-methoxy-3-methoxy-carbonylamino-phenyl)-ureido]-naphthalen-1-yloxy}-pyridin-2-ylmethyl)-2-ethyl-piperazine-1-carboxylic acid tert-butyl ester;

4-(4-{4-[3-(5-tert-Butyl-2-methoxy-3-methoxy-carbonylamino-phenyl)-ureido]-naphthalen-1-yloxy}-pyridine-2-carbonyl)-2-ethyl-piperazine-1-carboxylic acid tert-butyl ester;

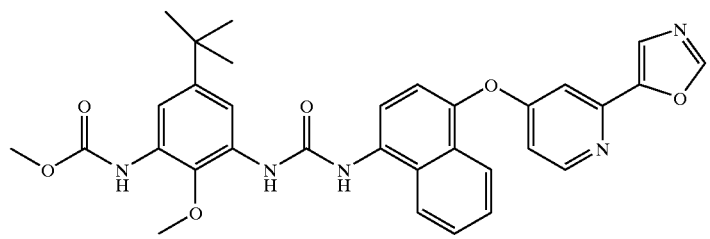

(5-tert-Butyl-2-methoxy-3-{3-[4-(2-oxazol-5-yl-pyridin-4-yloxy)-naphthalen-1-yl]-ureido}-phenyl)-carbamic acid methyl ester;

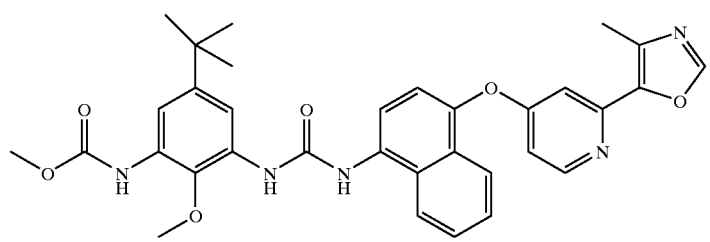

[5-tert-Butyl-2-methoxy-3-(3-{4-[2-(4-methyl-oxazol-5-yl)-pyridin-4-yloxy]-naphthalen-1-yl}-ureido)-phenyl]-carbamic acid methyl ester;

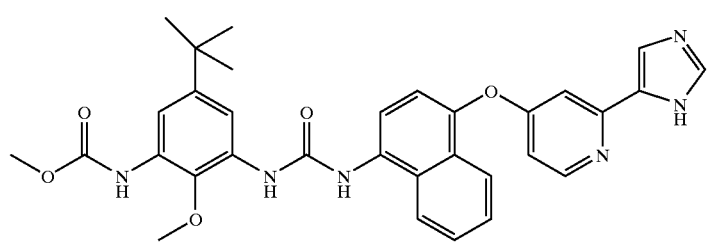

[5-tert-Butyl-3-(3-{4-[2-(3H-imidazol-4-yl)-pyridin-4-yloxy]-naphthalen-1-yl}-ureido)-2-methoxy-phenyl]-carbamic acid methyl ester;

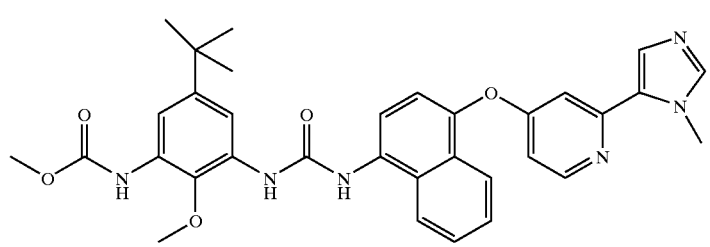

[5-tert-Butyl-2-methoxy-3-(3-{4-[2-(3-methyl-3H-imidazol-4-yl)-pyridin-4-yloxy]-naphthalen-1-yl}-ureido)-phenyl]-carbamic acid methyl ester;

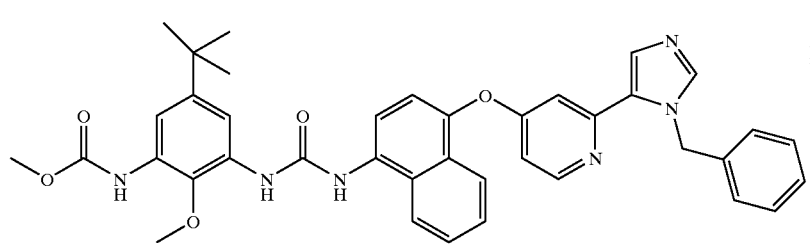

[3-(3-{4-[2-(3-Benzyl-3H-imidazol-4-yl)-pyridin-4-yloxy]-naphthalen-1-yl}-ureido)-5-tert-butyl-2-methoxy-phenyl]-carbamic acid methyl ester;

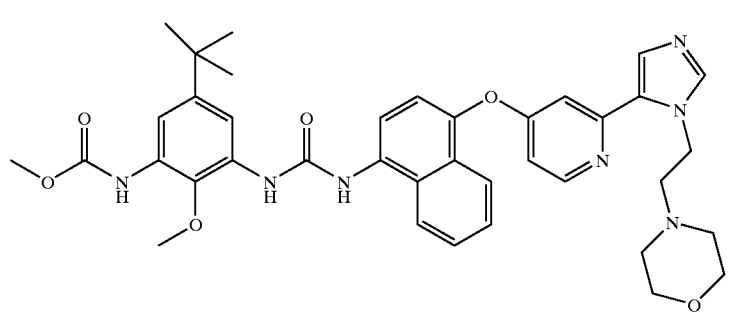

{5-tert-Butyl-2-methoxy-3-[3-(4-{2-[3-(2-morpholin-4-yl-ethyl)-3H-imidazol-4-yl]-pyridin-4-yloxy}-naphthalen-1-yl)-ureido]-phenyl}-carbamic acid methyl ester;

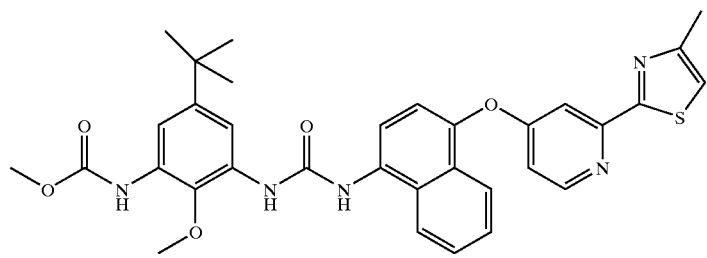

[5-tert-Butyl-2-methoxy-3-(3-{4-[2-(4-methyl-thiazol-2-yl)-pyridin-4-yloxy]-naphthalen-1-yl}-ureido)-phenyl]-carbamic acid methyl ester;

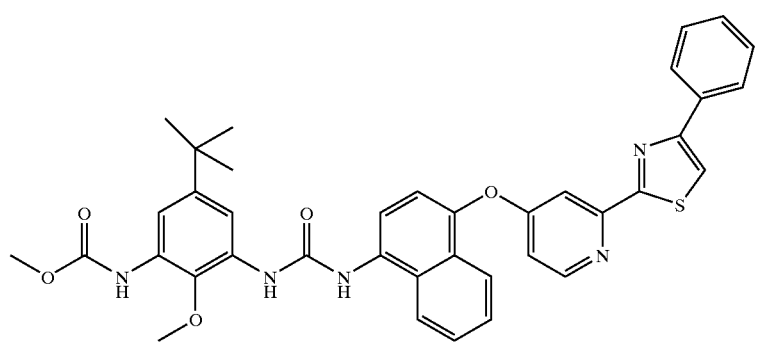

[5-tert-Butyl-2-methoxy-3-(3-{4-[2-(4-phenyl-thiazol-2-yl)-pyridin-4-yloxy]-naphthalen-1-yl}-ureido)-phenyl]-carbamic acid methyl ester;

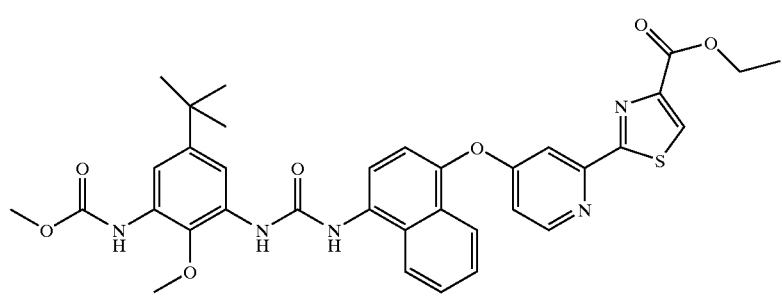

2-(4-{4-[3-(5-tert-Butyl-2-methoxy-3-methoxy-carbonylamino-phenyl)-ureido]-naphthalen-1-yloxy}-pyridin-2-yl)-thiazole-4-carboxylic acid ethyl ester;

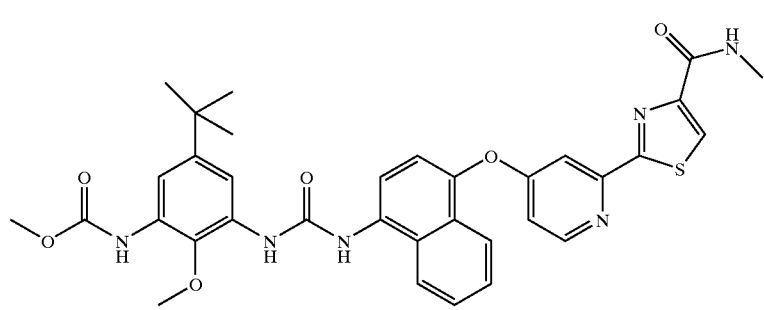

[5-tert-Butyl-2-methoxy-3-(3-{4-[2-(4-methyl-carbamoyl-thiazol-2-yl)-pyridin-4-yloxy]-naphthalen-1-yl}-ureido)-phenyl]-carbamic acid methyl ester;

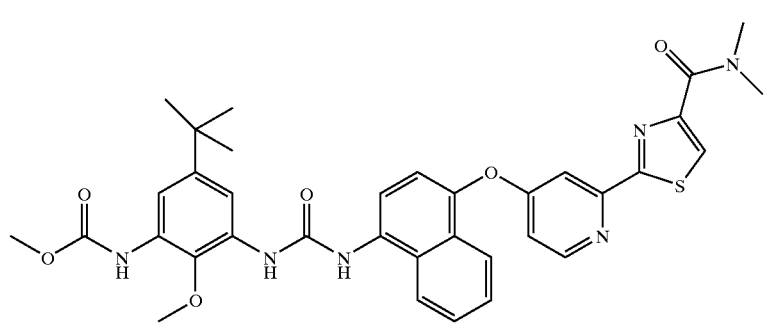

[5-tert-Butyl-3-(3-{4-[2-(4-dimethylcarbamoyl-thiazol-2-yl)-pyridin-4-yloxy]-naphthalen-1-yl}-ureido)-2-methoxy-phenyl]-carbamic acid methyl ester;

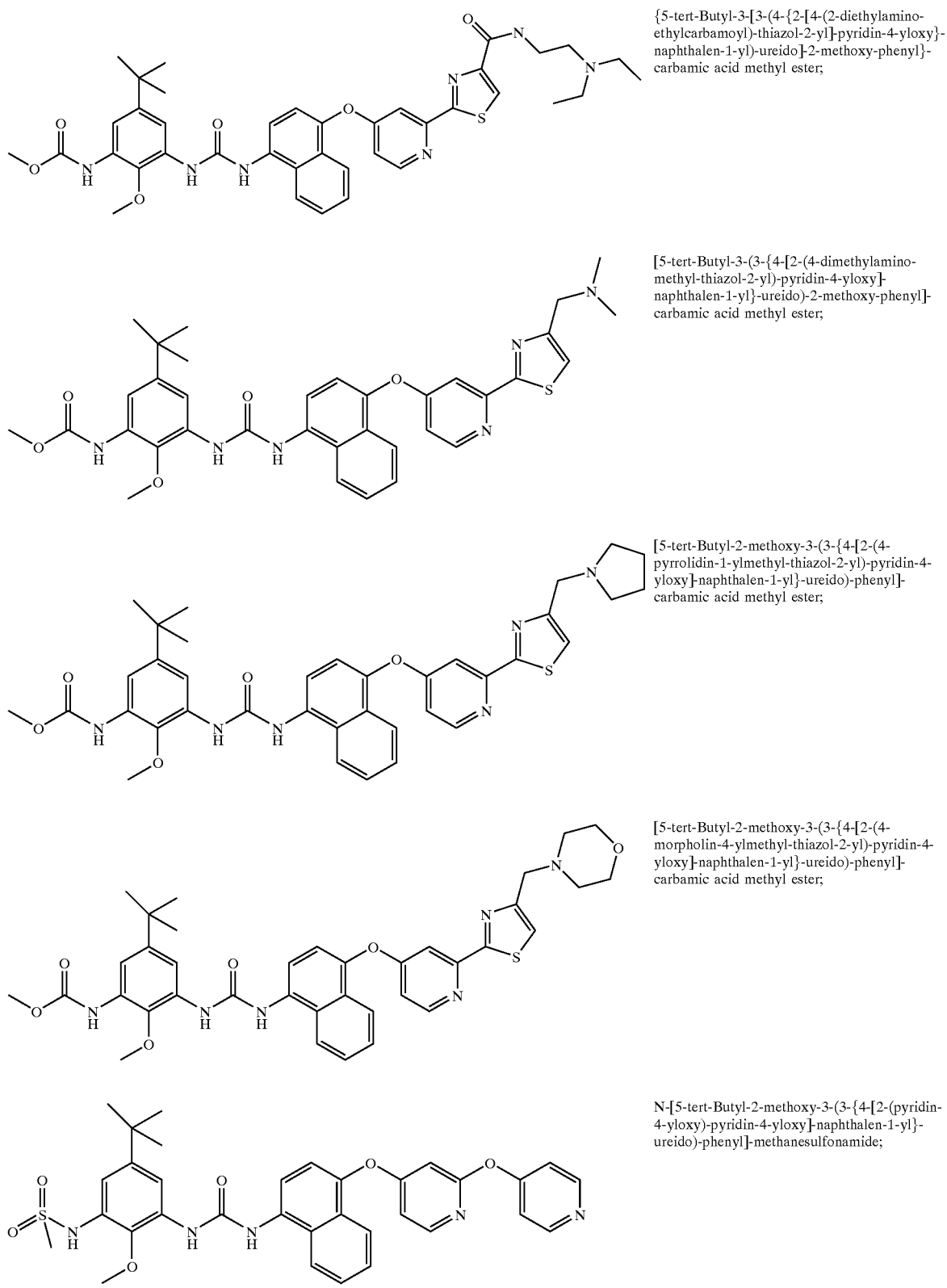

{5-tert-Butyl-3-[3-(4-{2-[4-(2-diethylamino-ethylcarbamoyl)-thiazol-2-yl]-pyridin-4-yloxy}-naphthalen-1-yl)-ureido]-2-methoxy-phenyl}-carbamic acid methyl ester;

[5-tert-Butyl-3-(3-{4-[2-(4-dimethylamino-methyl-thiazol-2-yl)-pyridin-4-yloxy]-naphthalen-1-yl}-ureido)-2-methoxy-phenyl]-carbamic acid methyl ester;

[5-tert-Butyl-2-methoxy-3-(3-{4-[2-(4-pyrrolidin-1-ylmethyl-thiazol-2-yl)-pyridin-4-yloxy]-naphthalen-1-yl}-ureido)-phenyl]-carbamic acid methyl ester;

[5-tert-Butyl-2-methoxy-3-(3-{4-[2-(4-morpholin-4-ylmethyl-thiazol-2-yl)-pyridin-4-yloxy]-naphthalen-1-yl}-ureido)-phenyl]-carbamic acid methyl ester;

N-[5-tert-Butyl-2-methoxy-3-(3-{4-[2-(pyridin-4-yloxy)-pyridin-4-yloxy]-naphthalen-1-yl}-ureido)-phenyl]-methanesulfonamide;

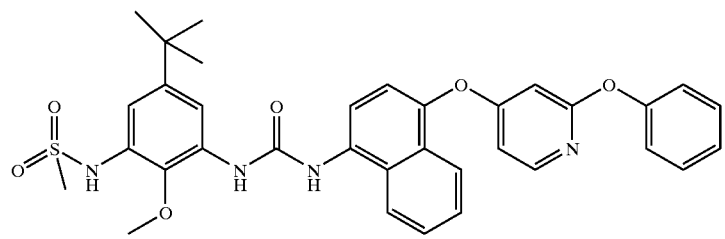

N-(5-tert-Butyl-2-methoxy-3-{3-[4-(2-phenoxy-pyridin-4-yloxy)-naphthalen-1-yl]-ureido}-phenyl)-methanesulfonamide;

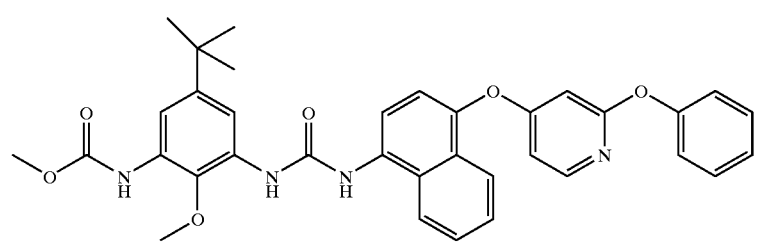

(5-tert-Butyl-2-methoxy-3-{3-[4-(2-phenoxy-pyridin-4-yloxy)-naphthalen-1-yl]-ureido}-phenyl)-carbamic acid methyl ester;

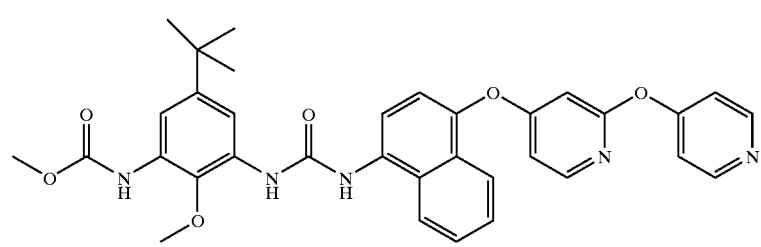

[5-tert-Butyl-2-methoxy-3-(3-{4-[2-(pyridin-4-yloxy)-pyridin-4-yloxy]-naphthalen-1-yl}-ureido)-phenyl]-carbamic acid methyl ester;

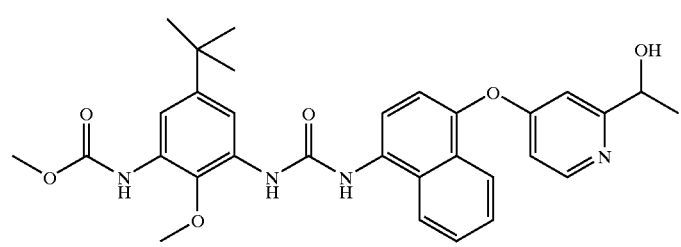

[5-tert-Butyl-3-(3-{4-[2-(1-hydroxy-ethyl)-pyridin-4-yloxy]-naphthalen-1-yl}-ureido)-2-methoxy-phenyl]-carbamic acid methyl ester;

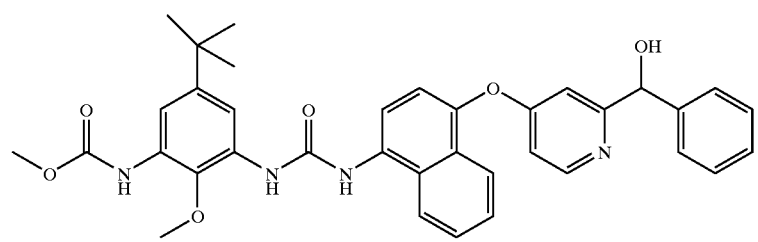

[5-tert-Butyl-3-(3-{4-[2-(hydroxy-phenyl-methyl)-pyridin-4-yloxy]-naphthalen-1-yl}-ureido)-2-methoxy-phenyl]-carbamic acid methyl ester;

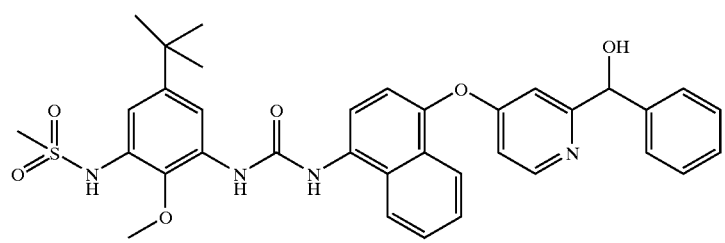

N-[5-tert-Butyl-3-(3-{4-[2-(hydroxy-phenyl-methyl)-pyridin-4-yloxy]-naphthalen-1-yl}-ureido)-2-methoxy-phenyl]-methane-sulfonamide;

-continued

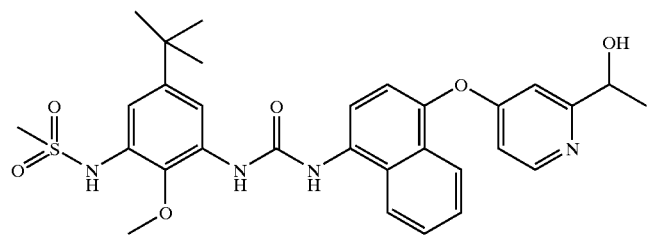

N-[5-tert-Butyl-3-(3-{4-[2-(1-hydroxy-ethyl)-pyridin-4-yloxy]-naphthalen-1-yl}-ureido)-2-methoxy-phenyl]-methanesulfonamide;

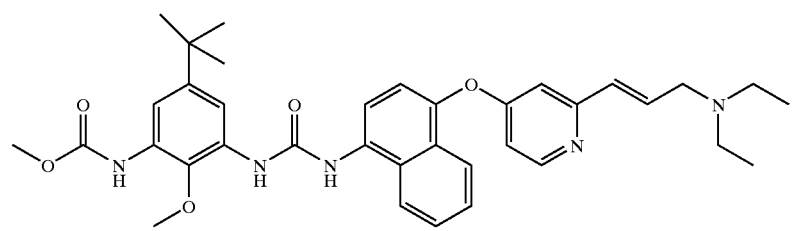

[5-tert-Butyl-3-(3-{4-[2-(3-diethylamino-propenyl)-pyridin-4-yloxy]-naphthalen-1-yl}-ureido)-2-methoxy-phenyl]-carbamic acid methyl ester;

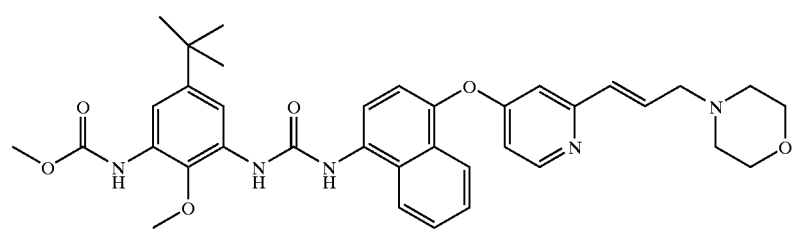

[5-tert-Butyl-2-methoxy-3-(3-{4-[2-(3-morpholin-4-yl-propenyl)-pyridin-4-yloxy]-naphthalen-1-yl}-ureido)-phenyl]-carbamic acid methyl ester;

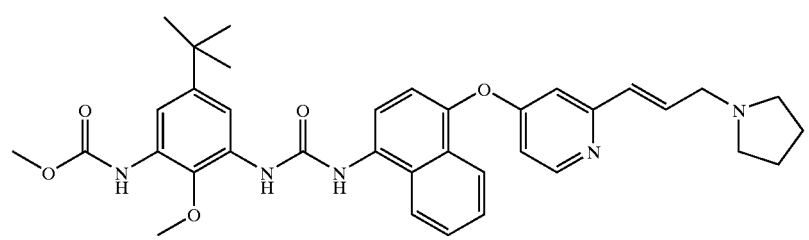

[5-tert-Butyl-2-methoxy-3-(3-{4-[2-(3-pyrrolidin-1-yl-propenyl)-pyridin-4-yloxy]-naphthalen-1-yl}-ureido)-phenyl]-carbamic acid methyl ester;

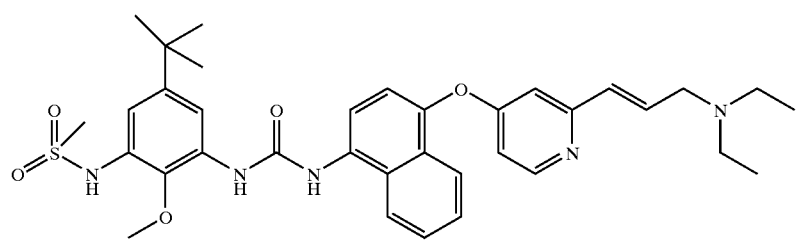

N-[5-tert-Butyl-3-(3-{4-[2-(3-diethylamino-propenyl)-pyridin-4-yloxy]-naphthalen-1-yl}-ureido)-2-methoxy-phenyl]-methane-sulfonamide;

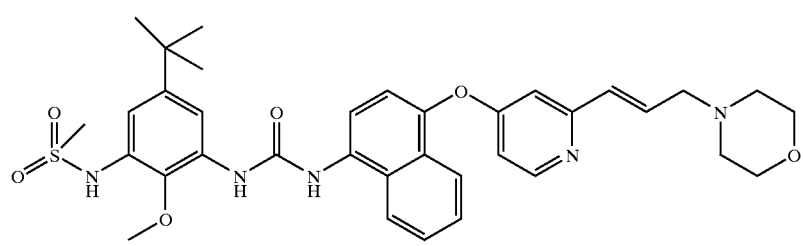

N-[5-tert-Butyl-2-methoxy-3-(3-{4-[2-(3-morpholin-4-yl-propenyl)-pyridin-4-yloxy]-naphthalen-1-yl}-ureido)-phenyl]-methane-sulfonamide;

-continued

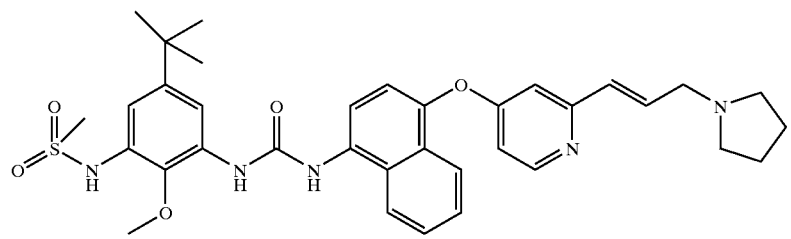

N-[5-tert-Butyl-2-methoxy-3-(3-{4-[2-(3-pyrrolidin-1-yl-propenyl)-pyridin-4-yloxy]-naphthalen-1-yl}-ureido)-phenyl]-methane-sulfonamide;

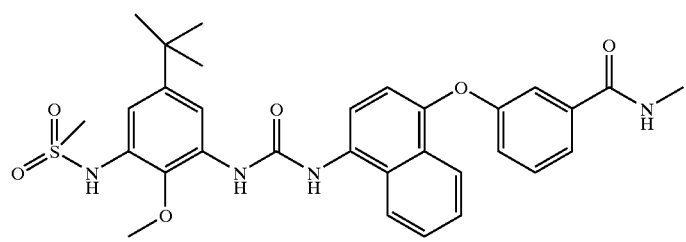

3-{4-[3-(5-tert-Butyl-3-methanesulfonylamino-2-methoxy-phenyl)-ureido]-naphthalen-1-yloxy}-N-methyl-benzamide;

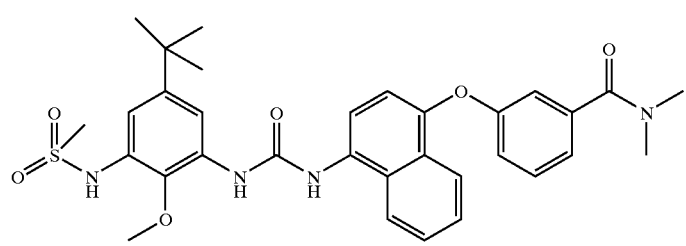

3-{4-[3-(5-tert-Butyl-3-methanesulfonylamino-2-methoxy-phenyl)-ureido]-naphthalen-1-yloxy}-N,N-dimethyl-benzamide;

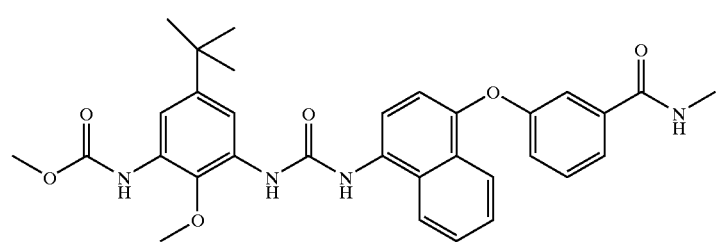

(5-tert-Butyl-2-methoxy-3-{3-[4-(3-methyl-carbamoyl-phenoxy)-naphthalen-1-yl]-ureido}-phenyl)-carbamic acid methyl ester;

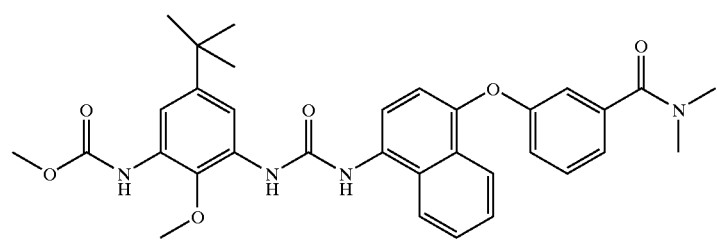

(5-tert-Butyl-3-{3-[4-(3-dimethylcarbamoyl-phenoxy)-naphthalen-1-yl]-ureido}-2-methoxy-phenyl)-carbamic acid methyl ester;

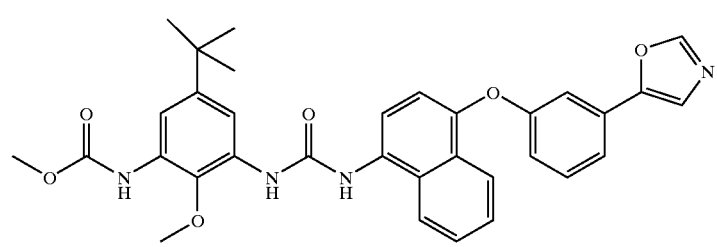

(5-tert-Butyl-2-methoxy-3-{3-[4-(3-oxazol-5-yl-phenoxy)-naphthalen-1-yl]-ureido}-phenyl)-carbamic acid methyl ester;

-continued

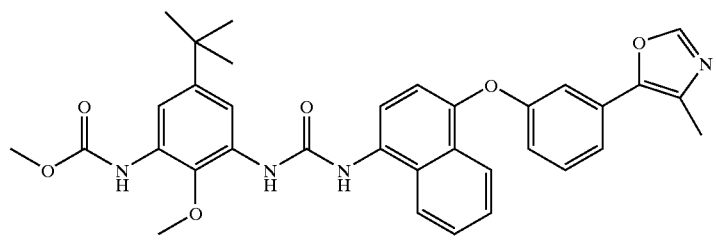

[5-tert-Butyl-2-methoxy-3-(3-{4-[3-(4-methyl-oxazol-5-yl)-phenoxy]-naphthalen-1-yl}-ureido)-phenyl]-carbamic acid methyl ester;

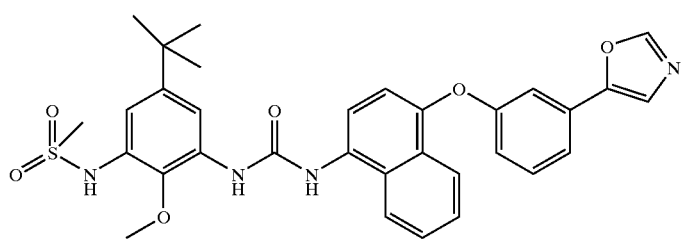

N-(5-tert-Butyl-2-methoxy-3-{3-[4-(3-oxazol-5-yl-phenoxy)-naphthalen-1-yl]-ureido}-phenyl)-methanesulfonamide;

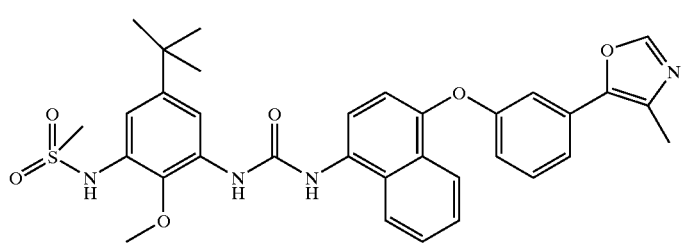

N-[5-tert-Butyl-2-methoxy-3-(3-{4-[3-(4-methyl-oxazol-5-yl)-phenoxy]-naphthalen-1-yl}-ureido)-phenyl]-methanesulfonamide;

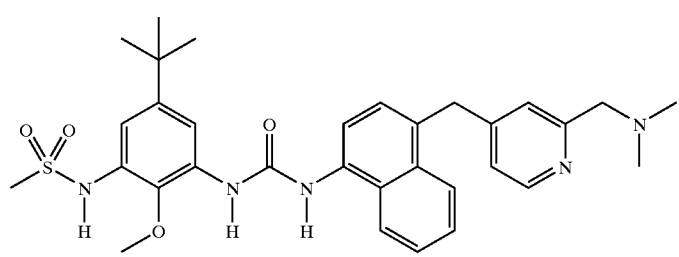

N-(5-tert-Butyl-3-{3-[4-(2-dimethylamino-methyl-pyridin-4-yl)-methyl)naphthalen-1-yl]-ureido}-2-methoxyphenyl]methanesulfonamide and

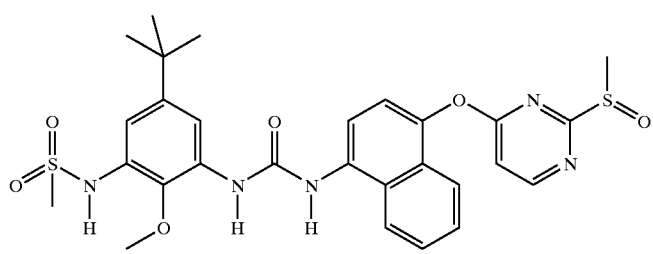

N-(5-tert-Butyl-3-{3-[4-(2-methanesulfinyl-pyrimidin-4-yloxy)-naphthalen-1-yl]-ureido}-2-methoxy-phenyl)-methanesulfonamide;

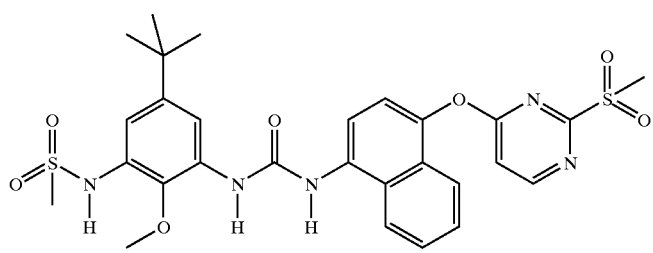

N-(5-tert-Butyl-3-{3-[4-(2-methanesulfonyl-pyrimidin-4-yloxy)-naphthalen-1-yl]-ureido}-2-methoxy-phenyl)-methanesulfonamide;

-continued

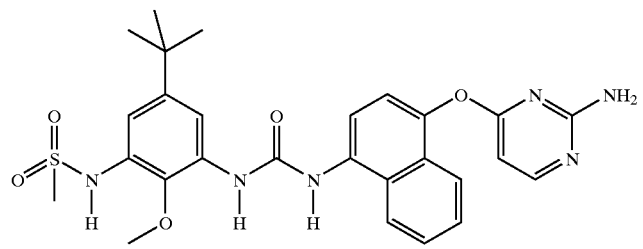
N-(3-{3-[4-(2-Amino-pyrimidin-4-yloxy)-naphthalen-1-yl]-ureido}-5-tert-butyl-2-methoxy-phenyl)-methanesulfonamide;

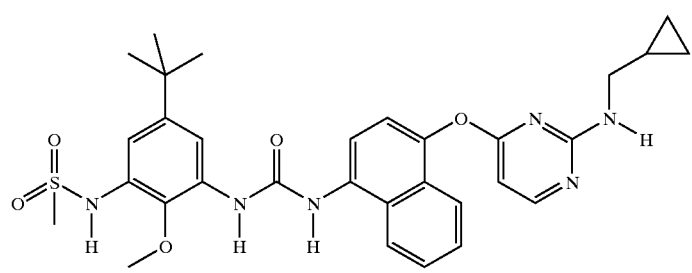
N-[5-tert-Butyl-3-(3-{4-[2-(cyclopropylmethyl-amino)-pyrimidin-4-yloxy]-naphthalen-1-yl}-ureido)-2-methoxy-phenyl]-methanesulfonamide;

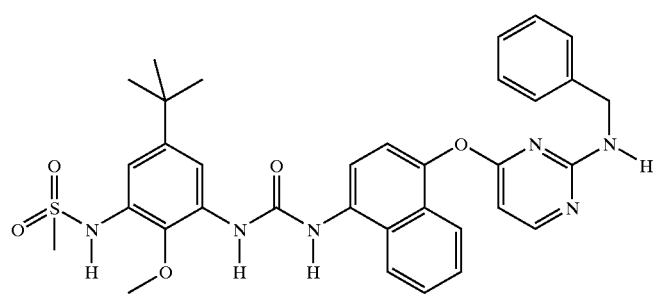
N-(3-{3-[4-(2-Benzylamino-pyrimidin-4-yloxy)-naphthalen-1-yl]-ureido}-5-tert-butyl-2-methoxy-phenyl)-methanesulfonamide;

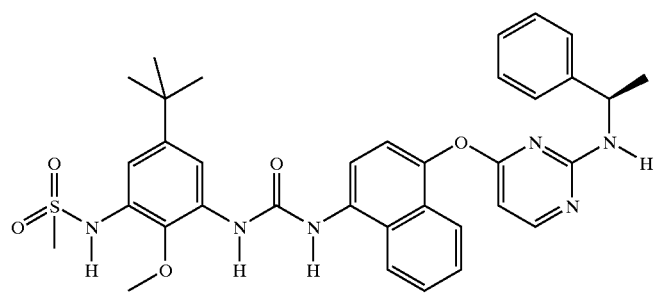
N-[5-tert-Butyl-2-methoxy-3-(3-{4-[2-(1-(R)-phenyl-ethylamino)-pyrimidin-4-yloxy]-naphthalen-1-yl}-ureido)-phenyl]-methanesulfonamide;

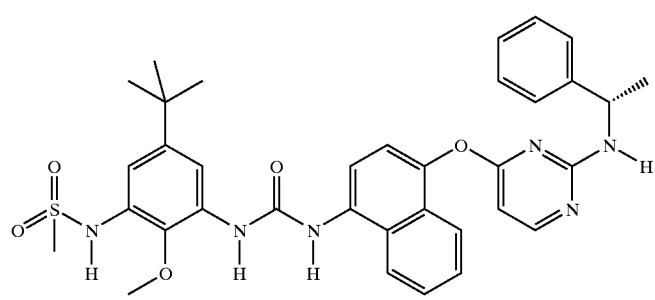
N-[5-tert-Butyl-2-methoxy-3-(3-{4-[2-(1-(S)-phenyl-ethylamino)-pyrimidin-4-yloxy]-naphthalen-1-yl}-ureido)-phenyl]-methanesulfonamide;

-continued

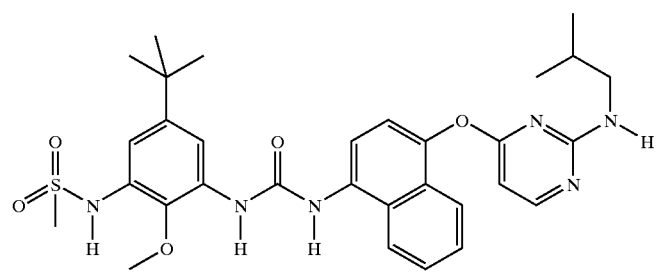
N-(5-tert-Butyl-3-{3-[4-(2-isobutylamino-pyrimidin-4-yloxy)-naphthalen-1-yl]-ureido}-2-methoxy-phenyl)-methanesulfonamide;

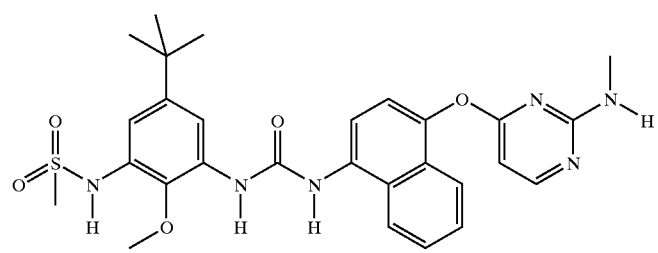
N-(5-tert-Butyl-2-methoxy-3-{3-[4-(2-methyl-amino-pyrimidin-4-yloxy)-naphthalen-1-yl]-ureido}-phenyl)-methanesulfonamide

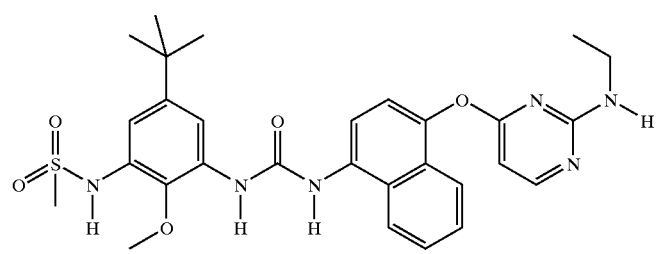
N-(5-tert-Butyl-3-{3-[4-(2-ethylamino-pyrimidin-4-yloxy)-naphthalen-1-yl]-ureido}-2-methoxy-phenyl)-methanesulfonamide;

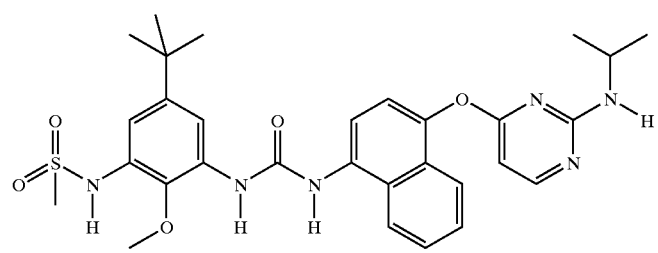
N-(5-tert-Butyl-3-{3-[4-(2-isopropylamino-pyrimidin-4-yloxy)-naphthalen-1-yl]-ureido}-2-methoxy-phenyl)-methanesulfonamide;

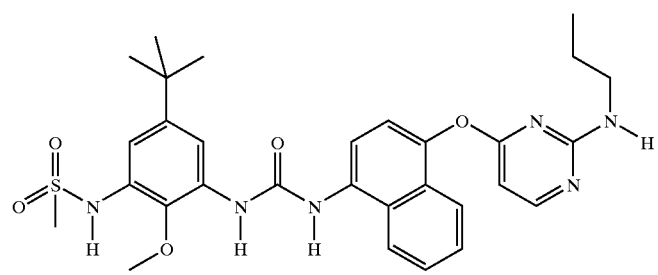
N-(5-tert-Butyl-2-methoxy-3-{3-[4-(2-propyl-amino-pyrimidin-4-yloxy)-naphthalen-1-yl]-ureido}-phenyl)-methanesulfonamide

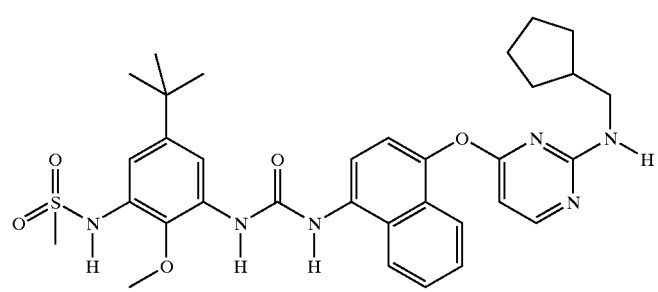
N-[5-tert-Butyl-3-(3-{4-[2-(cyclopentylmethyl-amino)-pyrimidin-4-yloxy]-naphthalen-1-yl}-ureido)-2-methoxy-phenyl]-methanesulfonamide;

-continued

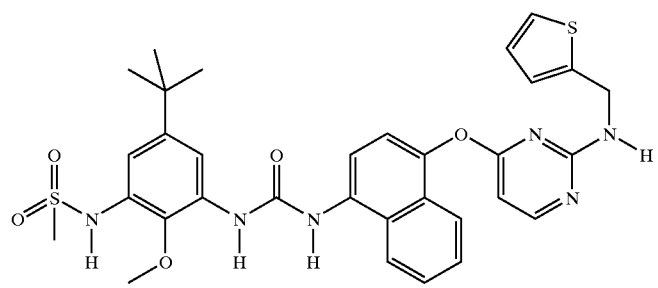

N-{5-tert-Butyl-2-methoxy-3-[3-(4-{2-[(thiophen-2-ylmethyl)-amino]-pyrimidin-4-yloxy}-naphthalen-1-yl)-ureido]-phenyl}-methanesulfonamide;

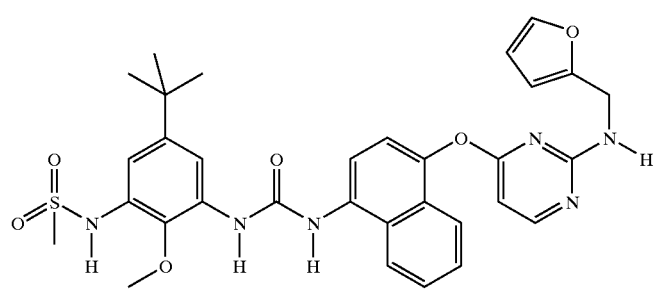

N-{5-tert-Butyl-3-[3-(4-{2-[(furan-2-ylmethyl)-amino]-pyrimidin-4-yloxy}-naphthalen-1-yl)-ureido]-2-methoxy-phenyl}-methanesulfonamide;

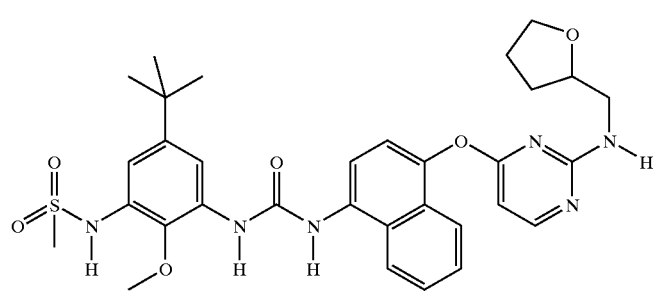

N-{5-tert-Butyl-2-methoxy-3-[3-(4-{2-[(tetrahydro-furan-2-ylmethyl)-amino]-pyrimidin-4-yloxy}-naphthalen-1-yl)-ureido]-phenyl}-methanesulfonamide;

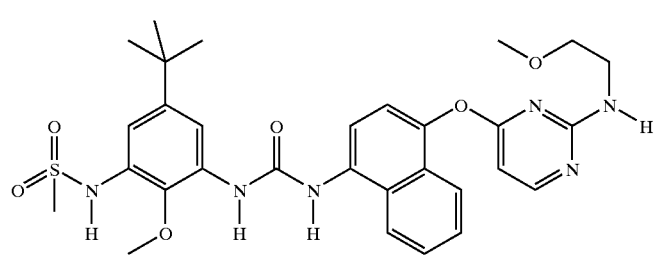

N-[5-tert-Butyl-2-methoxy-3-(3-{4-[2-(2-methoxy-ethylamino)-pyrimidin-4-yloxy]-naphthalen-1-yl}-ureido)-phenyl]-methanesulfonamide;

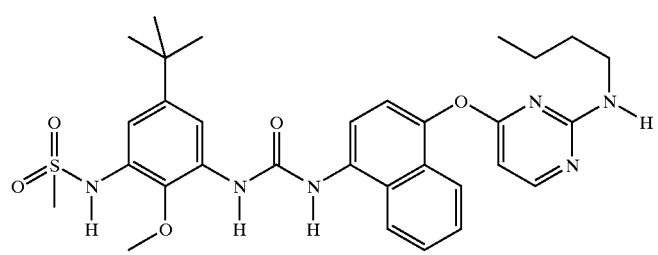

N-(5-tert-Butyl-3-{3-[4-(2-butylamino-pyrimidin-4-yloxy)-naphthalen-1-yl]-ureido}-2-methoxy-phenyl)-methanesulfonamide;

-continued

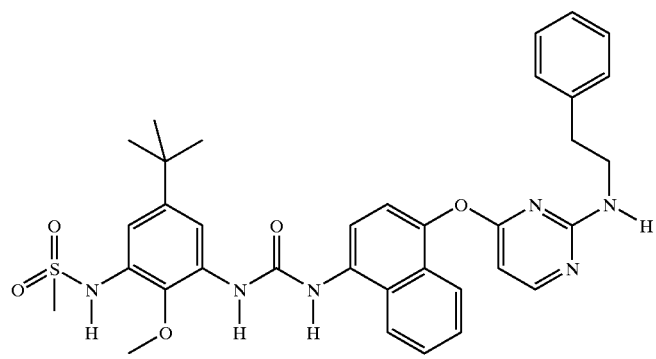

N-(5-tert-Butyl-2-methoxy-3-{3-[4-(2-phenethylamino-pyrimidin-4-yloxy)-naphthalen-1-yl]-ureido}-phenyl)-methane-sulfonamide;

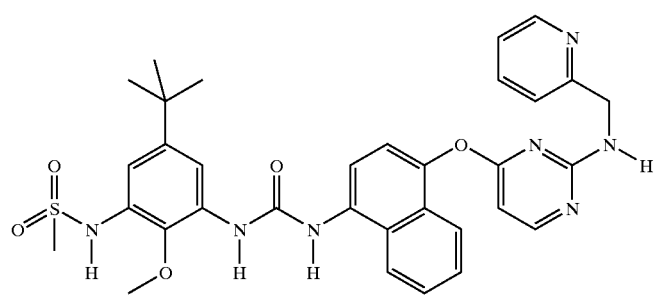

N-{5-tert-Butyl-2-methoxy-3-[3-(4-{2-[(pyridin-2-ylmethyl)-amino]-pyrimidin-4-yloxy}-naphthalen-1-yl)-ureido]-phenyl}-methanesulfonamide;

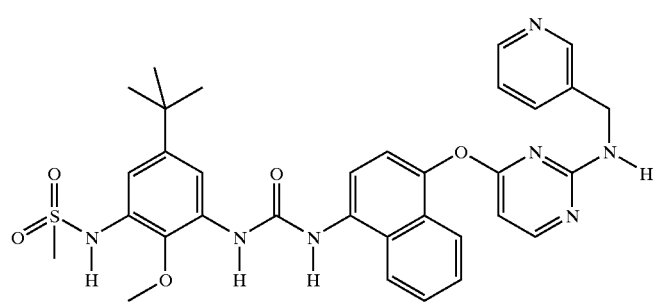

N-{5-tert-Butyl-2-methoxy-3-[3-(4-{2-[(pyridin-3-ylmethyl)-amino]-pyrimidin-4-yloxy}-naphthalen-1-yl)-ureido]-phenyl}-methanesulfonamide;

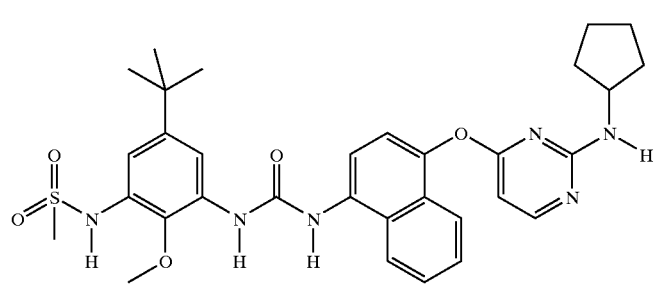

N-(5-tert-Butyl-3-{3-[4-(2-cyclopentyl-amino-pyrimidin-4-yloxy)-naphthalen-1-yl]-ureido}-2-methoxy-phenyl)-methanesulfonamide;

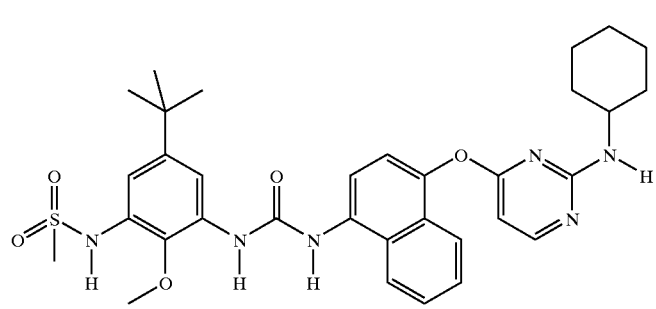

N-(5-tert-Butyl-3-{3-[4-(2-cyclohexylamino-pyrimidin-4-yloxy)-naphthalen-1-yl]-ureido}-2-methoxy-phenyl)-methanesulfonamide;

-continued

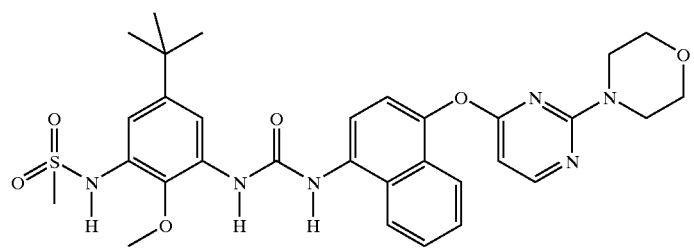

N-(5-tert-Butyl-2-methoxy-3-{3-{4-(2-morpholin-4-yl-pyrimidin-4-yloxy)-naphthalen-1-yl]-ureido}-phenyl)-methanesulfonamide;

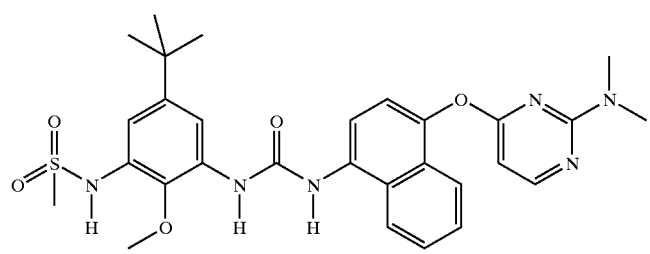

N-(5-tert-Butyl-3-{3-[4-(2-dimethylamino-pyrimidin-4-yloxy)-naphthalen-1-yl]-ureido}-2-methoxy-phenyl)-methanesulfonamide;

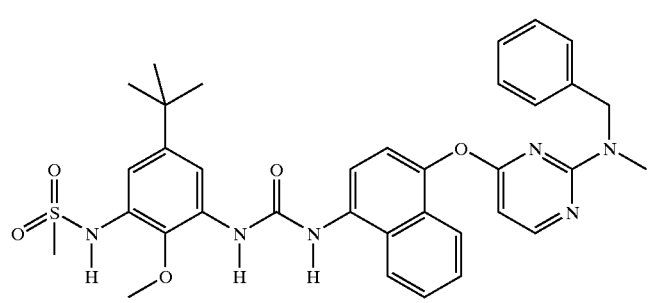

N-[3-(3-{4-[2-(Benzyl-methyl-amino)-pyrimidin-4-yloxy]-naphthalen-1-yl}-ureido)-5-tert-butyl-2-methoxy-phenyl]-methanesulfonamide

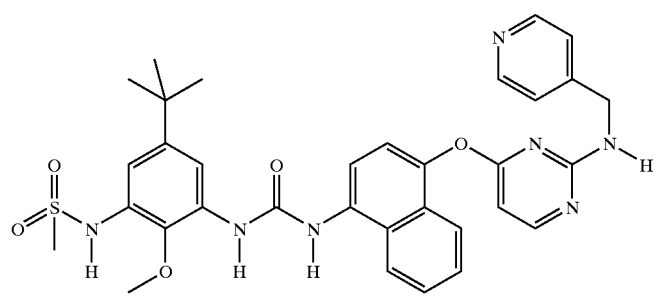

N-{5-tert-Butyl-2-methoxy-3-[3-(4-{2-[(pyridin-4-ylmethyl)-amino]-pyrimidin-4-yloxy}-naphthalen-1-yl)-ureido]-phenyl}-methanesulfonamide

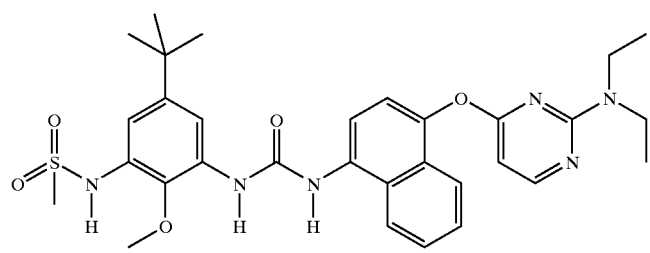

N-(5-tert-Butyl-3-{3-[4-(2-diethylamino-pyrimidin-4-yloxy)-naphthalen-1-yl]-ureido}-2-methoxy-phenyl)-methanesulfonamide;

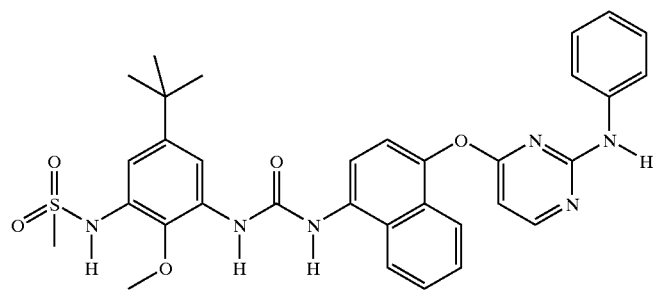

N-(5-tert-Butyl-2-methoxy-3-{3-[4-(2-phenyl-amino-pyrimidin-4-yloxy)-naphthalen-1-yl]-ureido}-phenyl)-methanesulfonamide;

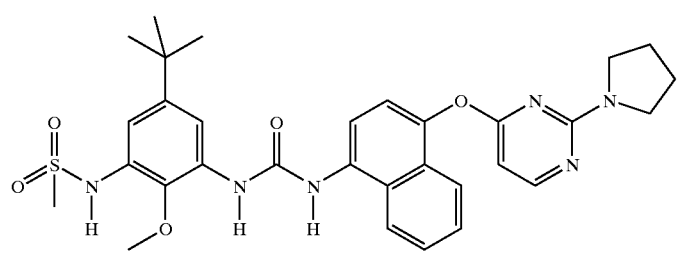

N-(5-tert-Butyl-2-methoxy-3-{3-[4-(2-pyrrolidin-1-yl-pyrimidin-4-yloxy)-naphthalen-1-yl]-ureido}-phenyl)-methanesulfonamide;

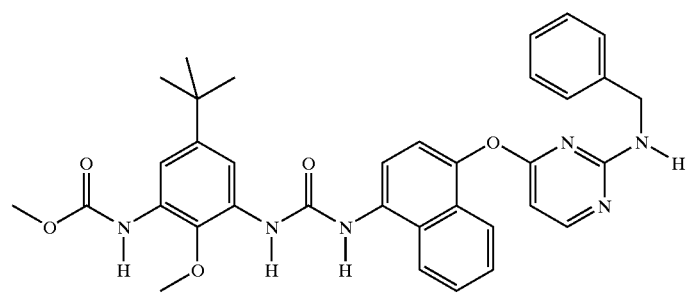

(3-{3-[4-(2-Benzylamino-pyrimidin-4-yloxy)-naphthalen-1-yl]-ureido}-5-tert-butyl-2-methoxy-phenyl)-carbamic acid methyl ester;

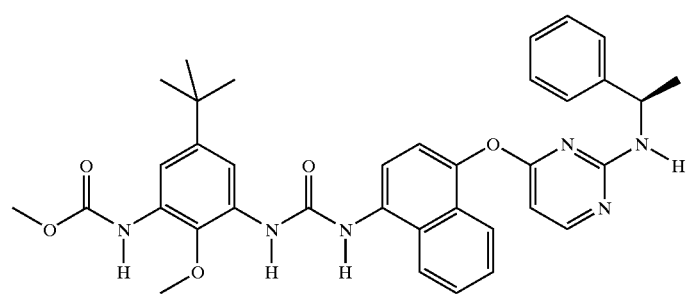

[5-tert-Butyl-2-methoxy-3-(3-{4-[2-(1-(R)-phenyl-ethylamino)-pyrimidin-4-yloxy]-naphthalen-1-yl}-ureido)-phenyl]-carbamic acid methyl ester;

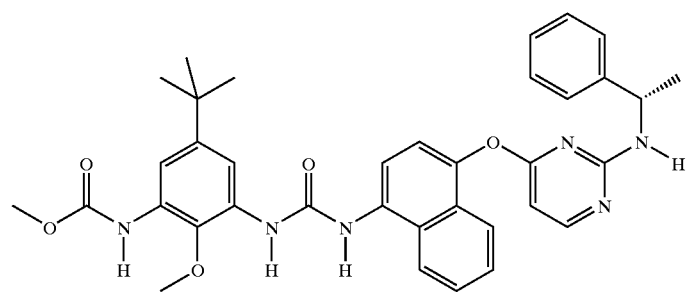

[5-tert-Butyl-2-methoxy-3-(3-{4-[2-(1-(S)-phenyl-ethylamino)-pyrimidin-4-yloxy]-naphthalen-1-yl}-ureido)-phenyl]-carbamic acid methyl ester;

-continued

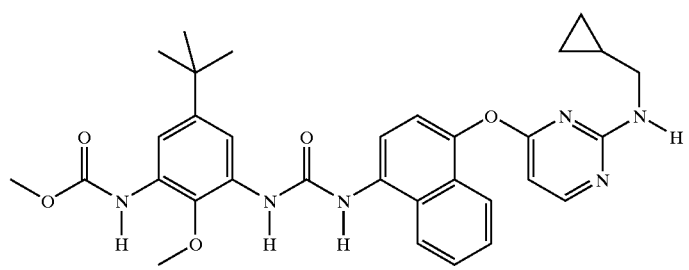

[5-tert-Butyl-3-(3-{4-[2-(cyclopropylmethyl-amino)-pyrimidin-4-yloxy]-naphthalen-1-yl}-ureido)-2-methoxy-phenyl]-carbamic acid methyl ester;

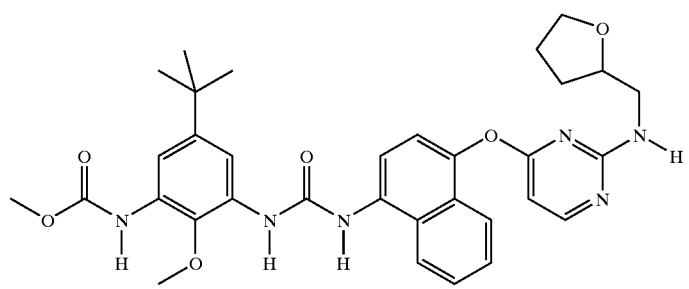

{5-tert-Butyl-2-methoxy-3-[3-(4-{2-[(tetra-hydro-furan-2-ylmethyl)-amino]-pyrimidin-4-yloxy}-naphthalen-1-yl)-ureido]-phenyl}-carbamic acid methyl ester;

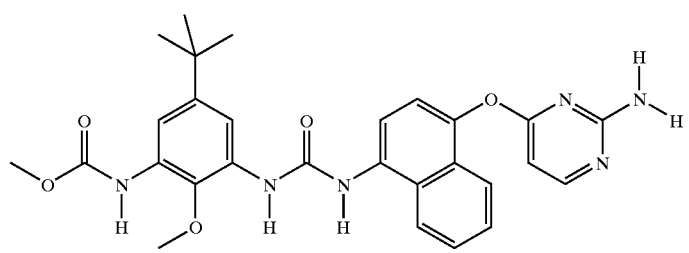

(3-{3-[4-(2-Amino-pyrimidin-4-yloxy)-naphthalen-1-yl]-ureido}-5-tert-butyl-2-methoxy-phenyl)-carbamic acid methyl ester;

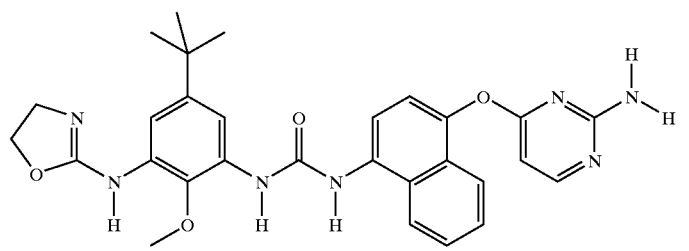

1-[4-(2-Amino-pyrimidin-4-yloxy)-naphthalen-1-yl]-3-[5-tert-butyl-3-(4,5-dihydro-oxazol-2-ylamino)-2-methoxy-phenyl]-urea;

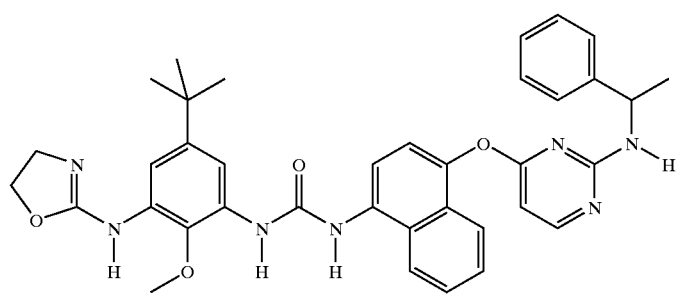

1-[5-tert-Butyl-3-(4,5-dihydro-oxazol-2-ylamino)-2-methoxy-phenyl]-3-{4-[2-(1-phenyl-ethylamino)-pyrimidin-4-yloxy]-naphthalen-1-yl}-urea;

-continued

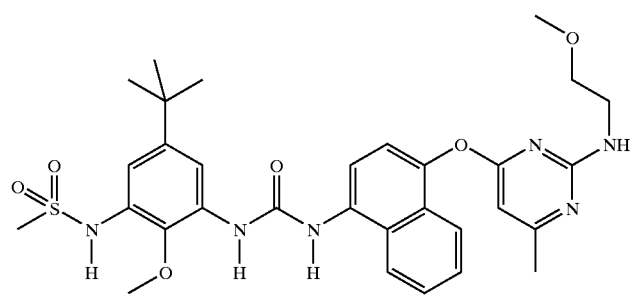

N-[5-tert-Butyl-2-methoxy-3-(3-{4-[2-(2-methoxy-ethylamino)-6-methyl-pyrimidin-4-yloxy]-naphthalen-1-yl}-ureido)-phenyl]-methanesulfonamide;

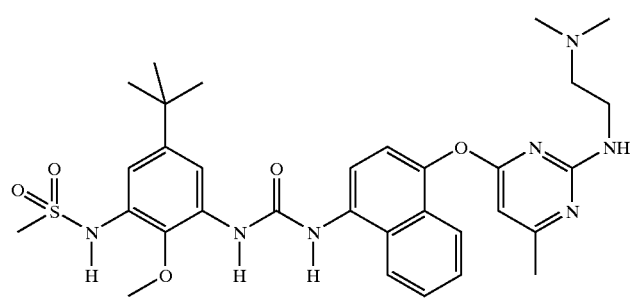

N-[5-tert-Butyl-3-(3-{4-[2-(2-dimethylamino-ethylamino)-6-methyl-pyrimidin-4-yloxy]-naphthalen-1-yl}-ureido)-2-methoxy-phenyl]-methanesulfonamide;

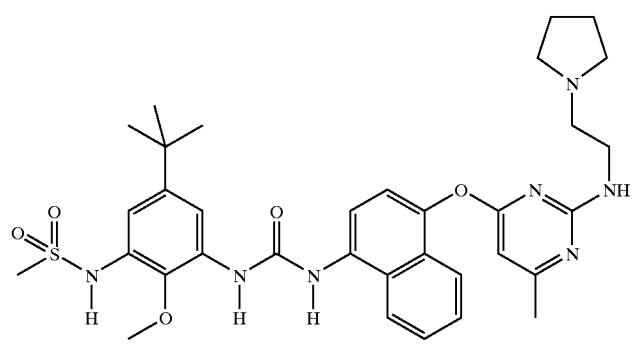

N-[5-tert-Butyl-2-methoxy-3-(3-{4-[6-methyl-2-(2-pyrrolidin-1-yl-ethylamino)-pyrimidin-4-yloxy]-naphthalen-1-yl}-ureido)-phenyl]-methanesulfonamide;

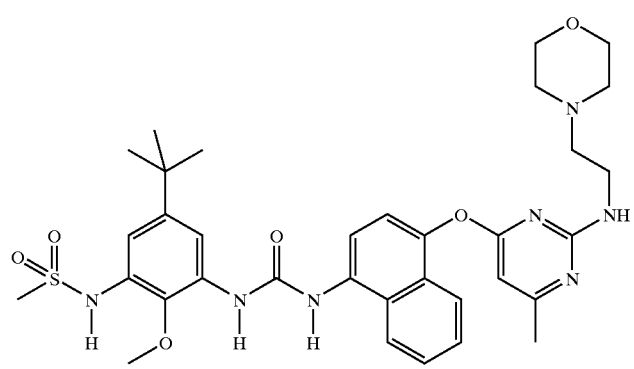

N-[5-tert-Butyl-2-methoxy-3-(3-{4-[6-methyl-2-(2-morpholin-4-yl-ethylamino)-pyrimidin-4-yloxy]-naphthalen-1-yl}-ureido)-phenyl]-methanesulfonamide;

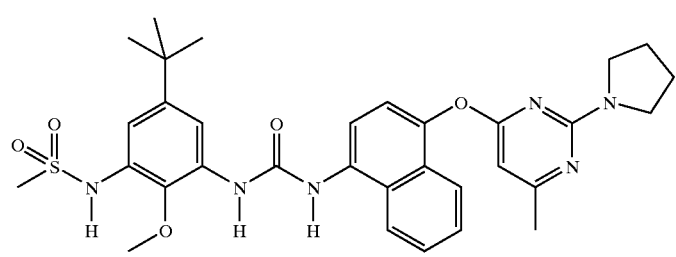

N-(5-tert-Butyl-2-methoxy-3-{3-[4-(6-methyl-2-pyrrolidin-1-yl-pyrimidin-4-yloxy)-naphthalen-1-yl]-ureido}-phenyl)-methanesulfonamide;

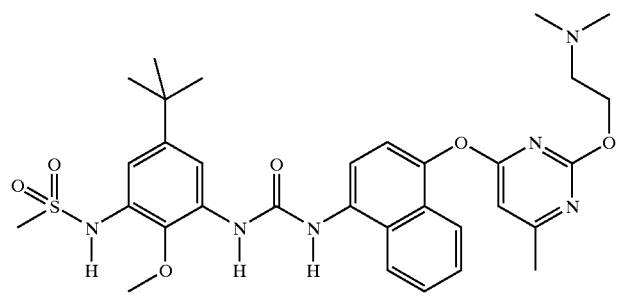

N-[5-tert-Butyl-3-(3-{4-[2-(2-dimethylamino-ethoxy)-6-methyl-pyrimidin-4-yloxy]-naphthalen-1-yl}-ureido)-2-methoxy-phenyl]-methanesulfonamide;

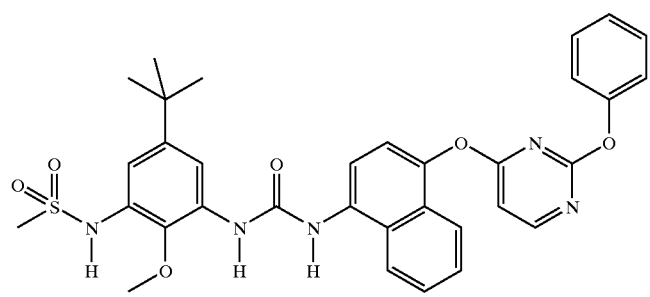

N-(5-tert-Butyl-2-methoxy-3-{3-[4-(2-phenoxy-pyrimidin-4-yloxy)-naphthalen-1-yl]-ureido}-phenyl)-methanesulfonamide;

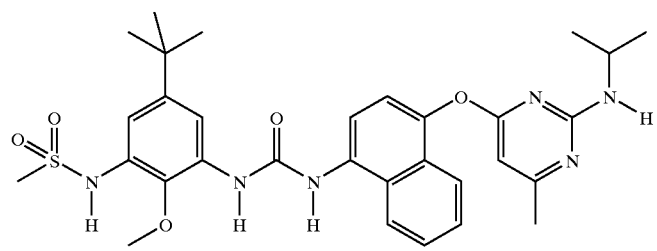

N-(5-tert-Butyl-3-{3-[4-(2-isopropylamino-6-methyl-pyrimidin-4-yloxy)-naphthalen-1-yl]-ureido}-2-methoxy-phenyl)-methanesulfonamide;

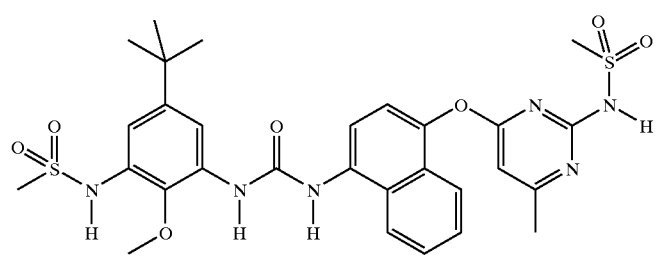

N-(5-tert-Butyl-3-{3-[4-(2-methanesulfonyl-amino-6-methyl-pyrimidin-4-yloxy)-naphthalen-1-yl]-ureido}-2-methoxy-phenyl)-methanesulfonamide;

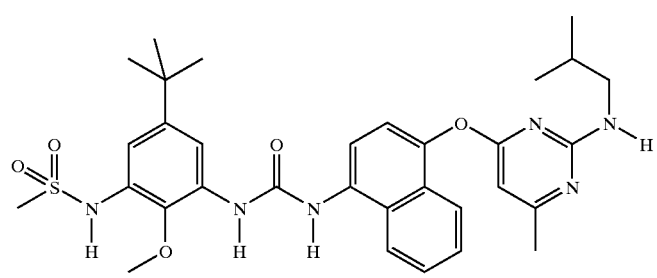

N-(5-tert-Butyl-3-{3-[4-(2-isobutylamino-6-methyl-pyrimidin-4-yloxy)-naphthalen-1-yl]-ureido}-2-methoxy-phenyl)-methanesulfonamide;

-continued

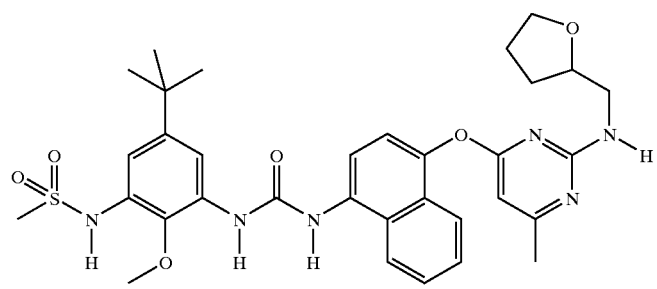

N-{5-tert-Butyl-2-methoxy-3-[3-(4-{6-methyl-2-[(tetrahydro-furan-2-ylmethyl)-amino]-pyrimidin-4-yloxy}-naphthalen-1-yl)-ureido]-phenyl}-methanesulfonamide;

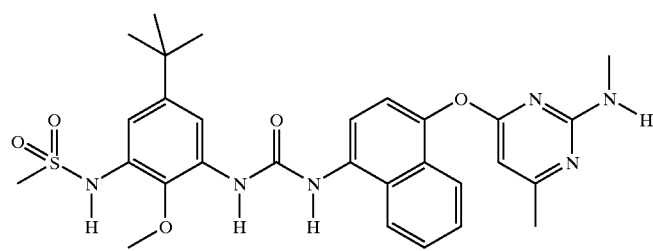

N-(5-tert-Butyl-2-methoxy-3-{3-[4-(6-methyl-2-methylamino-pyrimidin-4-yloxy)-naphthalen-1-yl]-ureido}-phenyl)-methanesulfonamide;

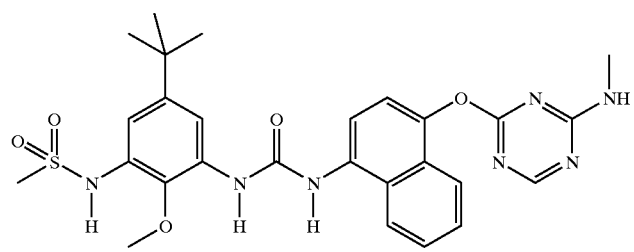

N-(5-tert-Butyl-2-methoxy-3-{3-[4-(4-methylamino-[1,3,5]triazin-2-yloxy)-naphthalen-1-yl]-ureido}-phenyl)-methanesulfonamide;

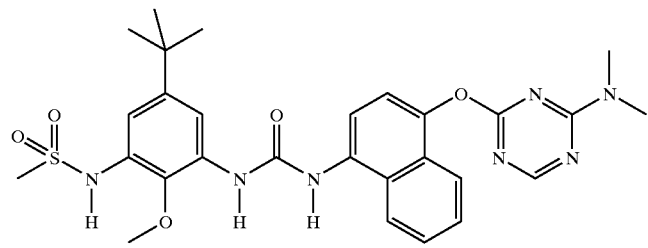

N-(5-tert-Butyl-3-{3-[4-(4-dimethylamino-[1,3,5]triazin-2-yloxy)-naphthalen-1-yl]-ureido}-2-methoxy-phenyl)-methanesulfonamide;

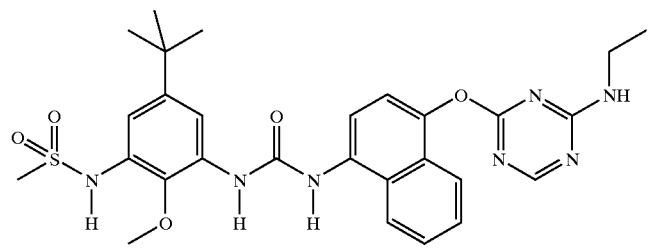

N-(5-tert-Butyl-3-{3-[4-(4-ethylamino-[1,3,5]triazin-2-yloxy)-naphthalen-1-yl]-ureido}-2-methoxy-phenyl)-methanesulfonamide;

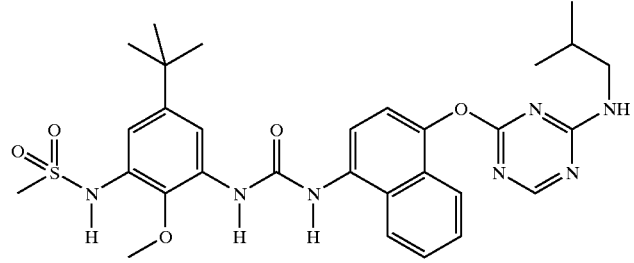

N-(5-tert-Butyl-3-{3-[4-(4-isobutylamino-[1,3,5]triazin-2-yloxy)-naphthalen-1-yl]-ureido}-2-methoxy-phenyl)-methanesulfonamide;

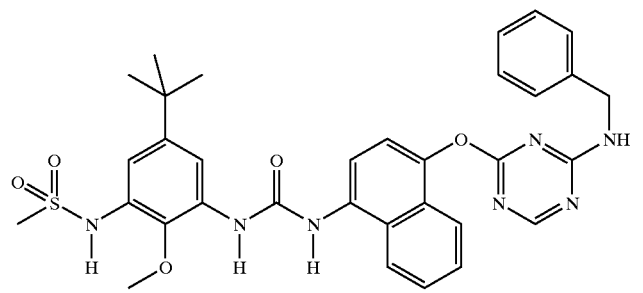

N-(3-{3-[4-(4-Benzylamino-[1,3,5]triazin-2-yloxy)-naphthalen-1-yl]-ureido}-5-tert-butyl-2-methoxy-phenyl)-methanesulfonamide;

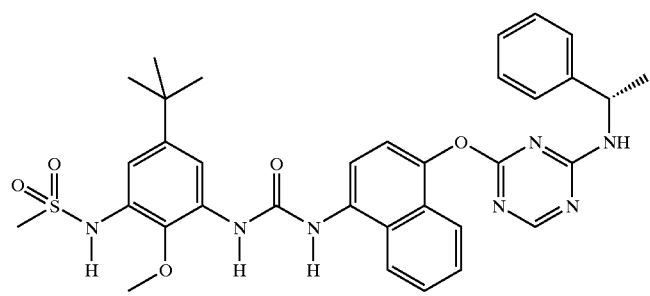

(R)-N-[5-tert-Butyl-2-methoxy-3-(3-{4-[4-(1-phenyl-ethylamino)-[1,3,5]triazin-2-yloxy]-naphthalen-1-yl}-ureido)-phenyl]-methanesulfonamide;

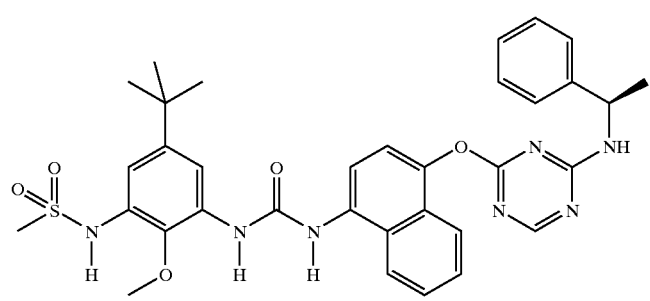

(S)-N-[5-tert-Butyl-2-methoxy-3-(3-{4-[4-(1-phenyl-ethylamino)-[1,3,5]triazin-2-yloxy]-naphthalen-1-yl}-ureido)-phenyl]-methanesulfonamide;

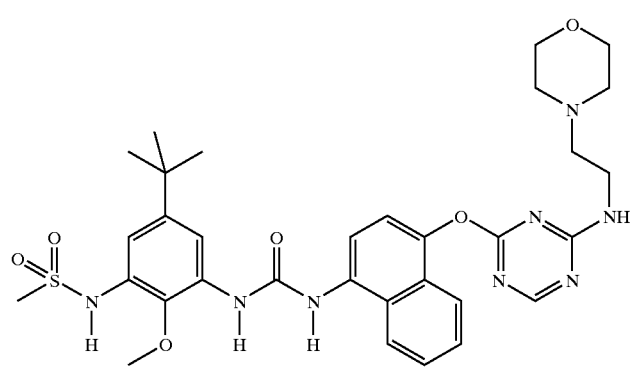

N-[5-tert-Butyl-2-methoxy-3-(3-{4-[4-(2-morpholin-4-yl-ethylamino)-[1,3,5]triazin-2-yloxy]-naphthalen-1-yl}-ureido)-phenyl]-methanesulfonamide;

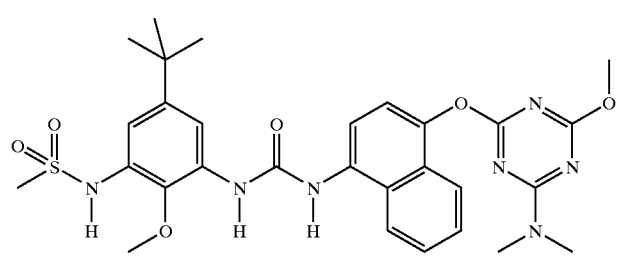

N-(5-tert-Butyl-3-{3-[4-(4-dimethylamino-6-methoxy-[1,3,5]triazin-2-yloxy)-naphthalen-1-yl]-ureido}-2-methoxy-phenyl)-methanesulfonamide;

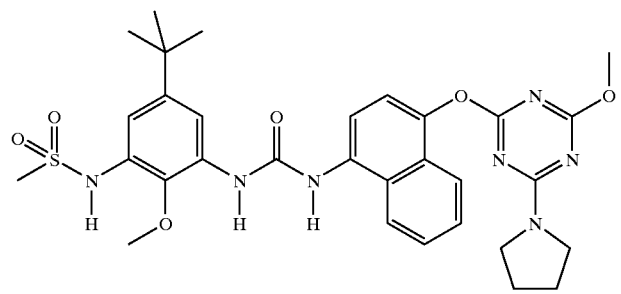

N-(5-tert-Butyl-2-methoxy-3-{3-[4-(4-methoxy-6-pyrrolidin-1-yl-[1,3,5]triazin-2-yloxy)-naphthalen-1-yl]-ureido}-phenyl)-methanesulfonamide;

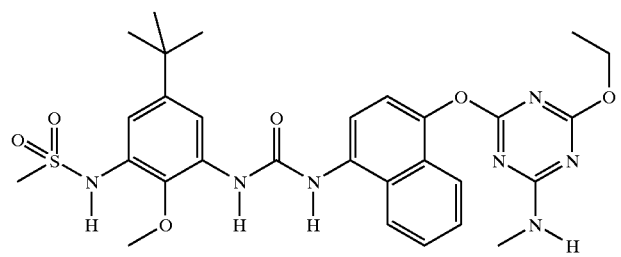

N-(5-tert-Butyl-3-{3-[4-(4-ethoxy-6-methyl-amino-[1,3,5]triazin-2-yloxy)-naphthalen-1-yl]-ureido}-2-methoxy-phenyl)-methanesulfonamide;

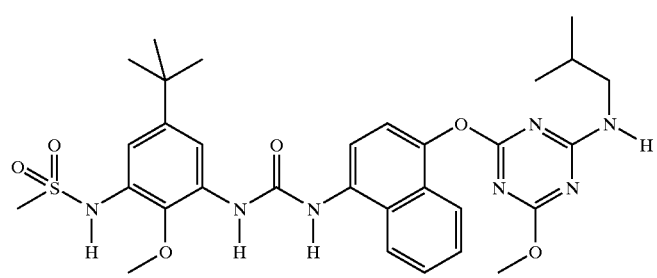

N-(5-tert-Butyl-3-{3-[4-(4-isobutylamino-6-methoxy-[1,3,5]triazin-2-yloxy)-naphthalen-1-yl]-ureido}-2-methoxy-phenyl)-methanesulfonamide;

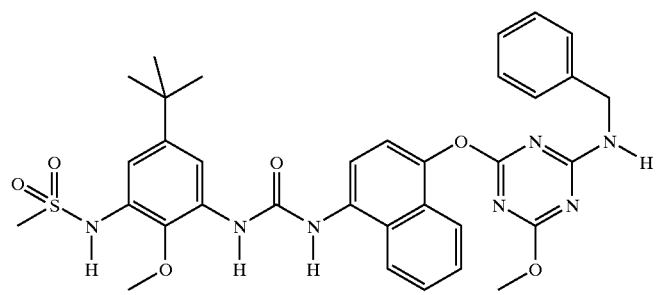

N-(3-{3-[4-(4-Benzylamino-6-methoxy-[1,3,5]-triazin-2-yloxy)-naphthalen-1-yl]-ureido}-5-tert-butyl-2-methoxy-phenyl)-methanesulfonamide;

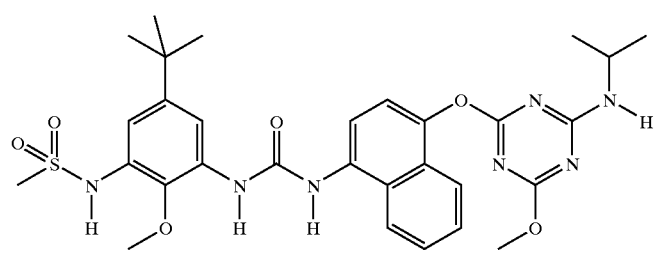

N-(5-tert-Butyl-3-{3-[4-(4-isopropylamino-6-methoxy-[1,3,5]triazin-2-yloxy)-naphthalen-1-yl]-ureido}-2-methoxy-phenyl)-methanesulfonamide;

-continued

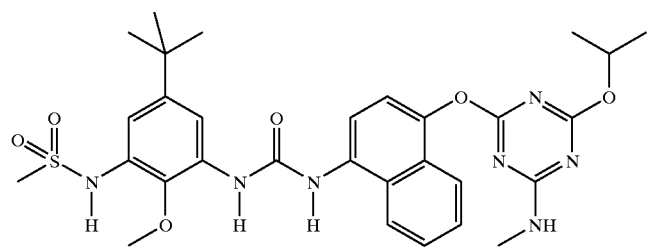

N-(5-tert-Butyl-3-{3-[4-(4-isopropoxy-6-methylamino-[1,3,5]triazin-2-yloxy)-naphthalen-1-yl]-ureido}-2-methoxy-phenyl)-methanesulfonamide;

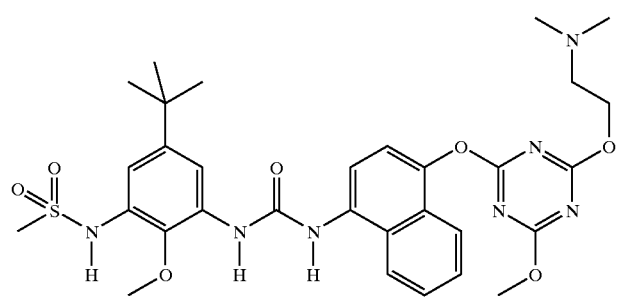

N-[5-tert-Butyl-3-(3-{4-[4-(2-dimethylamino-ethoxy)-6-methoxy-[1,3,5]triazin-2-yloxy]-naphthalen-1-yl}-ureido)-2-methoxy-phenyl]-methanesulfonamide;

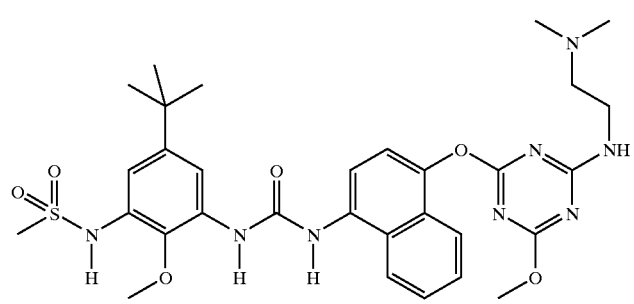

N-[5-tert-Butyl-3-(3-{4-[4-(2-dimethylamino-ethylamino)-6-methoxy-[1,3,5]triazin-2-yloxy]-naphthalen-1-yl}-ureido)-2-methoxy-phenyl]-methanesulfonamide;

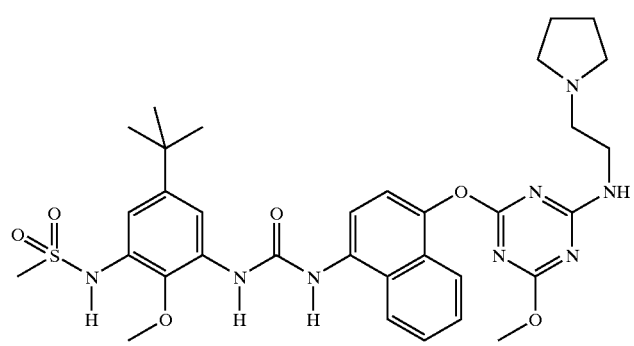

N-[5-tert-Butyl-2-methoxy-3-(3-{4-[4-methoxy-6-(2-pyrrolidin-1-yl-ethylamino)-[1,3,5]triazin-2-yloxy]-naphthalen-1-yl}-ureido)-phenyl]-methanesulfonamide;

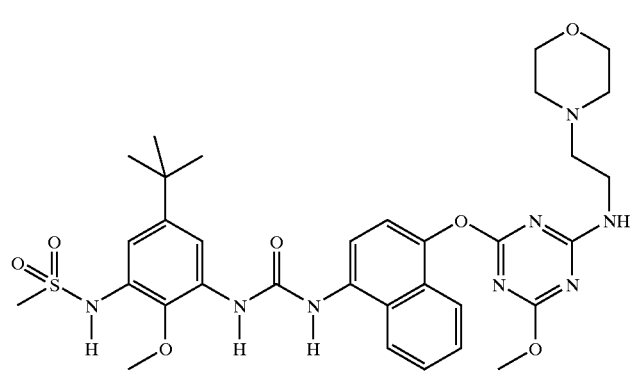

N-[5-tert-Butyl-2-methoxy-3-(3-{4-[4-methoxy-6-(2-morpholin-4-yl-ethylamino)-[1,3,5]triazin-2-yloxy]-naphthalen-1-yl}-ureido)-phenyl]-methanesulfonamide;

-continued

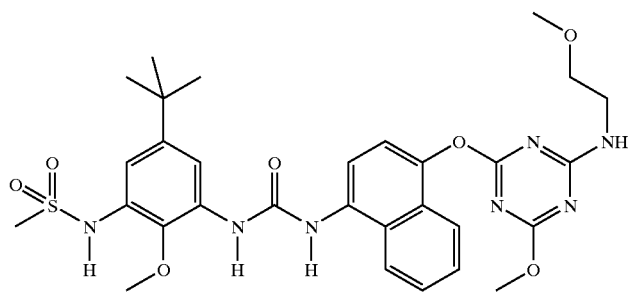

N-[5-tert-Butyl-2-methoxy-3-(3-{4-[4-methoxy-6-(2-methoxy-ethylamino)-[1,3,5]-triazin-2-yloxy]-naphthalen-1-yl}-ureido)-phenyl]-methanesulfonamide and the pharmaceutically acceptable derivatives thereof.

In a third subgeneric aspect of the invention there is provided compounds of the formula(I) as described in the broadest generic aspect, and wherein
n is 2;
ring A and the phenyl ring to which it is fused form:

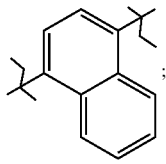

G is
phenyl, pyridinyl, pyridonyl, naphthyl, quinolinyl, isoquinolinyl, pyrazinyl, piperidinyl, tetrahydropyranyl, benzimidazolyl, benzoxazolyl, benzooxazolonyl, benzofuranyl, benzothiophenyl, benzopyrazolyl, dihydrobenzofuranyl, dihydrobenzothiophenyl, 3,4-dihydro-2H-benz[1,4]oxazinyl, indanyl, indenyl, indolyl, indolinyl, indolonyl, 2,3-dihydro-1H-indolyl or indolinonyl, wherein G is substituted by one $R_3$ and further substituted by one or more $R_1$ or $R_2$;
L is:
—O—, >C(O), —OCH$_2$—, —CH$_2$—, —CH(OH)—, —CH$_2$—CH(OH)—, —CH(OH)CH$_2$—, —OCH$_2$CH$_2$—, —OCH$_2$CH$_2$CH$_2$—, —OCH$_2$CH$_2$(CH$_3$)—, —OCH$_2$(CH$_3$)CH$_2$—, —CH$_2$CH$_2$—, —CH$_2$CH$_2$CH$_2$—, —OCH$_2$C(O)—, —CH=CHCH$_2$— or —CH=CHCH$_2$CH$_2$—, —NH—, —NHCH$_2$—, —NHCH$_2$CH$_2$—, —S(O)$_m$—, —S(O)$_m$CH$_2$—, —S(O)$_m$CH$_2$CH$_2$— and —S(O)$_m$CH$_2$CH$_2$CH$_2$—;
Q is:
phenyl, pyridinyl, pyrimidinyl, pyridazinyl, imidazolyl, thiazolyl, oxazolyl, pyrazinyl, pyrazolyl, morpholinyl, thiomorpholinyl, tetrahydropyranyl, 8-oxa-3-aza-bicyclo[3.2.1]octanyl, piperazinyl or piperidinyl each optionally substituted by one $C_{1-6}$ alkyl or phenyl;
$R_1$ is independently:
$C_{3-5}$ branched or unbranched alkyl optionally partially or fully halogenated, and optionally substituted with one to three $C_{3-6}$ cycloalkyl, hydroxy and phenyl; N-morpholinyl; cyclopropyl, cyclobutyl, cyclopentanyl, cyclohexanyl, bicyclopentanyl or bicyclohexanyl optionally partially or fully halogenated and optionally substituted with one to three $C_{1-3}$ alkyl groups optionally partially or fully halogenated, cyano, hydroxy$C_{1-3}$ alkyl or phenyl;
$R_2$ is independently:
a $C_{1-6}$ branched or unbranched alkyl optionally partially or fully halogenated or $C_{1-4}$ branched or unbranched alkoxy optionally partially or fully halogenated;

$R_3$ is
$(J)_{0-1}$—L'—S(O)$_m$—NH— or $(J)_{0-1}$—L'—O—C(O)—NH—,
wherein for $R_3$:
L' is
a bond, $C_{1-5}$ alkyl, hydroxy $C_{1-5}$ alkyl, $C_{2-4}$ alkenyl, amido$C_{1-5}$ alkyl;
J is:
cyclopropyl, cyclobutyl, cyclopentyl, cyclohexyl, cycloheptyl, bicyclopentanyl, bicyclohexanyl or bicycloheptanyl,
phenyl, naphthyl, morpholinyl, piperidinyl, piperazinyl, pyridinyl, pyrimidinyl, pyrazinyl, pyridazinyl, pyrrolyl, pyrrolidinyl, imidazolyl, pyrazolyl, thiazolyl, oxazolyl, thienyl, furyl, dioxolanyl, tetrahydrofuryl, isoxazolyl and isothiazolyl,
cyclobutenyl, cyclopentenyl, cyclohexenyl, cyclohexadienyl, cycloheptenyl, cycloheptadienyl, bicyclohexenyl or bicycloheptenyl;
each of the above J is optionally substituted by one to two $R_4$;
$R_4$ is oxo or mono- or di-$C_{1-3}$ alkylamino;
Y is
a bond, —O—, >C(O), —NH—, —C(O)—NH—, —S—, $C_{1-5}$ alkyl branched or unbranched, $C_{2-5}$ alkenyl, $C_{1-3}$ acyl, $C_{1-3}$ alkyl(OH), heterocycle selected from morpholinyl, piperazinyl, piperidinyl, pyrrolidinyl or tetrahydrofuryl, heteroaryl selected from pyridinyl, pyrimidinyl, pyrazinyl, pyridazinyl, pyrrolyl, imidazolyl, pyrazolyl, thienyl, furyl, isoxazolyl, thiazolyl, oxazolyl, indolyl or isothiazolyl or aryl each alkyl, alkenyl, acyl, heterocycle, heteroaryl and aryl are optionally substituted by one to three hydroxy, oxo, $C_{1-3}$ alkyl, $C_{1-3}$ alkoxy, $C_{1-5}$ alkoxycarbonyl, NR$_5$R$_6$ or NR$_5$R$_6$—C(O)—;
wherein each Y is optionally further covalently attached to phenylC$_{0-4}$ alkyl,
each $R_5$ and $R_6$ are independently hydrogen, phenylC$_{0-3}$alkyl optionally subtituted by halogen, $C_{1-3}$ alkyl or di$C_{1-5}$ alkyl amino, $C_{1-2}$ acyl, benzoyl or $C_{1-4}$ branched or unbranched alkyl optionally substituted by $C_{1-4}$ alkoxy, hydroxy or mono or di$C_{1-3}$ alkyl amino;
m is 2;
and
X is O.

In yet another embodiment of the invention there is provided compounds of the formula(I) as described immediately above, and wherein:
G is phenyl, pyridinyl, pyridonyl, naphthyl, quinolinyl, isoquinolinyl, pyrazinyl, benzothiophenyl, dihydrobenzofuranyl, dihydrobenzothiophenyl, indanyl, indolyl, indolinyl, indolonyl, indolinonyl, piperidinyl or tetrahydropyranyl, wherein G is substituted by one $R_3$ and further substituted by one to three $R_1$ or $R_2$;

L' is
a bond, $C_{1-5}$ alkyl, hydroxy $C_{1-5}$ alkyl, $C_{2-4}$ alkenyl or amido$C_{1-5}$ alkyl.

In yet still another embodiment of the invention there is provided compounds of the formula(I) as described immediately above, and wherein G is phenyl, pyridinyl, pyridonyl, naphthyl, quinolinyl, isoquinolinyl, dihydrobenzofuranyl, indanyl, indolinyl, indolonyl or indolinonyl, wherein G is substituted by one $R_3$ and further substituted by one to three $R_1$ or $R_2$;

L is:
—O—, >C(O), —OCH$_2$—, —CH$_2$—, —OCH$_2$CH$_2$—, —OCH$_2$CH$_2$CH$_2$—, —OCH$_2$CH$_2$(CH$_3$)—, —OCH$_2$(CH$_3$)CH$_2$—, —NH—, —NHCH$_2$—, —NHCH$_2$CH$_2$—, —S(O)$_m$—, —S(O)$_m$CH$_2$—, —S(O)$_m$CH$_2$CH$_2$—, —S(O)$_m$CH$_2$CH$_2$CH$_2$—, —CH$_2$CH$_2$—, —CH$_2$CH$_2$CH$_2$— or —OCH$_2$C(O)—;

each $R_1$ is independently:
$C_{3-5}$ branched or unbranched alkyl optionally partially or fully halogenated and optionally substituted with phenyl or $R_1$ is N-morpholinyl;
cyclopropyl, cyclopentanyl, cyclohexanyl or bicyclopentanyl optionally substituted with one to three methyl groups optionally be partially or fully halogenated, cyano, hydroxymethyl or phenyl;
substituted by methyl;
Q is
phenyl, pyridinyl, pyrimidinyl, imidazolyl, tetrahydropyranyl, 8-oxa-3-aza-bicyclo[3.2.1]octanyl or morpholinyl each optionally substituted by one $C_{1-3}$ alkyl or phenyl;
Y is
a bond, —O—, —S—, >C(O), —NH—, —C(O)—NH—, —CH($C_{1-2}$ alkyl)-;
or Y is $C_{1-2}$ alkyl, $C_{1-2}$ alkyl(OH), $C_{2-4}$ alkenyl, $C_{1-2}$ acyl, imidazolyl, pyrazolyl, thienyl, pyrrolidinyl, pyrrolyl, indolyl, isoxazolyl, thiazolyl, oxazolyl, isothiazolyl or phenyl each optionally substituted by one to two hydroxy, oxo, $C_{1-3}$ alkyl, $C_{1-3}$ alkoxy, $C_{1-5}$ alkoxycarbonyl, NR$_5$R$_6$ or NR$_5$R$_6$—C(O)—;
wherein each Y is optionally further covalently attached to phenyl$C_{0-4}$ alkyl;
each $R_5$ and $R_6$ are independently hydrogen, phenyl$C_{0-3}$ alkyl optionally subtituted by halogen or $C_{1-3}$ alkyl, acetyl, benzoyl or $C_{1-4}$ branched or unbranched alkyl optionally substituted by $C_{1-3}$ alkoxy, hydroxy, mono or di$C_{1-3}$ alkyl amino.

In another embodiment of the invention there is provided of the formula(I) as described immediately above, and wherein G is phenyl substituted by one $R_3$ and further independently substituted by one to two $R_1$ or $R_2$; and L is:
>C(O), —O—, —NH—, —CH$_2$— or —S(O)$_m$—;

Q is pyridinyl, morpholinyl, 8-oxa-3-aza-bicyclo[3.2.1]octanyl or phenyl each optionally substituted by methyl or phenyl;

$R_3$ is
L'—S(O)$_2$—NH or L'—O—C(O)—NH— wherein L' is $C_{1-5}$alkyl.

In yet another embodiment of the invention there is provided of the formula(I) as described in the fourth embodiment above, and wherein L is:
>C(O), —O— or —CH$_2$—;

$R_1$ is
tert-butyl optionally partially or fully halogenated;

$R_2$ is independently:

$C_{1-3}$ alkyl or $C_{1-3}$ alkoxy;

Q is N-morpholinyl optionally substituted at the 6-position by methyl or phenyl or Q is 8-oxa-3-aza-bicyclo[3.2.1]octanyl;

Y is

—O—, >C(O), —CH(CH$_3$)—, —CH(OH)—, —C(O)—NH—;

or Y is CH$_2$—, CH$_2$CH$_2$OH, pyrrolidinyl, pyrrolyl, indolyl or phenyl each optionally substituted by one hydroxy, oxo, $C_{1-3}$ alkyl, $C_{1-3}$ alkoxy, $C_{1-5}$ alkoxycarbonyl, NR$_5$R$_6$ or NR$_5$R$_6$—C(O)—;

wherein each Y is optionally further covalently attached to phenyl;

each $R_5$ and $R_6$ are independently hydrogen, phenyl$C_{0-3}$ alkyl optionally subtituted by halogen or $C_{1-3}$ alkyl, acetyl, benzoyl or $C_{1-4}$ branched or unbranched alkyl optionally substituted by $C_{1-2}$ alkoxy, hydroxy or mono or di$C_{1-3}$ alkyl amino.

In another embodiment of the invention there is provided of the formula(I) as described immediately above, and wherein L is >C(O);

Y is

—O—, —CH$_2$—, —CH$_2$CH$_2$OH;

or Y is pyrrolyl, indolyl or phenyl each optionally substituted by one $C_{1-5}$ alkoxycarbonyl; and $R_3$ is $C_{1-3}$ alkyl-S(O)$_2$—NH— or $C_{1-3}$ alkyl-O—C(O)—NH—.

In an ultimately preferred embodiment of the invention there is provided of the formula(I) as described immediately above, and wherein $R_3$ is CH$_3$—S(O)$_2$—NH— or CH$_3$—O—C(O)—NH—.

The following are representative compounds of the formula (I) where n is 2 which can be made by the methods disclosed herein:

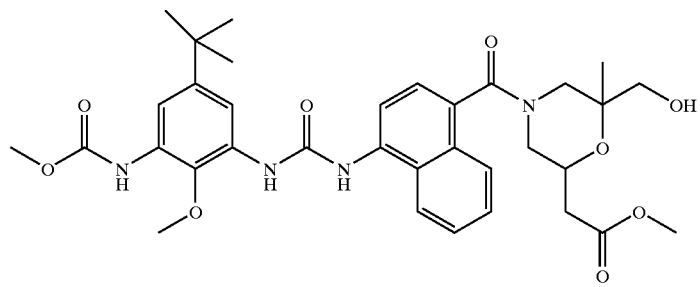

(4-{4-[3-(5-tert-Butyl-2-methoxy-3-methoxycarbonyl-amino-phenyl)-ureido]-naphthalene-1-carbonyl}-6-hydroxymethyl-6-methyl-morpholin-2-yl)-acetic acid methyl ester;

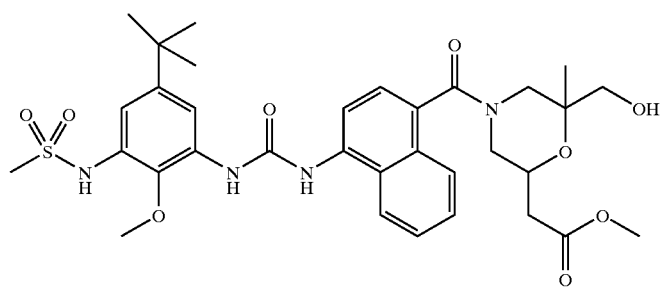

(4-{4-[3-(5-tert-Butyl-3-methanesulfonylamino-2-methoxy-phenyl)-ureido]-naphthalene-1-carbonyl}-6-hydroxymethyl-6-methyl-morpholin-2-yl)-acetic acid methyl ester;

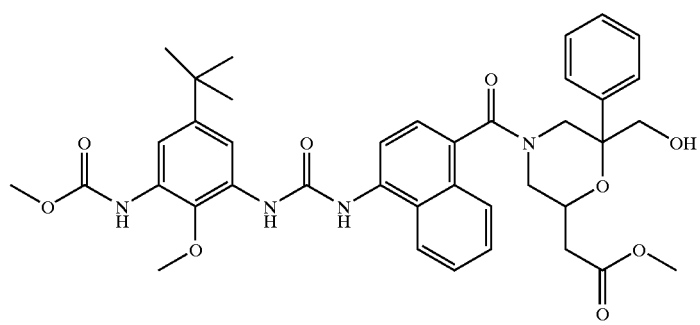

(4-{4-[3-(5-tert-Butyl-2-methoxy-3-methoxycarbonyl-amino-phenyl)-ureido]-naphthalene-1-carbonyl}-6-hydroxymethyl-6-phenyl-morpholin-2-yl)-acetic acid methyl ester;

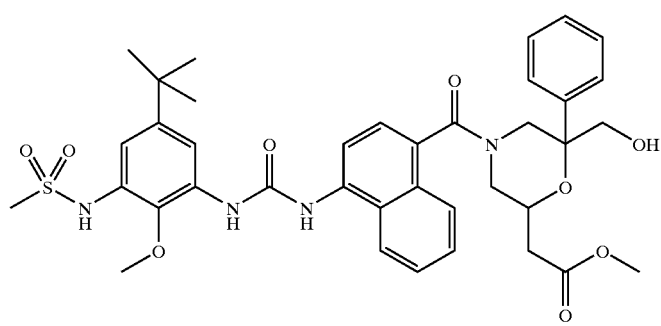

(4-{4-[3-(5-tert-Butyl-3-methanesulfonylamino-2-methoxy-phenyl)-ureido]-naphthalene-1-carbonyl}-6-hydroxymethyl-6-phenyl-morpholin-2-yl)-acetic acid methyl ester;

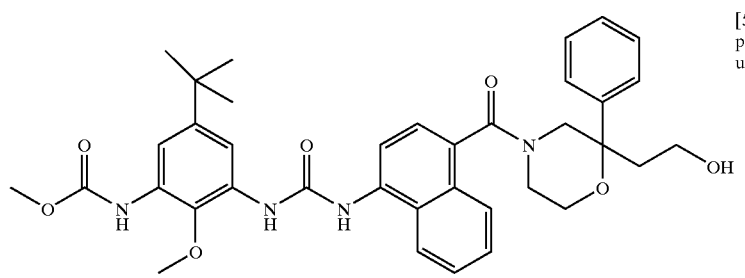

[5-tert-Butyl-3-(3-{4-[2-(2-hydroxy-ethyl)-2-phenyl-morpholine-4-carbonyl]-naphthalen-1-yl}-ureido)-2-methoxy-phenyl]-carbamic acid methyl ester -continued

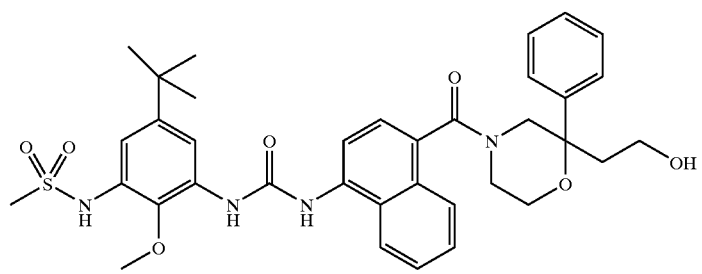

[5-tert-Butyl-3-(3-{4-[2-(2-hydroxy-ethyl)-2-phenyl-morpholine-4-carbonyl]-naphthalen-1-yl}-ureido)-2-methoxy-phenyl]-methanesulfonamide

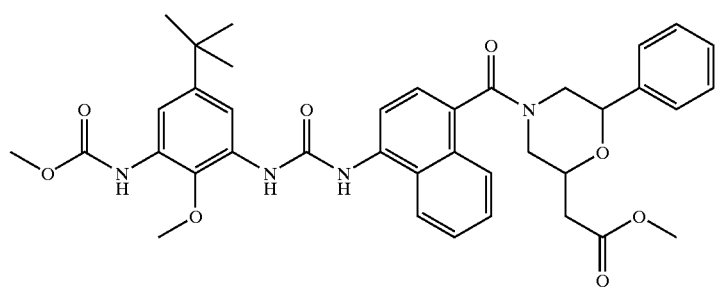

(4-{4-[3-(5-tert-Butyl-2-methoxy-3-methoxycarbonyl-amino-phenyl)-ureido]-naphthalene-1-carbonyl}-6-phenyl-morpholin-2-yl)-acetic acid methyl ester;

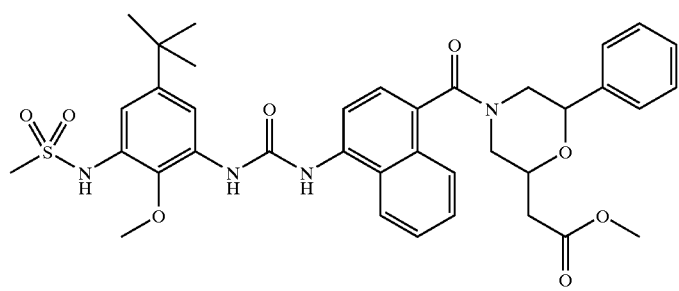

(4-{4-[3-(5-tert-Butyl-2-methoxy-3-methoxycarbonyl-amino-phenyl)-ureido]-naphthalene-1-carbonyl}-6-phenyl-morpholin-2-yl)-methanesulfonamide;

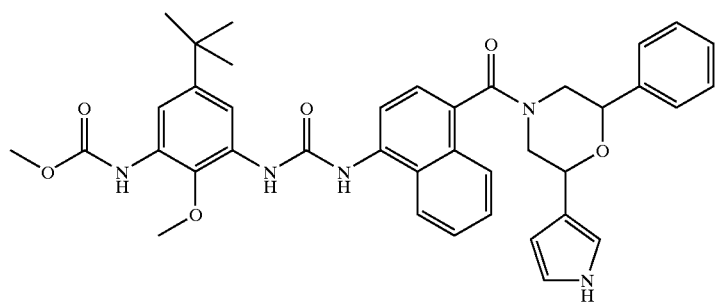

[5-tert-Butyl-2-methoxy-3-(3-{4-[2-phenyl-6-(1H-pyrrol-3-yl)-morpholine-4-carbonyl]-naphthalen-1-yl}-ureido)-phenyl]-carbamic acid methyl ester;

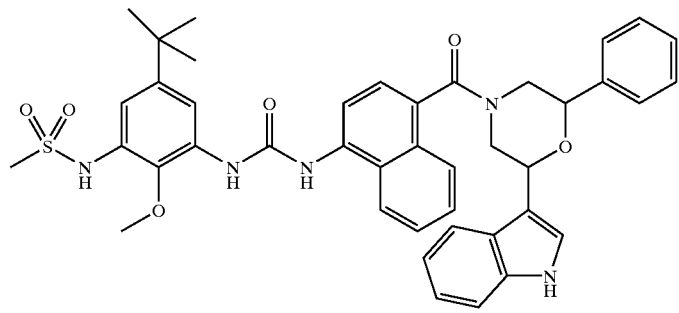

[5-tert-Butyl-2-methoxy-3-(3-{4-[2-phenyl-6-(1H-indol-3-yl)-morpholine-4-carbonyl]-naphthalen-1-yl}-ureido)-phenyl]-methanesulfonamide;

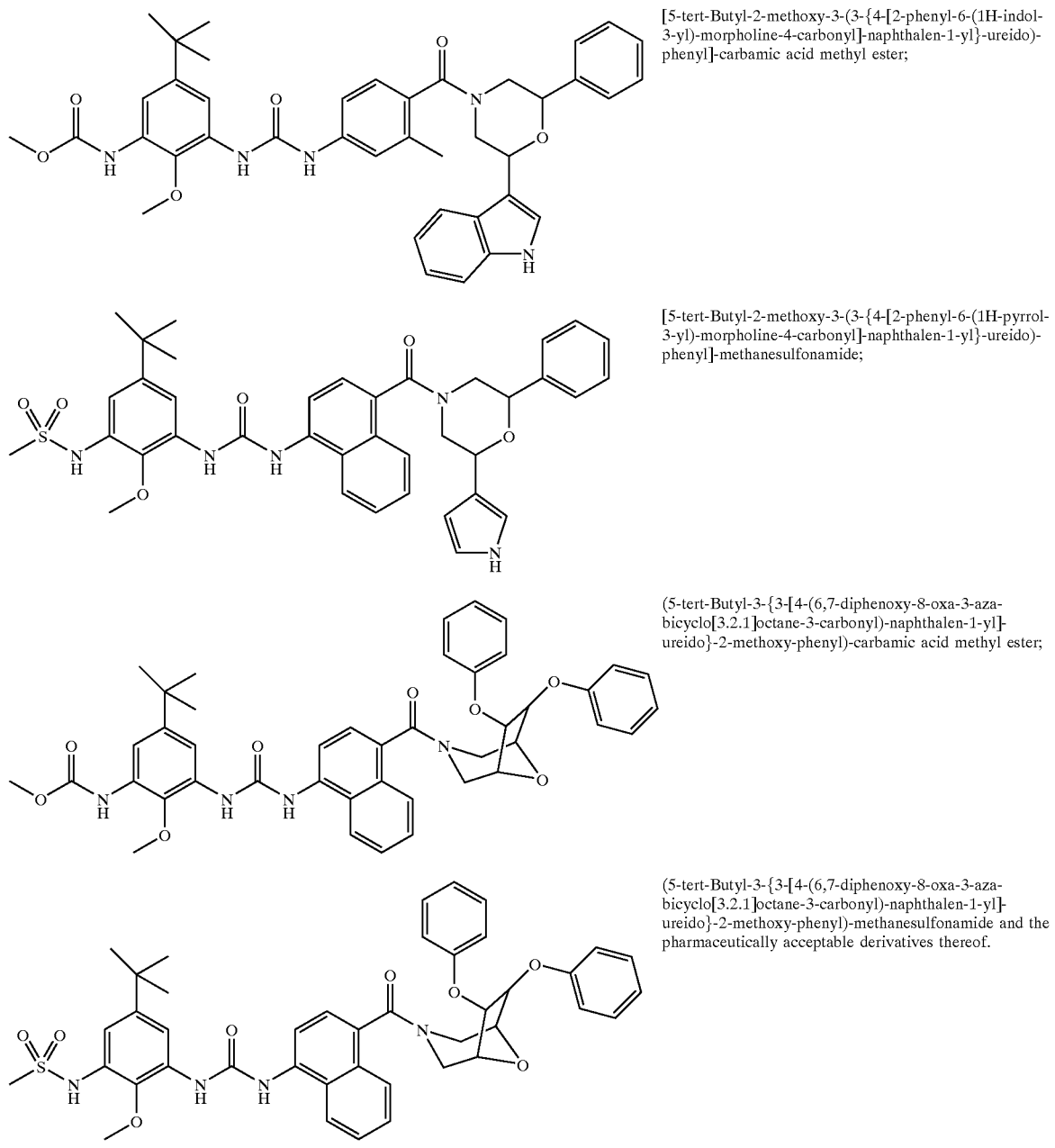

[5-tert-Butyl-2-methoxy-3-(3-{4-[2-phenyl-6-(1H-indol-3-yl)-morpholine-4-carbonyl]-naphthalen-1-yl}-ureido)-phenyl]-carbamic acid methyl ester;

[5-tert-Butyl-2-methoxy-3-(3-{4-[2-phenyl-6-(1H-pyrrol-3-yl)-morpholine-4-carbonyl]-naphthalen-1-yl}-ureido)-phenyl]-methanesulfonamide;

(5-tert-Butyl-3-{3-[4-(6,7-diphenoxy-8-oxa-3-aza-bicyclo[3.2.1]octane-3-carbonyl)-naphthalen-1-yl]-ureido}-2-methoxy-phenyl)-carbamic acid methyl ester;

(5-tert-Butyl-3-{3-[4-(6,7-diphenoxy-8-oxa-3-aza-bicyclo[3.2.1]octane-3-carbonyl)-naphthalen-1-yl]-ureido}-2-methoxy-phenyl)-methanesulfonamide and the pharmaceutically acceptable derivatives thereof.

In a fourth subgeneric aspect of the invention there is provided compounds of the formula(I) as described in the broadest generic aspect, and wherein
n is 0 or 1;
ring A and the phenyl ring to which it is fused form:

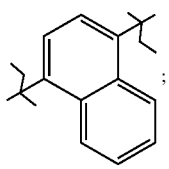

L is
>CR$_x$R$_y$ wherein

R$_x$ and R$_y$ are each independently hydrogen, heterocycleC$_{0-4}$ alkyl wherein the heterocyclic moiety is chosen from piperidinyl, morpholinyl and piperazinyl, imidazolylC$_{0-4}$ alkyl or phenylC$_{0-4}$ alkyl;

G is phenyl, pyridinyl, pyridonyl, naphthyl, quinolinyl, isoquinolinyl, pyrazinyl, piperidinyl, tetrahydropyranyl, benzimidazolyl, benzoxazolyl, benzooxazolonyl, benzofuranyl, benzothiophenyl, benzopyrazolyl, dihydrobenzofuranyl, dihydrobenzothiophenyl, 3,4-dihydro-2H-benz[1,4]oxazinyl, indanyl, indenyl, indolyl, indolinyl, indolonyl, 2,3-dihydro-1H-indolyl or indolinonyl, wherein G is substituted by one $R_3$ and further substituted by one or more $R_1$ or $R_2$;

Q is:

phenyl, pyrimidinyl, imidazolyl, pyridinyl, tetrahydropyranyl or morpholinyl;

$R_1$ is independently:

$C_{3-5}$ branched or unbranched alkyl optionally partially or fully halogenated, and optionally substituted with one to three $C_{3-6}$ cycloalkyl, hydroxy and phenyl;

N-morpholinyl;

cyclopropyl, cyclobutyl, cyclopentanyl, cyclohexanyl, bicyclopentanyl or bicyclohexanyl optionally partially or fully halogenated and optionally substituted with one to three $C_{1-3}$ alkyl groups optionally partially or fully halogenated, cyano, hydroxy$C_{1-3}$ alkyl or phenyl;

$R_2$ is independently:

a $C_{1-6}$ branched or unbranched alkyl optionally partially or fully halogenated or $C_{1-4}$ branched or unbranched alkoxy optionally partially or fully halogenated;

$R_3$ is $(J)_{0-1}$—L'—S(O)$_m$—NH— or $(J)_{0-1}$—L'—O—C(O)—NH—, wherein for $R_3$:

L' is a bond, $C_{1-5}$ alkyl, hydroxy $C_{1-5}$ alkyl, $C_{2-4}$ alkenyl, amido$C_{1-5}$ alkyl;

J is:

cyclopropyl, cyclobutyl, cyclopentyl, cyclohexyl, cycloheptyl, bicyclopentanyl, bicyclohexanyl or bicycloheptanyl, phenyl, naphthyl, morpholinyl, piperidinyl, piperazinyl, pyridinyl, pyrimidinyl, pyrazinyl, pyridazinyl, pyrrolyl, pyrrolidinyl, imidazolyl, pyrazolyl, thiazolyl, oxazolyl, thienyl, furyl, dioxolanyl, tetrahydrofuryl, isoxazolyl and isothiazolyl, cyclobutenyl, cyclopentenyl, cyclohexenyl, cyclohexadienyl, cycloheptenyl, cycloheptadienyl, bicyclohexenyl or bicycloheptenyl;

each of the above J is optionally substituted by one to two $R_4$;

$R_4$ is oxo or mono- or di-$C_{1-3}$ alkylamino;

Y is a bond or >C(O), further covalently attached to $NR_5R_6$, $C_{1-3}$ alkyl, $C_{3-6}$ cycloalkyl$C_{0-2}$alkyl, hydroxy, $C_{1-3}$ alkoxy, phenoxy, phenyl$C_{0-4}$alkyl, piperazinyl$C_{0-4}$ alkyl, piperidinyl $C_{04}$alkyl, pyrrolidinyl$C_{0-4}$ alkyl, morpholinyl$C_{0-4}$ alkyl, tetrahydrofuranyl$C_{0-4}$ alkyl or pyridinyl $C_{0-4}$alkyl, each abovelisted heterocycle, heteroaryl and phenyl are optionally substituted by one to three hydroxy, oxo, $C_{1-4}$ alkyl, $C_{1-3}$ alkoxy, $C_{1-5}$ alkoxycarbonyl, $NR_5R_6$—C(O)— or $C_{1-4}$ acyl, each $R_5$ and $R_6$ are independently hydrogen, phenyl$C_{0-3}$ alkyl optionally subtituted by halogen, $C_{1-3}$ alkyl or di$C_{1-5}$ alkyl amino, $C_{1-2}$ acyl, benzoyl or $C_{1-4}$ branched or unbranched alkyl optionally substituted by $C_{1-4}$ alkoxy, hydroxy or mono or di$C_{1-3}$ alkyl amino;

m is 2;

and

X is O.

In yet another embodiment of the invention there is provided compounds of the formula(I) as described immediately above, and wherein:

G is phenyl, pyridinyl, pyridonyl, naphthyl, quinolinyl, isoquinolinyl, pyrazinyl, benzothiophenyl, dihydrobenzofuranyl, dihydrobenzothiophenyl, indanyl, indolyl, indolinyl, indolonyl, indolinonyl, piperidinyl or tetrahydropyranyl, wherein G is substituted by one $R_3$ and further substituted by one to three $R_1$ or $R_2$;

L' is a bond, $C_{1-5}$ alkyl, hydroxy $C_{1-5}$ alkyl, $C_{2-4}$ alkenyl or amido$C_{1-5}$ alkyl.

In yet still another embodiment of the invention there is provided compounds of the formula(I) as described immediately above, and wherein G is phenyl, pyridinyl, pyridonyl, naphthyl, quinolinyl, isoquinolinyl, dihydrobenzofuranyl, indanyl, indolinyl, indolonyl or indolinonyl, wherein G is substituted by one $R_3$ and further substituted by one to three $R_1$ or $R_2$;

L is:

>$CR_xR_y$ wherein one of $R_x$ and $R_y$ is hydrogen and the other is heterocycle wherein the heterocyclic moiety is chosen from piperidinyl, morpholinyl and piperazinyl, imidazolyl or benzyl;

each $R_1$ is independently:

$C_{3-5}$ branched or unbranched alkyl optionally partially or fully halogenated and optionally substituted with phenyl or $R_1$ is N-morpholinyl;

cyclopropyl, cyclopentanyl, cyclohexanyl or bicyclopentanyl optionally substituted with one to three methyl groups optionally be partially or fully halogenated, cyano, hydroxymethyl or phenyl;

cyclopentyloxy or cyclohexyloxy which are optionally partially or fully halogenated; 2-tetrahydrofuranyl substituted by methyl;

Q is phenyl, pyridinyl, pyrimidinyl, imidazolyl, tetrahydropyranyl or morpholinyl;

Y is a bond or >C(O), further covently attached to $NR_5R_6$, piperazinyl$C_{1-2}$ alkyl, piperidinyl$C_{1-2}$ alkyl, pyrrolidinyl$C_{1-2}$ alkyl, morpholinyl$C_{1-2}$ alkyl, tetrahydrofuranyl$C_{1-2}$ alkyl or pyridinyl$C_{1-2}$ alkyl;

each $R_5$ and $R_6$ are independently hydrogen or $C_{1-4}$ branched or unbranched alkyl optionally substituted by $C_{1-3}$ alkoxy, hydroxy, mono or di$C_{1-3}$ alkyl amino.

In another embodiment of the invention there is provided of the formula(I) as described immediately above, and wherein G is phenyl substituted by one $R_3$ and further independently substituted by one to two $R_1$ or $R_2$;

and

L is:

>$CR_xR_y$ wherein one of $R_x$ and $R_y$ is hydrogen and the other is heterocycle wherein the heterocyclic moiety is chosen from piperidinyl, morpholinyl and piperazinyl, imidazolyl or benzyl;

Q is phenyl, pyridinyl, tetrahydropyranyl or morpholinyl;

$R_3$ is $(J)_{0-1}$—L'—S(O)$_2$—NH or $(J)_{0-1}$—L'—O—C(O)—NH wherein

L' is $C_{1-5}$alkyl;

J is cyclobutenyl, N-morpholinyl, N-piperidinyl, N-piperazinyl or N-pyrrolidinyl, each J is optionally substituted by one to two $R_4$.

In yet another embodiment of the invention there is provided of the formula(I) as described in the fourth embodiment above, and wherein $R_1$ is tert-butyl optionally partially or fully halogenated;

$R_2$ is independently:

$C_{1-3}$ alkyl or $C_{1-3}$ alkoxy;

Q is pyridin-4-yl, tetrahydropyran-4-yl or N-morpholinyl;

Y is a bond or >C(O), further covently attached to $NR_5R_6$ or pyrrolidinyl$C_{1-2}$ alkyl; each $R_5$ and $R_6$ are independently hydrogen or $C_{1-4}$ branched or unbranched alkyl.

In another embodiment of the invention there is provided of the formula(I) as described immediately above, and wherein $R_3$ is $C_{1-3}$ alkyl—$S(O)_2$—NH— or $C_{1-3}$ alkyl—O—C(O)—NH—.

In an ultimately preferred embodiment of the invention there is provided of the formula(I) as described immediately above, and wherein
$R_3$ is $CH_3$—$S(O)_2$—NH— or $CH_3$—O—C(O)—NH—.

The following are representative compounds of the fourth subgeneric aspect of the invention, which can be made by the methods disclosed herein:

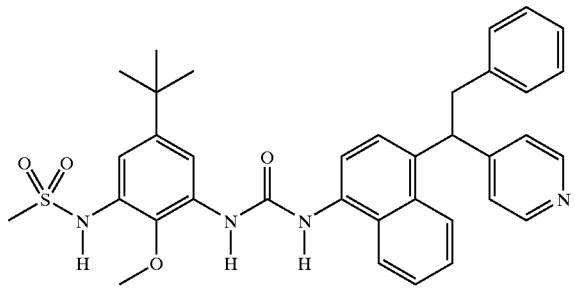

N-(5-tert-Butyl-2-methoxy-3-{3-[4-(2-phenyl-1-pyridin-4-yl-ethyl)naphthalen-1-yl]ureido}phenyl)methanesulfonamide;

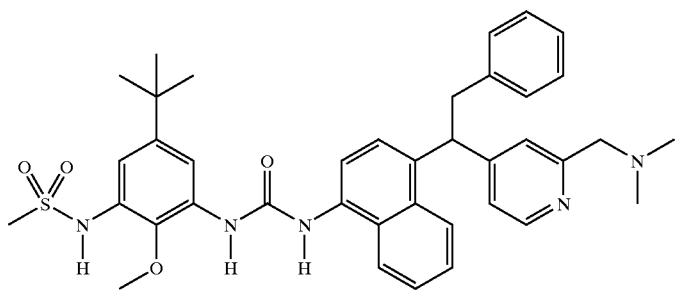

N-(5-tert-Butyl-2-methoxy-3-{3-[4-(2-phenyl-1-(2-dimethylaminomethyl)pyridin-4-yl-ethyl)naphthalen-1-yl]ureido}phenyl)methanesulfonamide;

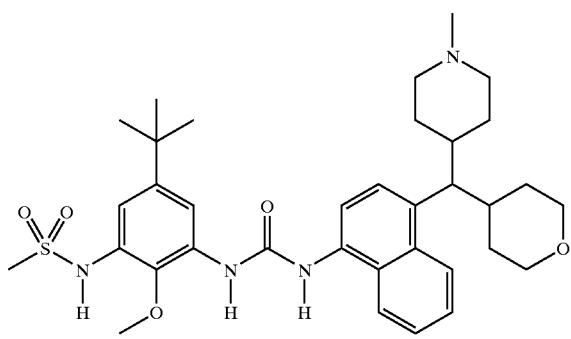

N-[5-tert-Butyl-2-methoxy-3-(3-{4-[(1-methylpiperdin-4-yl)-tetrahydropyran-4-yl)methyl]naphthalen-1-yl}ureido)phenyl]methanesulfonamide;

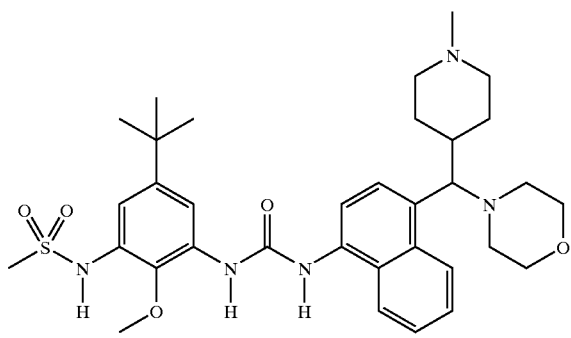

N-[5-tert-Butyl-2-methoxy-3-(3-{4-[(1-methylpiperdin-4-yl)-(morpholin-4-yl)methyl]naphthalen-1-yl}ureido)phenyl]methanesulfonamide;

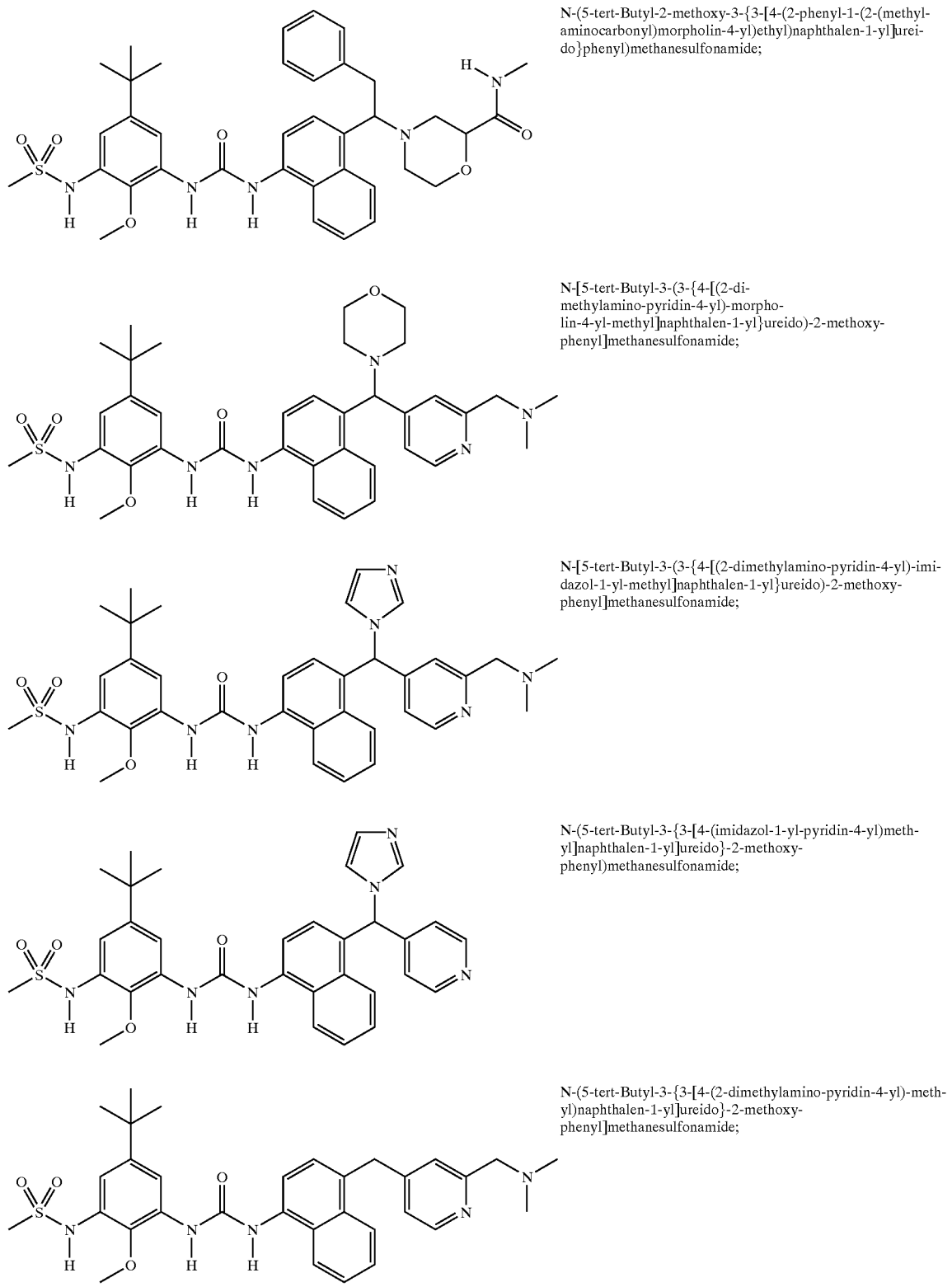

N-(5-tert-Butyl-2-methoxy-3-{3-[4-(2-phenyl-1-(2-(methyl-aminocarbonyl)morpholin-4-yl)ethyl)naphthalen-1-yl]ureido}phenyl)methanesulfonamide;

N-[5-tert-Butyl-3-(3-{4-[(2-dimethylamino-pyridin-4-yl)-morpholin-4-yl-methyl]naphthalen-1-yl}ureido)-2-methoxyphenyl]methanesulfonamide;

N-[5-tert-Butyl-3-(3-{4-[(2-dimethylamino-pyridin-4-yl)-imidazol-1-yl-methyl]naphthalen-1-yl}ureido)-2-methoxyphenyl]methanesulfonamide;

N-(5-tert-Butyl-3-{3-[4-(imidazol-1-yl-pyridin-4-yl)methyl]naphthalen-1-yl]ureido}-2-methoxyphenyl)methanesulfonamide;

N-(5-tert-Butyl-3-{3-[4-(2-dimethylamino-pyridin-4-yl)-methyl]naphthalen-1-yl]ureido}-2-methoxyphenyl]methanesulfonamide;

-continued

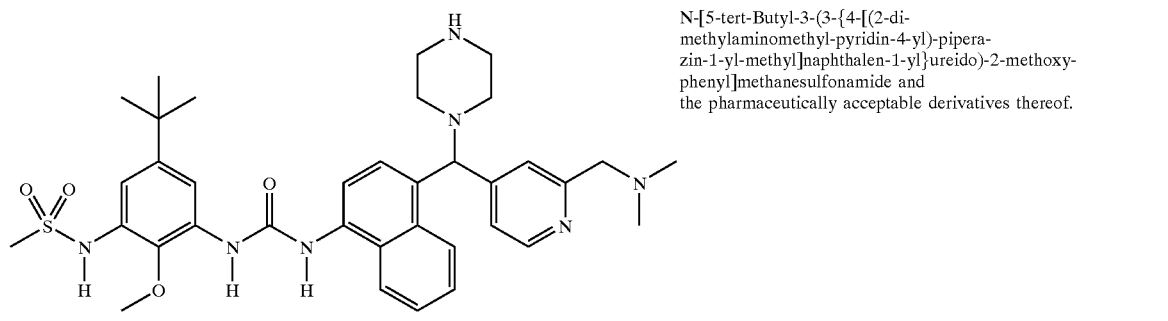

N-[5-tert-Butyl-3-(3-{4-[(2-di-methylaminomethyl-pyridin-4-yl)-piperazin-1-yl-methyl]naphthalen-1-yl}ureido)-2-methoxyphenyl]methanesulfonamide and the pharmaceutically acceptable derivatives thereof.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, and butoxy. All alkyl, alkenyl and alkynyl groups shall be understood as being branched or unbranched where structurally possible and unless otherwise specified. Other more specific definitions are as follows:

The term "aroyl" as used in the present specification shall be understood to mean "benzoyl" or "naphthoyl".

The term "carbocycle" shall be understood to mean an aliphatic hydrocarbon radical containing from three to twelve carbon atoms. Carbocycles include hydrocarbon rings containing from three to ten carbon atoms. These carbocycles may be either aromatic or non-aromatic ring systems. The non-aromatic ring systems may be mono- or polyunsaturated. Preferred carbocycles unless otherwise specified include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl.

The term "heterocycle" refers to a stable nonaromatic 4–8 membered (but preferably, 5 or 6 membered) monocyclic or nonaromatic 8–11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Preferred heterocycles include but are not limited to, for example oxetanyl, pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl, dithianyl.

The term "heteroaryl" shall be understood to mean an aromatic 5–8 membered monocyclic or 8–11 membered bicyclic ring containing 1–4 heteroatoms chosen from N, O and S. Included are the partially or fully saturated derivates thereof. Such heteroaryls unless otherwise specified include: pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzothiazolyl, benzoxazolyl, benzofuranyl, benzothiophenyl, benzopyrazolyl, dihydrobenzofuranyl, dihydrobenzothiophenyl, benzooxazolonyl, benz[1,4]oxazin-3-onyl, benzodioxolyl, benz[1,3]dioxol-2-onyl, tetrahydrobenzopyranyl, indolyl, indolinyl, indolonyl, indolinonyl, phthalimidyl.

The term "heteroatom" as used herein shall be understood to mean atoms other than carbon such as O, N, S and P.

The term "aryl" as used herein unless otherwise specified shall be understood to mean aromatic carbocycle or heteroaryl as defined herein.

Terms which are analogs of the above cyclic moieties such as aryloxy, heterocyclyloxy or heteroaryl amine shall be understood to mean an aryl, heteroaryl, heterocycle as defined above attached to it's respective group.

As used herein, "nitrogen" and "sulfur" include any oxidized form of nitrogen and sulfur and the quaternized form of any basic nitrogen. For example, if Y is —S—$C_{1-6}$ alkyl, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine.

The compounds of the invention are only those which are contemplated to be 'chemically stable' as will be appreciated by those skilled in the art. For example, a compound which would have a 'dangling valency', or a 'carbanion' are not compounds contemplated by the invention.

The invention includes pharmaceutically acceptable derivatives of compounds of formula (I). A "pharmaceutically acceptable derivative" refers to any pharmaceutically acceptable salt or ester of a compound of this invention, or any other compound which, upon administration to a patient, is capable of providing (directly or indirectly) a compound of this invention, a pharmacologically active metabolite or pharmacologically active residue thereof. A pharmacologically active metabolite shall be understood to mean any compound of the formula(I) capable of being metabolized enzymatically or chemically. This includes, for example, hydroxylated or oxidized derivative compounds of the formula(I).

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—$(C_1-C_4$ alkyl$)_4^+$ salts.

In addition, the compounds of this invention include prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug of this invention is administered to a patient, the prodrug may be transformed into a compound of formula (I), thereby imparting the desired pharmacological effect.

Methods of Use

In accordance with the invention, there are provided methods of using the compounds of the formula (I). The compounds of the invention effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds of the invention are useful for the treatment of such conditions. These encompass diseases including, but not limited to, rheumatoid arthritis, osteoarthritis, traumatic arthritis, multiple sclerosis, Guillain-Barre syndrome, Crohn's disease, ulcerative colitis, psoriasis, graft versus host disease, systemic lupus erythematosus, glomerulonephritis, reperfusion injury, sepsis, bone resorption diseases including osteoporosis, chronic obstructive pulmonary disease, congestive heart failure, Alzheimer's disease, atherosclerosis, toxic shock syndrome, asthma, contact dermatitis and insulin-dependent diabetes mellitus.

In addition, the compounds of the invention being inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A*, 1992, 89, 4888.) Accordingly, the present novel compounds would be expected to exhibit efficacy against those disorders currently treated with COX inhibitors such as the familiar NSAIDs. These disorders include acute and chronic pain as well as symptoms of inflammation and cardiovascular disease.

As discussed in the Background of the Invention, IL-8 plays a role in the influx of neutrophils into sites of inflammation or injury. Therefore, in a yet further aspect of the invention, the compounds of the invention may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing entrerocolitis.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the scheme below are either commercially available or easily prepared from commercially available materials by those skilled in the art.

General Synthetic Methods

The invention additionally provides for methods of making the compounds of the formula (I). The compounds of the invention and intermediates used in their preparation may be prepared by the general methods and examples presented below, and methods known to those of ordinary skill in the art. Further reference in this regard may be made to U.S. application Ser. Nos. 09/505,582, 09/484,638, 09/714,539, 09/611,109, 09/698,442 and U.S. provisional application No. 60/216,283. Each of the aforementioned are incorporated herein by reference in their entirety. In all schemes "G" in the formulas shown below shall have the meaning of "G" in the formula (I) of the invention described hereinabove. In all schemes "Ar" in the formulas shown below shall have the meaning of:

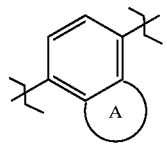

in the formula (I) of the invention described hereinabove.

The compounds of the invention may be prepared by Method A, B, C or D as illustrated in Scheme I, preferably Method C.

Scheme I

Method A

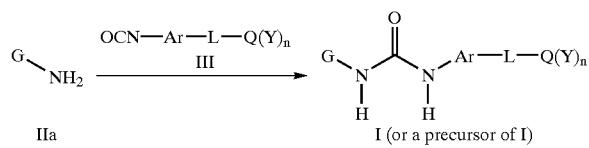

Method B

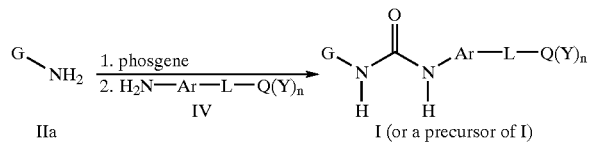

Method C

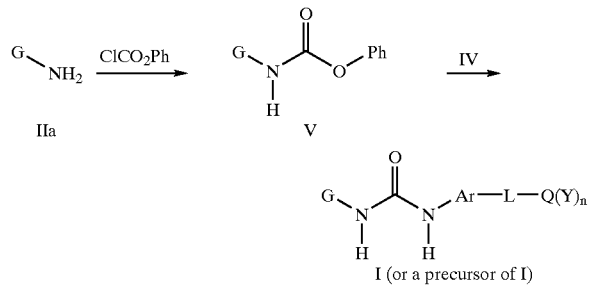

Method D

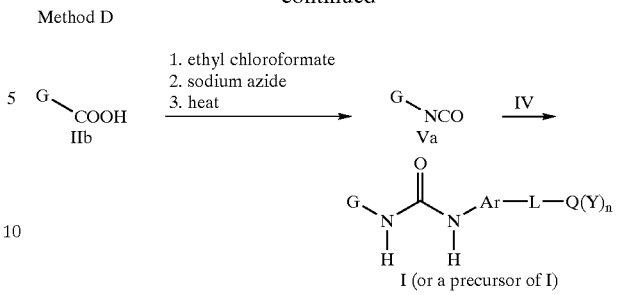

In Method A, a mixture of an arylamine of formula IIa and an arylisocyanate of formula III is dissolved in a non-protic, anhydrous solvent such as THF, ether, toluene, dioxane or ethyl acetate. The preferred solvent is THF. The mixture is stirred at between 0–45° C., preferably at 25° C., for 2–24 h, and the volatiles are removed. Purification of the residue can be accomplished by recrystallization from an appropriate solvent such as ethyl acetate/hexanes, ethyl acetate/methanol, THF/petroleum ether or ethanol/water or by silica gel chromatography, using for example, hexanes and ethyl acetate as eluents, providing the product of formula I or precursors thereof.

In Method B, an arylamine of formula IIa is dissolved in a halogenated solvent, such as methylene chloride, chloroform or dichloroethane. The preferred solvent is methylene chloride. The mixture is diluted with aqueous alkali, such as sodium bicarbonate or potassium carbonate, cooled in an ice bath and phosgene is added. The mixture is vigorously stirred for 5–30 min, with 10 min being preferable. The organic layer is dried, with agents such as $MgSO_4$ or $Na_2SO_4$, and the volatiles removed to provide the corresponding isocyanate. The isocyanate and arylamine IV are mixed in a non-protic, anhydrous solvent such as THF, ether, toluene, dioxane, methylene chloride or ethyl acetate. The preferred solvent is THF. The mixture is stirred at between 0–45° C., preferably at 25° C., for 2–24 h, and the volatiles are removed. Purification of the residue by recrystallization or by silica gel chromatography, as above, provides the product of formula I or precursors thereof.

In Method C, an arylamine of formula IIa is dissolved in a suitable halogenated solvent such as methylene chloride, chloroform or dichloroethane. The preferred solvent is methylene chloride. A suitable base such as triethylamine may be added, followed by an alkyl or aryl chloroformate, such as t-butyl chloroformate or phenyl chloroformate (shown). The mixture is stirred at between 0–85° C., preferably at reflux temperature, for 2–24 h, and the volatiles are removed providing carbamate V. The carbamate and arylamine IV are mixed in a non-protic, anhydrous solvent such as THF, ether, toluene, dioxane, methylene chloride or ethyl acetate. The preferred solvent is THF. The mixture is stirred at between 0–110° C., preferably at reflux temperature, for 2–24 h, and the volatiles are removed. Purification of the residue as above provides the product of formula I or precursors thereof.

In Method D, an aromatic carboxylic acid (IIb) is dissolved in a non-protic solvent, such as THF or diethyl ether, and an inorganic base, such as triethyl amine is added and the mixture is cooled to −30–0° C., with the preferred temperature being −10° C. An alkyl chloroformate, such as ethyl chloroformate, is added dropwise and the resulting mixture stirred at below room temperature, such as 0° C. for 1–3 hours. A solution of sodium azide in water is added and the mixture stirred between 1–3 hours, diluted with toluene and the organic layer dried and reduced in volume. This mixture is heated at reflux for 1–4 hours, cooled to room temperature to give isocyanate (Va) which can be reacted with amine (IV) to give product of formula I or precursors thereof.

EXPERIMENTAL SECTION

Amine intermediates of formula IIa are either commercially available or may be prepared by methods known to those skilled in the art. Examples 1–4 are representative of procedures for preparing aryl amine or aryl isocyanate derivatives that may be used in Methods A-D. It will be obvious to those skilled in the art that other desired intermediates could be made by these methods by using appropriately substituted starting materials and intermediates.

EXAMPLE 1

Synthesis of 5-tert-butyl-2-methoxy-3-nitroaniline

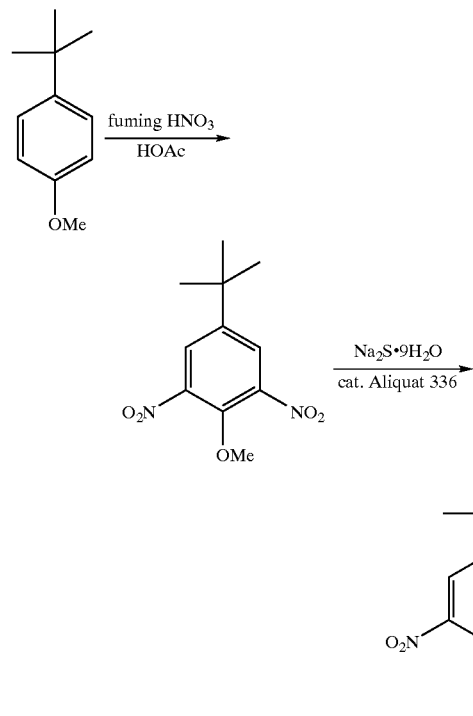

Fuming nitric acid (150 mL) was placed in a round bottom flask. A solution of 4-tert-butylanisole (16.4 g, 0.1 mol) in acetic acid (15 mL) was placed in an addition funnel and added dropwise to the flask. The flask was intermittently immersed in a water bath to maintain the temperature below 40° C. throughout the addition. Once the addition was complete, the reaction mixture was heated to 80° C., and maintained at that temperature for 2 h. The reaction mixture was cooled to ambient temperature, and then poured onto an ice/water mixture. A white solid soon formed, and the mixture was stirred for 30 min. The solid was isolated by vacuum filtration, and the filter cake was washed with water. The solid was dried on the filter. Recrystallization from hot 2-propanol provided 5-tert-butyl-2-methoxy-1,3-dinitrobenzene as white crystals (18.9 g, 75%).

To a suspension of 5-tert-butyl-2-methoxy-1,3-dinitrobenzene (10.2 g, 0.04 mol) in EtOAc (150 mL) was added in a single portion a solution of sodium sulfide nonahydrate (19.2 g, 0.08 mol) in water (200 mL). Aliquat® 336 (0.8 g, 5 mole %) was added in a single portion, and the two-phase mixture was brought to a reflux. All solids dissolved, and the mixture became red/brown. After about 3 h, TLC (3:1 hexanes:EtOAc) revealed almost complete loss of starting material. The mixture was filtered warm through a pad of diatomaceous earth to remove insolubles, and the filter cake was washed with fresh EtOAc. The clarified two-phase mixture was separated, and the organic layer was washed with sodium carbonate solution, followed by water and then saturated sodium chloride solution. After drying over magnesium sulfate, the solution was concentrated under reduced pressure to a thick, dark oil. This oil was extracted three times with refluxing hexanes, leaving behind a dark residue. The orange extract deposited some more dark oil, from which the warm supernatant was decanted. The resulting orange solution was heated back to reflux, and treated with both activated charcoal and diatomaceous earth. The solution was filtered hot, and the filter cake washed with hot hexanes. Re-heating the orange filtrate resulted in a clear solution. Quickly cooling the solution in an ice/acetone bath and scratching the flask with a glass rod resulted in the deposition of an orange/yellow precipitate. The suspension was allowed to cool for 1 h, and then filtered. The filter cake was washed with a small portion of cold hexanes, and then dried on the filter, providing the title compound as a yellow/orange powder (2.6 g, 30%).

EXAMPLE 2

Synthesis of 5-tert-butyl-2-methoxybenzene-1,3-diamine

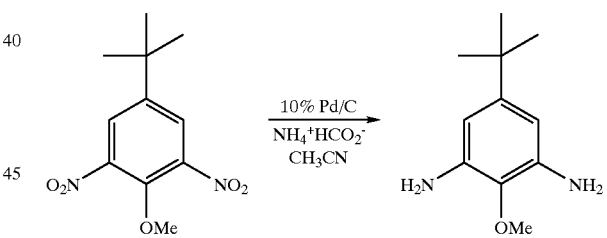

5-tert-Butyl-2-methoxy-1,3-dinitrobenzene (see Example 1, 1.9 g, 0.0075 mol) was added to EtOH (40 mL) under nitrogen purge. To this mixture, ammonium formate (4.9 g, 0.075 mol) was added in a single portion, followed by 10% palladium on carbon (0.75 g, 10 mole %), also in a single portion. This resulted in an immediate exotherm (temperature climbs to 30° C.), along with outgassing. Once the bubbling subsided, the mixture was slowly brought to reflux and maintained at this temperature for 3 h. An aliquot taken at this point showed over 93% conversion to a new, polar material. The mixture was filtered hot through a pad of diatomaceous earth, which was then washed twice with hot EtOH. The filtrate was concentrated under reduce pressure to obtain the title compound as a light grey solid (1.3 g, 90%).

EXAMPLE 3

Synthesis of 5-tert-butyl-2-methoxy-3-methylcarbamoylaniline

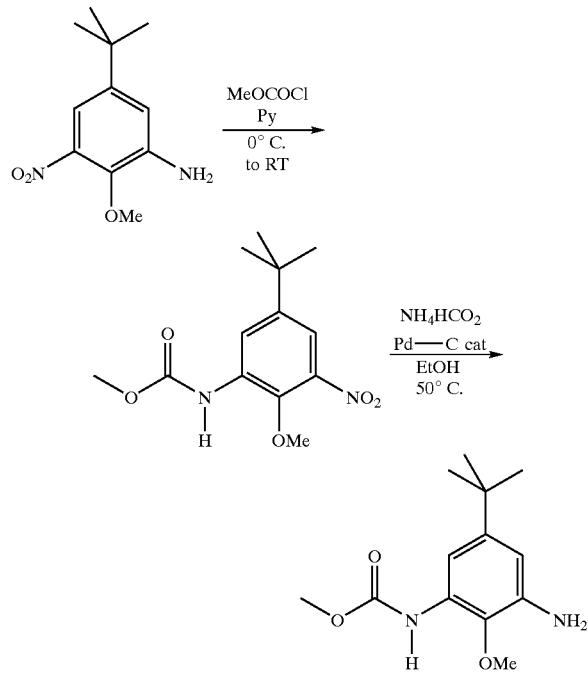

EXAMPLE 4

Synthesis of 5-tert-butyl-3-methanesulfonamido-2-methoxyaniline

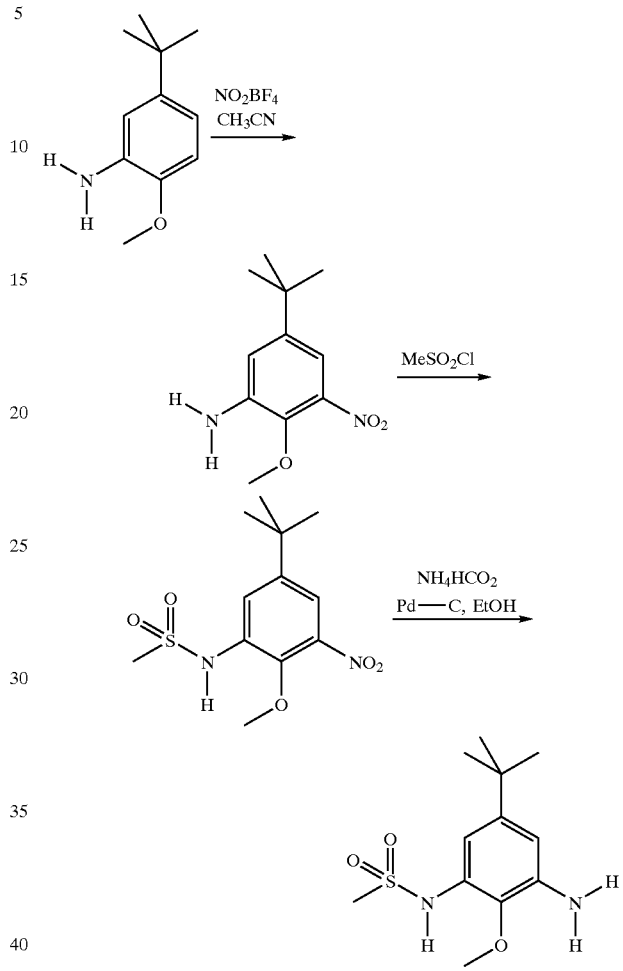

5-tert-Butyl-2-methoxy-3-nitroaniline (Example 1) (300 mg, 1.32 mmol) was dissolved in 1.0 mL anhydrous pyridine and cooled to 0° C. under inert atmosphere. Methyl chloroformate (97 microL, 1.26 mmol) was then added in one portion via syringe. The mixture was left to stir and slowly warm to room temperature overnight, then quenched with water (5 mL). The product was extracted with ether (3×5 mL) and dried over $Na_2SO_4$. The crude solution was filtered and the volatiles removed in vacuo. Purification by column chromatography on $SiO_2$ using 10–30% EtOAc in hexanes as eluent afforded 225 mg of the desired nitro-carbamate (0.80 mmol, 63% yield).

The above nitro-carbamate (225 mg, 0.80 mmol) dissolved in 5 mL EtOH was added to a solution of 10% palladium on carbon (225 mg) in 2 mL EtOH. Ammonium formate (301 mg, 4.8 mmol) was added and the mixture was heated to 50° C. for 1 h. The mixture was then cooled, filtered through a pad of diatomaceous earth, and the solvent removed in vacuo providing 200 mg (0.79 mmol, 99% yield) of the title compound.

The same general procedure outlined above may be used to prepare other desired alkyl or aryl carbamoyl anilines by substituting the appropriate alkyl or aryl chloroformate for methyl chloroformate.

5-tert-Butylanisole (5.38 g, 30.0 mmol, 1 equiv.) was dissolved in 80 mL anhydrous $CH_3CN$ and cooled to −35° C. under inert atmosphere. Nitronium tetrafluoroborate (4.78 g, 36.0 mmol, 1.2 equiv.) was then added in one portion. The reaction was stirred for 25 min, then quenched with a saturated aqueous solution of $NaHCO_3$ and extracted with dichloromethane (3×75 mL). The combined organic extracts were dried over $MgSO_4$, filtered, and the solvents were removed in vacuo. The crude oil was purified by column chromatography on $SiO_2$, using 0–30% EtOAc in hexanes to afford 5.70 g of 5-tert-butyl-2-methoxy-3-nitro aniline (25.2 mmol, 84% yield). (Example 1 describes an alternate synthesis of this intermediate.)

The nitro aniline (214 mg, 0.95 mmol, 1 equiv.) was dissolved in 1.0 mL anhydrous pyridine and cooled to 0° C. under inert atmosphere. Methane sulfonyl chloride (146 uL, 1.90 mmol, 2 equiv.) was then added dropwise via syringe. The mixture was left to stir for 6 h at 0° C., then poured over a mixture of 1 mL concentrated HCl and ice. The product was extracted with dichloromethane (3×20 mL) and dried over $MgSO_4$. The crude solution was filtered and the volatiles removed in vacuo. Purification by column chromatography on $SiO_2$ using 25–35% EtOAc in hexanes as eluent afforded 270 mg of nitro sulfonamide intermediate (0.89 mmol, 94% yield).

The nitro sulfonamide (270 mg, 0.89 mmol, 1 equiv.) was dissolved in 10 mL EtOH. Ammonium formate (288 mg, 4.56 mmol, 5.1 equiv.) and palladium-on-charcoal (10% Pd—C, ~150 mg) were added and the mixture was heated to 60° C. for 1 h. The mixture was then cooled, filtered through a pad of diatomaceous earth, and the solvent removed in vacuo. The aniline intermediate (220 mg, 88% yield) obtained was used in the subsequent coupling without purification.

The same general procedure outlined above may be used to prepare other desired alkyl or aryl sulfonamido anilines by substituting the appropriate alkyl or aryl sulfonyl chloride for methane sulfonyl chloride.

Examples 5–7 are representative procedures for the preparation of intermediates of formula IV that may be used in Methods B-D (Scheme I).

EXAMPLE 5

Synthesis of 4-[2-(morpholin-4-yl)ethoxy]napth-1-yl-amine

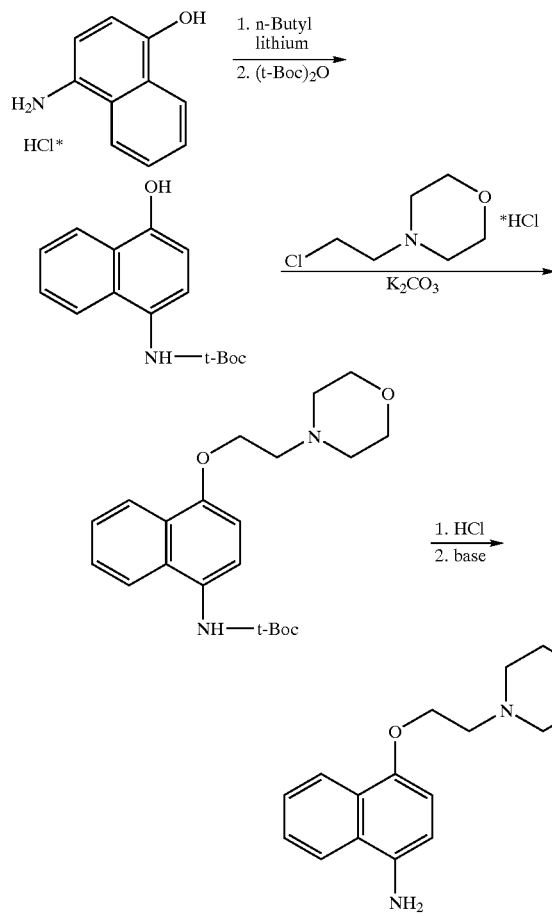

To a mixture of 4-amino-1-naphthol hydrochloride (172.1 g) in 750 mL anhydrous THF at −78° C., n-butyl lithium (490 mL of a 1.60 M solution in hexanes) was added dropwise over 60 min. After the addition was complete the mixture was allowed to warm to room temperature and then cooled to −78° C. and di-tert-butyl dicarbonate [(t-Boc)$_2$O, 192 g] in 200 mL THF was added over 20 min. The mixture was slowly warmed to room temperature and stirred for 3 h and most of the volatiles removed in vacuo. The residue was diluted with EtOAc (1 L) and washed with water (2×200 mL) and brine (200 mL) and filtered through diatomaceous earth and dried (MgSO$_4$). Removal of the volatiles in vacuo provided the N-t-Boc protected derivative (226.1 g).

A mixture of the above N-t-Boc derivative (0.464 g), 4-(2-chloroethyl)morpholine hydrochloride (0.3435 g) and powdered potassium carbonate (0.93 g) was heated in acetonitrile (15 mL) at 80° C. for 3 h, cooled to room temperature and diluted with EtOAc and water. The organic layer was washed with water, brine, dried (MgSO$_4$) and the volatiles removed in vacuo. Purification of the residue by flash chromatography using 12% hexanes in EtOAc as the eluent and concentration in vacuo of the product-rich fractions afforded N-t-Boc-4-[2-(morpholin-4-yl)ethoxy]napth-1-yl-amine. A solution of this intermediate (0.511 g) and HCl (1 mL of 4M HCl in dioxane solution) in 5 mL dioxane was stirred at room temperature for 20 h. The reaction was concentrated by rotary evaporation, and the residue dissolved in methylene chloride and washed with aqueous sodium carbonate. The organic layer was dried (Na$_2$SO$_4$), filtered and concentrated in vacuo providing 4-[2-(morpholin-4-yl)ethoxy]napth-1-yl-amine.

EXAMPLE 6

Synthesis of 1-amino-4-(4-pyridinyloxy)naphthalene

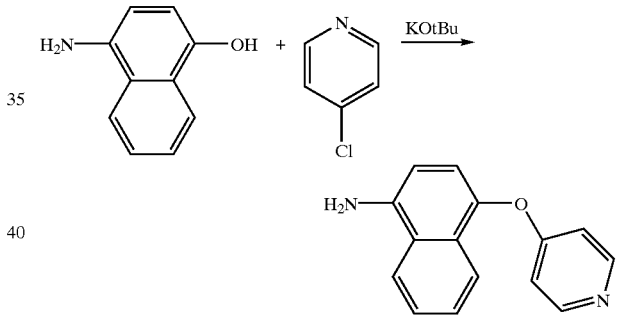

To a stirred mixture of 4-amino-1-naphthol hydrochloride (2.5 g, 12.8 mmol) and 4-chloropyridine hydrochloride (3.84 g, 29.2 mmol) in NMP (20 mL) was added potassium tert-butoxide (6.0 g, 53.47 mmol) slowly. The mixture was heated at 120° C. for 6 h, cooled to room temperature and diluted with water and dichloromethane. The combined organic extracts were washed with HCl (2N), saturated aqueous NaHCO$_3$ and brine and dried (Na$_2$SO$_4$). Removal of the volatiles in vacuo afforded the product (0.5 g, 16%).

EXAMPLE 7

Synthesis of 1-amino-4-(3-(tetrahydropyran-2-yl-oxy)propyn-1-yl)naphthalene

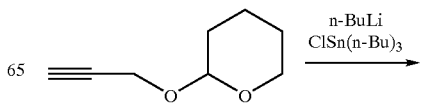

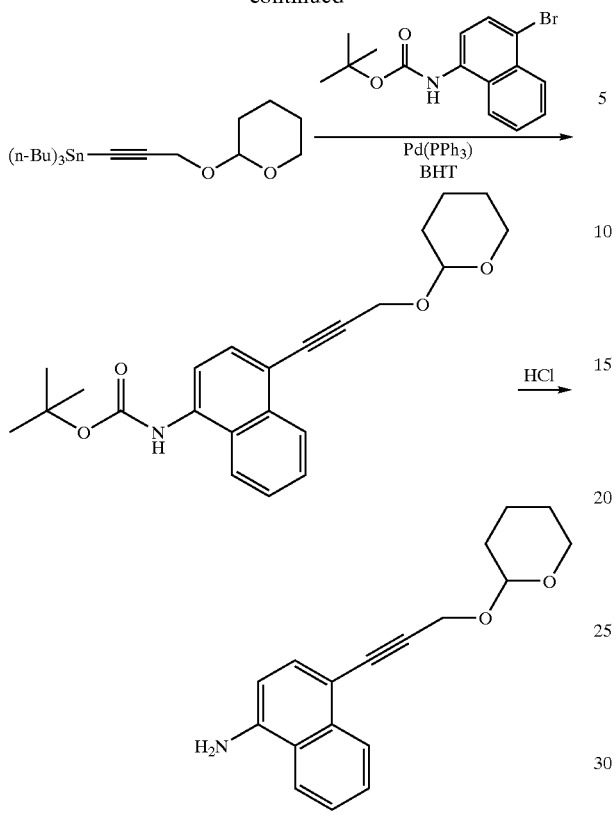

To a solution of tetrahydro-2-(2-propynyloxy)-2H-pyran in anhydrous THF at −78° C. under inert atmosphere n-butyllithium (1.1 molar equivalents) was added via syringe. After 1 h stirring at −78° C., tributyltin chloride (1 molar equivalent) was added and the cooling bath was removed. After stirring at ambient temperature for 1 h the reaction mixture was quenched with saturated NH$_4$Cl solution and extracted with ethyl ether. The combined ethereal extracts were washed with brine and dried (MgSO$_4$). After filtration all volatiles were removed in vacuo to produce the alkynyl tri-n-butylstannane as a yellow oil which was used without further purification.

A mixture of N-t-Boc-4-bromonaphthylamine and the above alkynyl stannane (1.5 molar equivalents) and BHT (20% weight equivalent) in toluene were heated at reflux under inert atmosphere and treated with palladium (0) tetrakis-(triphenylphosphine) (0.1 molar equivalent) When the reaction was complete, as judged by the color change to black, it was cooled to room temperature. An aqueous solution of KF (5M) was added and the mixture was stirred vigorously for 6 h and extracted with EtOAc. The combined organic extracts were washed with brine and dried (MgSO$_4$), filtered and all volatiles were removed in vacuo. Purification of the residue by column chromatography afforded the N-t-Boc intermediate. Removal of the N-t-Boc protecting group with HCl in dioxane provided the amino intermediate.

Examples 8–21 provide representative procedures by which compounds of formula (I) may be prepared.

EXAMPLE 8

1-[5-tert-butyl-3-methanesulfonamido-2-methoxyphenyl]-3-[4-(2-morpholin-4-yl-ethoxy)-naphthalen-1-yl]-urea

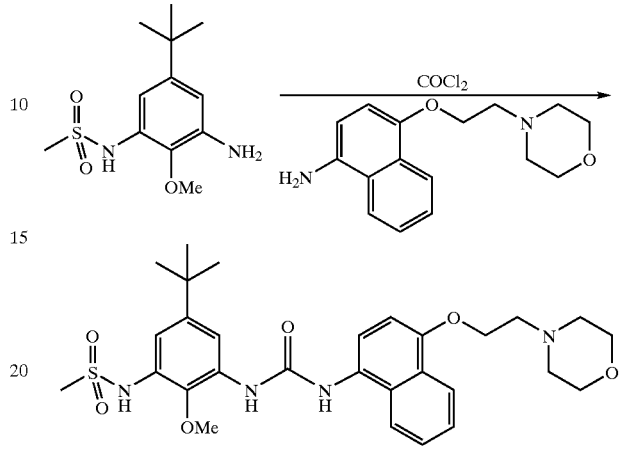

4-[2-(Morpholin-4-yl)ethoxy]napth-1-yl-amine (Example 5) (1.0 mmol) is dissolved in dichloromethane (15 mL). An equal volume of sat. aqueous sodium bicarbonate is added, and the biphasic solution is cooled to 0° C. During the addition of phosgene (1.93 M in toluene, 1.0 mL), stirring is stopped. Immediately afterward, stirring is resumed for 15 min with the reaction mixture at 0° C. The layers are separated, the organics dried over solid magnesium sulfate and concentrated to approximately 5 mL of solution. 5-tert-Butyl-3-methanesulfonamido-2-methoxyaniline (Example 4) (0.9 mmol) in dichloromethane (5 mL) is added, and the reaction mixture is stirred overnight at ambient temperature. The solvent is removed by rotary evaporation and the resulting product purified by flash chromatography over silica gel with a suitable elutant such as CH$_2$Cl$_2$:MeOH (95:5) to give the title compound.

EXAMPLE 9

1-[5-tert-butyl-3-methylcarbamoyl-2-methoxyphenyl]-3-[4-(4-pyridinyloxy)-naphthalen-1-yl]-urea

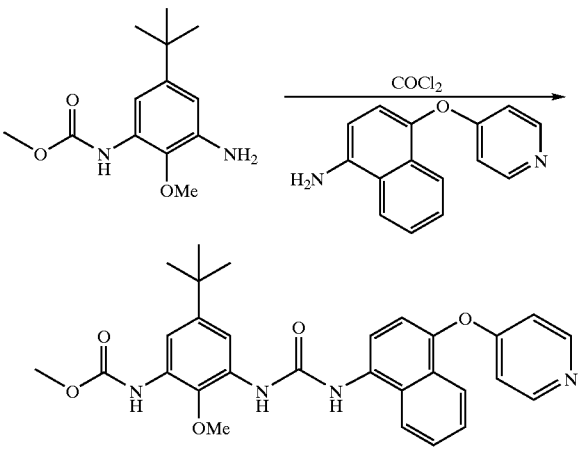

1-Amino-4-(4-pyridinyloxy)naphthalene (Example 6) (1.0 mmol) is dissolved in dichloromethane (15 mL). An equal volume of sat. aqueous sodium bicarbonate is added, and the biphasic solution is cooled to 0° C. During the addition of phosgene (1.93 M in toluene, 1.0 mL), stirring is stopped. Immediately afterward, stirring is resumed for 15 min with the reaction mixture at 0° C. The layers are separated, the organics dried over solid magnesium sulfate and concentrated to approximately 5 mL of solution. 5-tert-Butyl-3-methylcarbamoyl-2-methoxyaniline (Example 3) (0.9 mmol) in dichloromethane (5 mL) is added, and the reaction mixture is stirred overnight at ambient temperature. The solvent is removed by rotary evaporation and the resulting product purified by flash chromatography over silica gel with a suitable elutant such as $CH_2Cl_2$:MeOH (95:5) to give the title compound.

EXAMPLE 10

Synthesis of 4-(4-amino-naphthalen-1-yloxy)-pyridine-2-carboxylic acid methyl ester

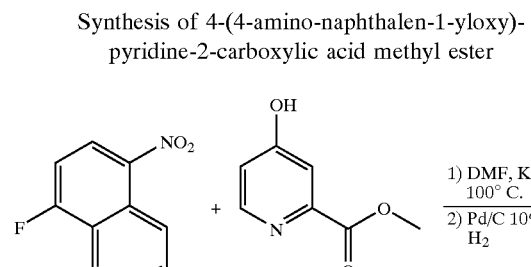

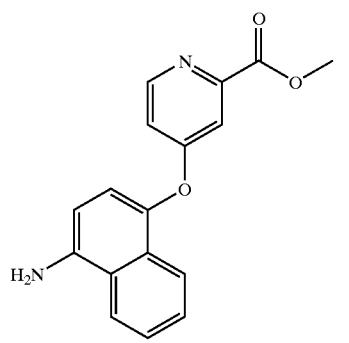

To a solution of 1-fluoro-4-nitro-naphthalene (1.0 g, 5.24 mmol) in dry DMF (22 mL) was added 4-hydroxy-pyridine-2-carboxylic acid methyl ester (0.993 g, 5.24 mmol) and $K_2CO_3$ (7.24 g, 52.4 mmol). The resulting yellow suspension was stirred at 100° C. under argon for five h. After cooling to room temperature, the solution was diluted with $CH_2Cl_2$ (62 mL) and 10% Pd/C (1 g) was added. The suspension was stirred under a $H_2$ balloon for 72 h. The reaction was then filtered through a plug of diatomaceous earth and rinsed with EtOAc (150 mL) and extracted with $H_2O$ (3×100 mL), brine (1×100 mL) and dried over $MgSO_4$. The solvent was removed via rotary evaporation and the resulting oil was applied to a flash silica column eluting with MeOH:$CH_2Cl_2$ (2:98) to provide the title compound (800 mg, 52%).

EXAMPLE 11

Synthesis of 4-{4-[3-(5-tert-butyl-3-methanesulfonylamino-2-methoxy-phenyl)-ureido]-naphthalen-1-yloxy}-pyridine-2-carboxylic acid methyl ester

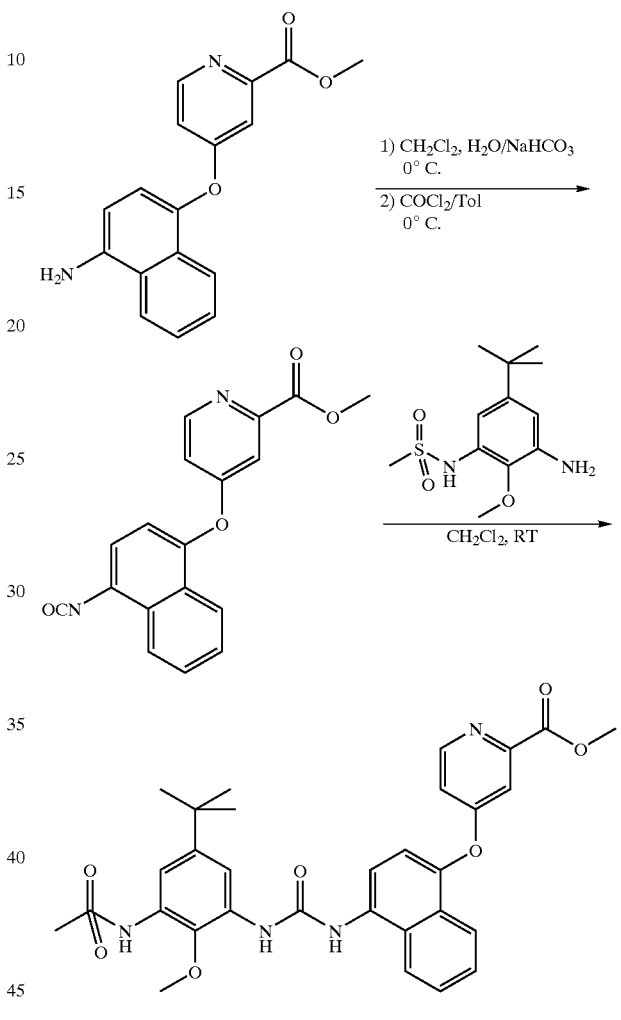

To a solution of 4-(4-amino-naphthalen-1-yloxy)-pyridine-2-carboxylic acid methyl ester (Example 10) (0.6093 g, 2.07 mmol) in $CH_2Cl_2$ (103 mL) and $H_2O$/NaHCO$_3$ (103 mL) cooled to 0° C. for 30 min in a sealed flask was injected COCl$_2$/toluene (40 mL, 20.7 mmol) into the $CH_2Cl_2$ layer. The solution was stirred at 0° C. for an additional 30 min. The reaction mixture was poured into a separatory funnel and the $CH_2Cl_2$ layer was drained. The aqueous layer was extracted with $CH_2Cl_2$ (1×80 mL). The solvent from combined organic layers was dried over MgSO$_4$ and removed via rotary evaporation to provide the isocyanate as an oil. To the resulting isocyanate was added $CH_2Cl_2$ (18 mL) and 5-tert-butyl-3-methanesulfonamido-2-methoxyaniline (Example 4) (1.13 g, 4.14 mmol). The reaction was stirred 12 h at room temperature. The solvent was removed via rotary evaporation and the resulting oil was applied to a combi-flash chromatography column eluting with MeOH:$CH_2Cl$ (5:95) to give the title compound (861 mg, 70% yield).

EXAMPLE 12

Synthesis of 4-{4-[3-(5-tert-butyl-3-methanesulfonylamino-2-methoxy-phenyl)-ureido]-naphthalen-1-yloxy}-pyridine-2-carboxylic acid

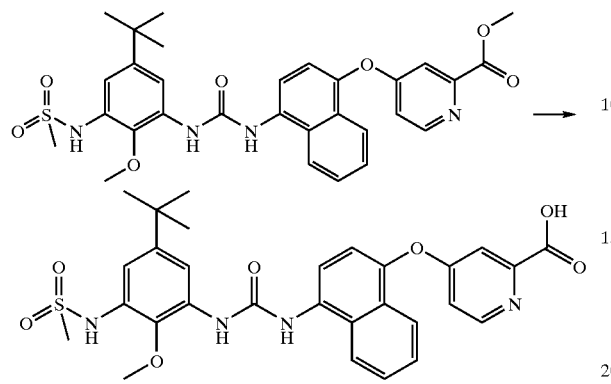

To a solution of 4-{4-[3-(5-tert-butyl-3-methanesulfonylamino-2-methoxy-phenyl)-ureido]-naphthalen-1-yloxy}-pyridine-2-carboxylic acid methyl ester (Example 11) (1.184 g, 2 mmol) in MeOH (12 mL) was added water (2 mL) and LiOH (58 mg, 2.4 mmol). The resulting mixture was stirred at room temperature for 19 h then neutralized with 2N HCl. The resulting suspension was concentrated to dryness and the residual solid triturated with a mixture of methylene chloride and acetonitrile (300 mL, 2:1). The inorganic salt was filtered and the mother liquor concentrated to give the title compound as a dark tan solid (1.04 g, 90%).

EXAMPLE 13

Synthesis of 4-{4-[3-(5-tert-butyl-3-methanesulfonylamino-2-methoxy-phenyl)-ureido]-naphthalen-1-yloxy}-pyridine-2-carboxylic acid dimethylamide

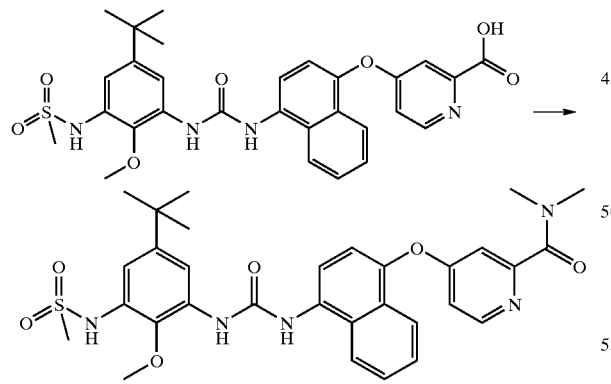

To a cold solution (0° C.) of 4-{4-[3-(5-tert-butyl-3-methanesulfonylamino-2-methoxy-phenyl)-ureido]-naphthalen-1-yloxy}-pyridine-2-carboxylic acid (Example 12) (58 mg, 0.1 mmol) in DMF (1 mL) was added 1-[3-(dimethylamino)propyl]-3-ethylcarbodiimide hydrochloride (23 mg, 0.12 mmol) and triethyl amine (0.070 mL, 0.5 mmol). The solution was allowed to stir at 0° C. for 30 min, then dimethylamine (2M solution in THF, 0.25 mL, 0.5 mmol) was added in one portion. The resulting solution was allowed to stir at room temperature for 12 h. Water (4 mL) was added and the product was extracted with EtOAc, dried over magnesium sulfate and concentrated via rotary evaporation. The resulting crude solid was purified by column chromatography (CH$_2$Cl$_2$:MeOH, 93:7) to give the title compound as a light tan solid (42 mg, 70% yield).

EXAMPLE 14

Synthesis of 4-{4-[3-(5-tert-butyl-2-methoxy-3-methoxycarbonylamino-phenyl)-ureido]-naphthalen-1-yloxy}-pyridine-2-carboxylic acid

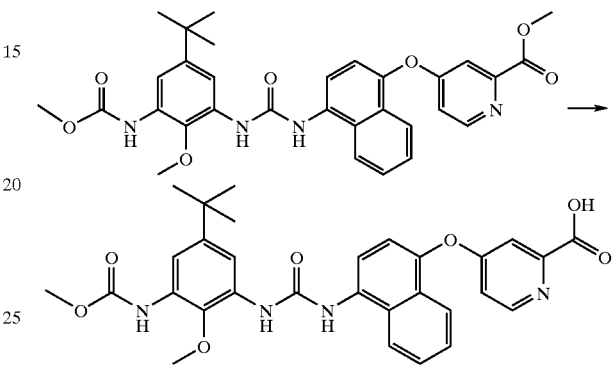

To a solution of 4-{4-[3-(5-tert-butyl-2-methoxy-3-methoxycarbonylamino-phenyl)-ureido]-naphthalen-1-yloxy}-pyridine-2-carboxylic acid methyl ester (1.114 g, 2 mmol) in MeOH (12 mL) was added water (2 mL) and LiOH (58 mg, 2.4 mmol). The resulting mixture was stirred at room temperature for 16 h then neutralized with 2N HCl. The resulting suspension was concentrated to dryness and the residual solid triturated with a mixture of methylene chloride and acetonitrile (300 mL, 2:1). The inorganic salt was filtered and the mother liquor concentrated to give the title compound as a dark tan solid (900 mg, 80%).

EXAMPLE 15

Synthesis of (5-tert-butyl-3-{3-[4-(2-dimethylcarbamoyl-pyridin-4-yloxy)-naphthalen-1-yl]-ureido}-2-methoxy-phenyl)-carbamic acid methyl ester

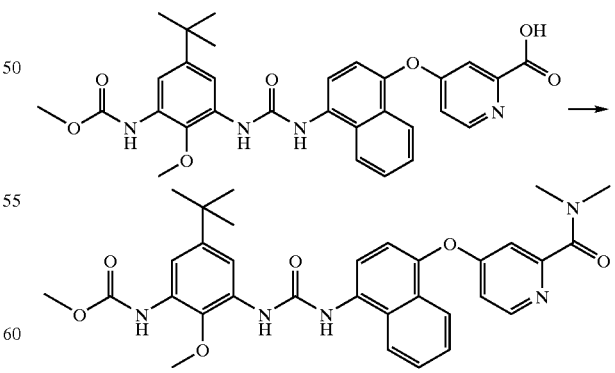

To a cold solution (0° C.) of 4-{4-[3-(5-tert-butyl-2-methoxy-3-methoxycarbonylamino-phenyl)-ureido]-naphthalen-1-yloxy}-pyridine-2-carboxylic acid (Example 14) (56 mg, 0.1 mmol) in DMF (1 mL) was added 1-[3-

(dimethylamino)propyl]-3-ethylcarbodiimide hydrochloride (23 mg, 0.12 mmol) and triethyl amine (0.070 mL, 0.5 mmol). The solution was allowed to stir at 0° C. for 30 min, then dimethylamine (2M solution in THF, 0.25 mL, 0.5 mmol) was added in one portion. The resulting solution was allowed to stir at room temperature for 12 h. Water (4 mL) was added and the product was extracted with EtOAc, dried over magnesium sulfate and concentrated via rotary evaporation. The resulting crude solid was purified by column chromatography (CH$_2$Cl$_2$:MeOH, 95:5) to provide the title compound as a light tan solid (45 mg, 77% yield).

EXAMPLE 16

Synthesis of 4-amino-naphthalene-1-carboxylic acid tert-butyl ester

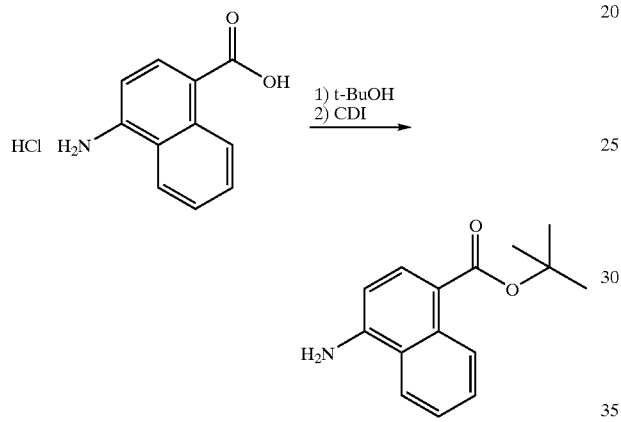

3.6 g (16 mmol) of 4-Amino-naphthalene-1-carboxylic acid hydrochloride, (T. Nakayama et al, Chem. Pharm. Bull, 1984, 32, 3968–3980), was suspended in 44 mL of tert-butyl alcohol and 3.3 mL of triethylamine. To this was added 3.1 g (19 mmol) of carbonyldiimidazole. An exothermic reaction was noted, and the brown solution was stirred at room temperature for 12 h. After this time, the reaction was diluted with EtOAc, filtered through diatomaceous earth and concentrated in vacuo. Purification on silica gel, eluting with 20% EtOAc-hexanes provided 1.1 g of 4-amino-naphthalene-1-carboxylic acid tert-butyl ester as an off-white solid (29%).

EXAMPLE 17

Synthesis of 4-[3-(5-tert-butyl-3-methanesulfonylamino-2-methoxy-phenyl)-ureido]-naphthalene-1-carboxylic acid

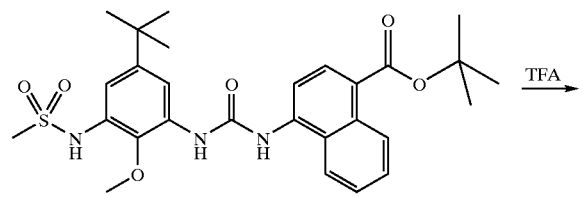

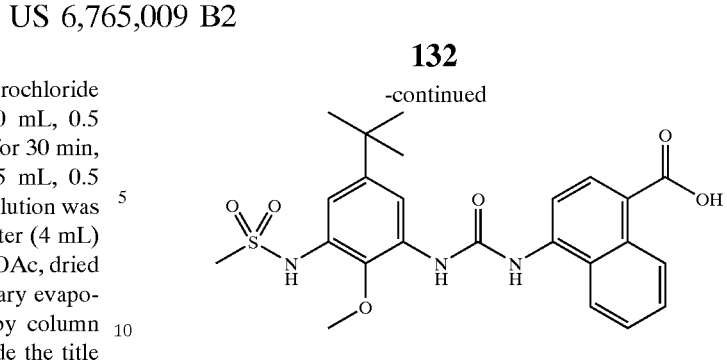

To a 0° C. solution of 10 mL of TFA was added 878 mg (1.9 mmol) of 4-[3-(5-tert-butyl-3-methanesulfonylamino-2-methoxy-phenyl)-ureido]-naphthalene-1-carboxylic acid tert-butyl ester. The clear, light gold reaction was allowed to warm to room temperature, and kept there for 1 h. After this time, the reaction was concentrated in vacuo, and then diluted with toluene. The toluene was then removed in vacuo and the pale white solid was triturated with ether to provide 682 mg (89%) of the title compound.

EXAMPLE 18

Synthesis of (4-{4-[3-(5-tert-butyl-3-methanesulfonylamino-2-methoxy-phenyl)-ureido]-naphthalene-1-carbonyl}-morpholin-2-yl)-acetic acid methyl ester

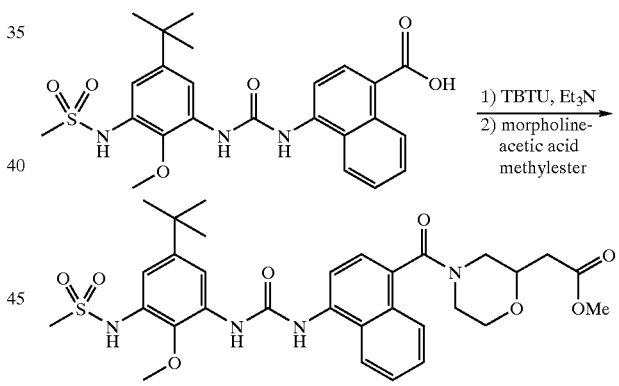

95 mg (0.24 mmol) of 4-[3-(5-tert-butyl-3-methanesulfonylamino-2-methoxy-phenyl)-ureido]-naphthalene-1-carboxylic acid (Example 17) was dissolved in 1 mL of DMF. To this clear solution was added sequentially, 139 mg (0.44 mmol) of TBTU, and 102 microL (0.73 mmol) of triethylamine. The clear yellow solution was stirred for 5 min, then 50 mg (0.31 mmol) of morpholin-2-yl-acetic acid methyl ester (Loftus, F. Syn. Commun. 1980, 10, 59) was added. The reaction was stirred overnight, then concentrated in vacuo. The resulting amber oil was extracted with EtOAc and water, brine, and then dried over magnesium sulfate. Concentration in vacuo provide an amber oil which was purified on silica gel, eluting with 5% MeOH-methylene chloride to provide 93 mg (72%) of the title compound as a viscous oil.

EXAMPLE 19

Synthesis of N-(5-tert-butyl-3-{3-[4-(4-hydroxy-piperidine-1-carbonyl)-naphthalen-1-yl]-ureido}-2-methoxy-phenyl)-methanesulfonamide

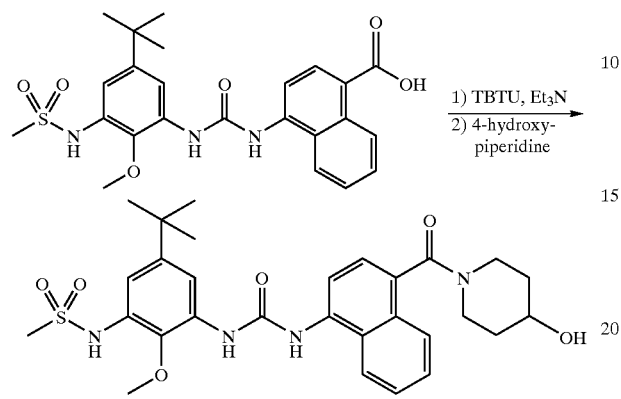

85 mg (0.22 mmol) of 4-[3-(5-tert-butyl-3-methanesulfonylamino-2-methoxy-phenyl)-ureido]-naphthalene-1-carboxylic acid (Example 17) was dissolved in 1 mL of DMF. To this clear solution was added sequentially, 92 mg (0.294 mmol) of TBTU, and 82 microL (0.59 mmol) of triethylamine. The clear yellow solution was stirred for 5 min, then 33 mg (0.33 mmol) of 4-hydroxypiperidine was added. The reaction was stirred overnight, then concentrated in vacuo. The resulting amber oil was extracted with EtOAc and water, brine, and then dried over magnesium sulfate. Concentration in vacuo provided an amber oil which was purified on silica gel, eluting with with 33% EtOAc-hexane to provide 57 mg (54%) of the title compound as a pale white solid.

EXAMPLE 20

Synthesis of N-(5-tert-Butyl-2-methoxy-3-{3-[4-(2-isopropyl-6-methylpyrimidin-4-yloxy)-naphthalen-1-yl]-ureido}-phenyl)-methanesulfonamide

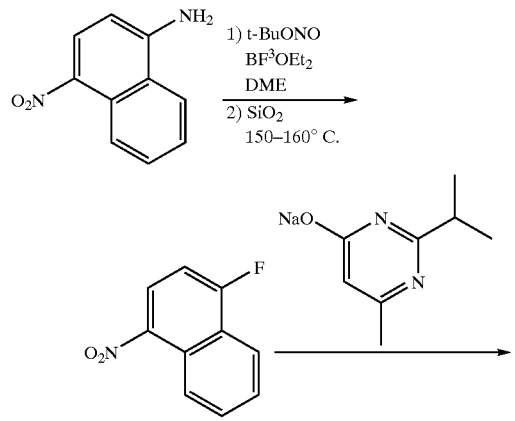

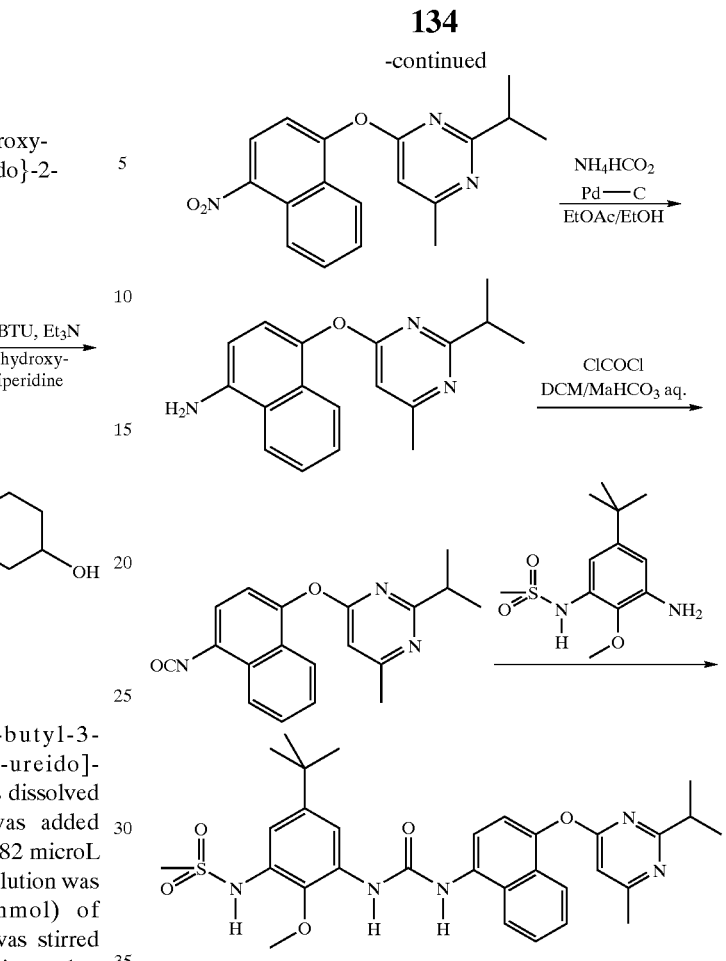

Boron trifluoride etherate (4.0 mL, 31.1 mmol, 1.5 equiv.) was cooled in an ice bath, and under inert atmosphere, 4-amino-1-nitronaphthalene (3.9 g, 20.7 mmol, 1 equiv.) dissolved in 100 mL anhydrous DME was added slowly, over 10 min. Stirring continued for 15 min and then tert-butyl nitrite (3.0 mL, 24.8 mmol, 1.2 equiv.) was added dropwise via syringe. The ice bath was removed and the mixture was stirred at room temperature for 1.5 h. A precipitate of golden green color formed. The mixture was then re-cooled to 0° C. and the precipitate was collected via vacuum filtration, providing 5.1 g (17.7 mmol, 86%) of the 4-nitro-naphthalene diazonium tetrafluoroborate salt.

The diazonium salt from above (408 mg, 1.42 mmol, 1 equiv.) was mixed with silica gel (63–200 micron, 2500 mg) and rendered homogeneous by light mixing in a mortar. This mixture was placed in a round-bottom flask equipped with a mechanical stirrer and a condenser, and heated to 150–170° C. for 0.5 h. The mixture turned dark. The solid mixture was allowed to cool back to room temperature and was placed on top of a short plug of silica gel, the transfer being aided by some hexanes solvent. The pure 4-fluoro-1-nitronaphthalene product was eluted with 10% EtOAc in hexanes. After removal of the solvents in vacuo, 190 mg of product (0.99 mmol, 70% yield) was collected as a yellow-orange solid.

2-Isopropyl-6-methyl-4-pyrimidinol (264 mg, 1.74 mmol, 1.1 equiv.) was dissolved in 2.5 mL anhydrous DMSO. Sodium tert-butoxide (159 mg, 1.66 mmol, 1.05 equiv.) was added in one portion and the mixture was left stirring for 15 min at room temperature. Solid 4-fluoro-1-nitro-naphthalene was then added in one portion and the mixture was gently heated to 60° C. while stirring for 4 h. A color change from orange to green was noted. Saturated aqueous sodium bicarbonate solution was then added and the product extracted 3 times with EtOAc. The combined organic extracts were washed once with water and with brine, dried ($Na_2SO_4$) and filtered. The volatiles were removed in vacuo to afford 459 mg (1.42 mmol, 90%) of the nitronaphthyl-pyrimidinyl ether as a waxy orange solid. The material was used without purification for the next step.

The crude nitronaphthyl-pyrimidinyl ether from above (459 mg, 1.42 mmol, 1 equiv.) was taken up in 35 mL EtOAc and 35 mL EtOH. Ammonium formate was added (537 mg, 8.52 mmol, 6 equiv.) as well as 400 mg of 10% palladium-on-carbon. The reaction mixture was heated to a gentle reflux for one h, cooled back to room temperature, filtered through diatomaceous earth and the volatiles were removed in vacuo. The crude product was purified by chromatography on $SiO_2$, eluting with 20–40% EtOAc in hexanes. The desired aminonaphthyl-pyrimidyl ether was isolated as a yellow foam (176 mg, 0.6 mmol, 42% for 2 steps).

The aminonaphthyl-pyrimidinyl ether from above (104 mg, 0.36 mmol, 1 equiv.) was dissolved in 20 mL dichloromethane and 20 mL saturated aqueous sodium bicarbonate solution was added. The mixture was cooled to 0° C. Without stirring, phosgene (2.0 M in toluene, 0.62 mL, 1.24 mmol, 3.5 equiv.) was added in one portion to the organic layer via syringe. After 15 min the layers were separated and the aqueous phase was extracted with one portion of dichloromethane. The combined organics were dried ($Na_2SO_4$), filtered and the majority of the solvent was removed in vacuo. To this isocyanate residue was immediately added a solution of 5-tert-butyl-3-methanesulfonamido-2-methoxyaniline (Example 4) (97 mg, 0.36 mmol, 1 equiv.) in 2.5 mL anhydrous THF. The mixture was left stirring at room temperature overnight, then MeOH was added and the solvents removed in vacuo. A purple foam was obtained, which was purified by column chromatography on $SiO_2$, eluting with 0–10% MeOH in dichloromethane. Finally recrystallization from acetonitrile/water afforded 45 mg (0.08 mmol, 21% yield) of the title compound as a white solid.

Using procedures analogous to Example 20, the following compound was also prepared:

N-(5-tert-Butyl-3-{3-[4-(2,6-dimethyl-pyrimidin-4-yloxy)-naphthalen-1-yl]-ureido}-2-methoxy-phenyl)-methanesulfonamide

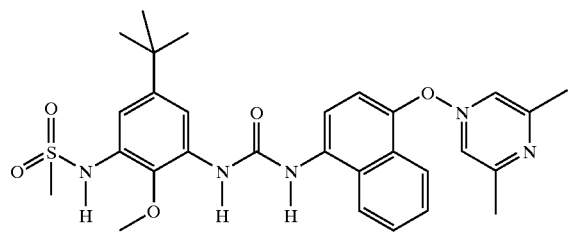

EXAMPLE 21

Synthesis of N-(5-tert-butyl-2-methoxy-3-{3-[4-(2-oxo-2H-pyran-4-yloxy)-naphthalen-1-yl]-ureido}-phenyl)-methanesulfonamide

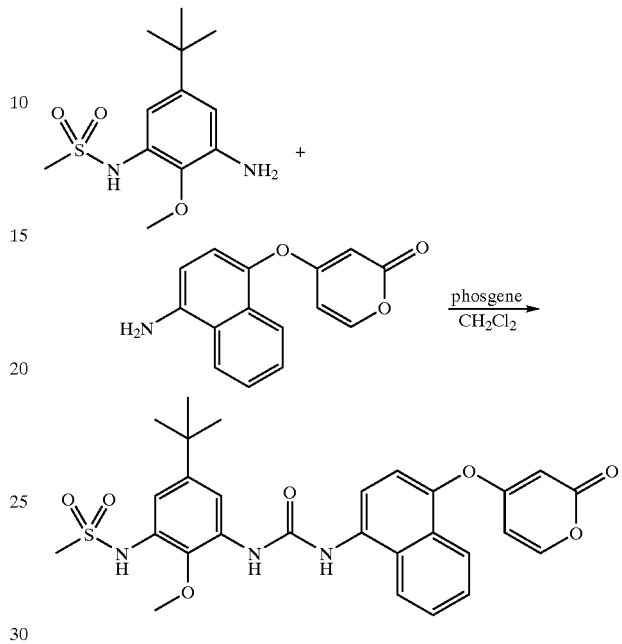

To a suspension of NaH (0.070 g of 60% oil dispersion) in 5 mL of anhydrous THF at 0° C. was added (4-hydroxy-naphthalen-1-yl)-carbamic acid tert-butyl ester (0.414 g) (Example 5). The mixture was stirred 20 min, then 4-chloro-2H-pyran-2-one (*Helvitica Chemica. Acta,* 1990, 73, 883) (0.208 g) was added and the reaction stirred 5 h at 0° C. Removal of the volatiles in vacuo provided a residue which was purified by flash chromatography on silica gel eluting with 33% EtOAc in hexanes. Concentration of the product rich fractions provided [4-(2-oxo-2H-pyran-4-yloxy)-naphthalen-1-yl]-carbamic acid tert-butyl ester.

A mixture of [4-(2-oxo-2H-pyran-4-yloxy)-naphthalen-1-yl]-carbamic acid tert-butyl ester (0.287 g) and HCl (2 mL of a 4N solution in dioxane) in 4 mL of dioxane was stirred overnight, diluted with ether and filtered. The filtrate was dried providing 4-(4-amino-naphthalen-1-yloxy)-pyran-2-one hydrochloride salt.

To 4-(4-amino-naphthalen-1-yloxy)-pyran-2-one hydrochloride salt (0.0468 g) in 2 mL $CH_2Cl_2$ and 2 mL of saturated $NaHCO_3$ at 0° C. was added phosgene (0.21 mL of a 1.9 M solution in toluene). The mixture was stirred rapidly for 10 min, the organic layer dried ($MgSO_4$) and the volatiles removed in vacuo. The residue was diluted with 2 mL of THF and added to 5-tert-butyl-3-methanesulfonamido-2-methoxyaniline (0.044 g) (Example 4). The mixture was stirred overnight and purified by flash chromatography on silica gel eluting with 25% hexanes in EtOAc. Concentration in vacuo of the product rich fractions provided the title compound, mp185–187° C.

Assessment of Biological Properties
Inhibition of TNF Production in THP Cells

The inhibition of cytokine production can be observed by measuring inhibition of TNFα in lipopolysaccharide stimulated THP cells (for example, see W. Prichett et al., 1995, *J. Inflammation,* 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was nonsterile. Initial stock solutions were made in DMSO followed by dilution into RPMI 1640 2-fold higher than the desired final assay concentration. Confluent THP.1 cells ($2\times10^6$ cells/mL, final conc.; American Type Culture Company, Rockville, Md.) were added to 96 well polypropylene round bottomed culture plates (Costar 3790; sterile) containing 125 μL test compound (2 fold concentrated) or DMSO vehicle (controls, blanks). DMSO concentration did not exceed 0.2% final. Cell mixture was allowed to preincubate for 30 min, 37° C., 5% $CO_2$ prior to stimulation with lipopolysaccharide (LPS; 1 μg/mL final; Siga L-2630, from *E.coli* serotype 0111 .B4; stored as 1 mg/mL stock in endotoxin screened distilled $H_2O$ at −80° C.). Blanks (unstimulated) received $H_2O$ vehicle; final incubation volume was 250 μl. Overnight incubation (18–24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated $IC_{50}$ value is the concentration of the test compound that caused a 50% decrease in the maximal TNFα production. Preferred compounds from those found in Table I and in the examples will exhibit an $IC_{50}$<10 uM.

Inhibition of Other Cytokines

By similar methods using peripheral blood monocytic cells, appropriate stimuli, and commercially available ELISA kits (or other method of detection such as radioimmunoassay), for a particular cytokine, inhibition of IL-1, GM-CSF, IL-6 and IL-8 can be demonstrated (for example, see J. C. Lee et al., 1988, *Int. J. Immunopharmacol.*, 10, 835).

What is claimed is:

1. A 1,4-disubstituted benzo-fused compound of the formula (I):

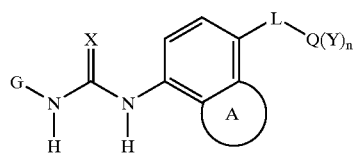

wherein:

ring A is:

fused saturated or unsaturated ring containing 3–5 carbon atoms wherein ring A or the phenyl ring to which it is fused is optionally substituted by one or more a $C_{1-6}$ branched or unbranched alkyl optionally partially or fully halogenated, acetyl, aroyl, $C_{1-6}$ branched or unbranched alkoxy optionally partially or fully halogenated, halogen, methoxycarbonyl, phenylsulfonyl, hydroxy, amino, mono- or di-($C_{1-4}$ alkyl) amino, mono- or di-($C_{1-4}$ alkyl)amino-S(O)$_2$, cyano, nitro or $H_2NSO_2$;

G is:

phenyl, naphthyl, benzocyclobutanyl, dihydronaphthyl, tetrahydronaphthyl, benzocycloheptanyl, benzocycloheptenyl, indanyl, indenyl;

wherein G is substituted by one $R_3$ and further substituted by one or more $R_1$ or $R_2$;

L is:

a) —O—; —NH—; >C(O); >C(S);

$C_{1-10}$ saturated or unsaturated branched or unbranched carbon chain;

wherein one or more carbon atoms are optionally independently replaced by heteroatoms chosen from O, N and S(O)$_m$; and wherein said L is optionally substituted with 0–2 oxo groups, one or more $C_{1-4}$ branched or unbranched alkyl optionally substituted by one or more halogen atoms, hydroxy, amino or imino; or b) >CR$_x$R$_y$ wherein R$_x$ and R$_y$ are each independently hydrogen, $C_{1-4}$alkyl, heterocycleC$_{0-4}$ alkyl, heteroarylC$_{0-4}$ alkyl or arylC$_{0-4}$ alkyl;

Q is: pyrimidinyl, optionally substituted with one to three $C_{1-6}$ alkyl, phenyl, $C_{1-6}$ alkoxy or hydroxy;

$R_1$ is independently:

$C_{3-10}$ branched or unbranched alkyl optionally partially or fully halogenated, and optionally substituted with one to three $C_{3-10}$ cycloalkyl, hydroxy, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl; each of the aforementioned being optionally substituted with 1 to 5 halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated and NH$_2$C(O) or mono- or di($C_{1-3}$)alkylaminocarbonyl;

cyclopropyl, cyclobutyl, cyclopentanyl, cyclohexanyl, cycloheptanyl, bicyclopentanyl, bicyclohexanyl or bicycloheptanyl, which are optionally partially or fully halogenated and optionally substituted with one to three $C_{1-3}$ alkyl groups optionally partially or fully halogenated, cyano, hydroxyC$_{1-3}$ alkyl or aryl;

$C_{3-10}$ branched or unbranched alkenyl optionally partially or fully halogenated, and optionally substituted with one to three $C_{1-5}$ branched or unbranched alkyl, phenyl, naphthyl, pyridinyl, pyrimidinyl, pyrazinyl, pyridazinyl, pyrrolyl, imidazolyl, pyrazolyl, thienyl, furyl, isoxazolyl or isothiazolyl, each of the aforementioned are optionally substituted with 1 to 5 halogen, $C_{1-6}$ branched or unbranched alkyl optionally partially or fully halogenated, cyclopropyl, cyclobutyl, cyclopentanyl, cyclohexanyl, cycloheptanyl, bicyclopentanyl, bicyclohexanyl or bicycloheptanyl, hydroxy, cyano, $C_{1-3}$ alkoxy optionally partially or fully halogenated, NH$_2$C(O) or mono- or di($C_{1-3}$) alkylaminocarbonyl;

cyclopentenyl, cyclohexenyl, cyclohexadienyl, cycloheptenyl, cycloheptadienyl, bicyclohexenyl or bicycloheptenyl, each optionally substituted with one to three $C_{1-3}$ alkyl groups;

N-morpholinyl;

cyano, halogen;

methoxycarbonyl, ethoxycarbonyl or propoxycarbonyl;

silyl containing three $C_{1-4}$ independently branched or unbranched alkyl groups optionally partially or fully halogenated;

$C_{1-6}$ branched or unbranched alkyl-C(O), $C_{1-6}$ branched or unbranched-S(O)$_m$;

$C_{2-6}$ alkynyl branched or unbranched carbon chain optionally partially or fully halogenated, wherein one or more methylene groups are optionally replaced by O, NH and S(O)$_m$ and wherein said alkynyl group is optionally independently substituted with 0–2 oxo groups, pyrroldinyl, pyrrolyl, one or more C$_{1-4}$ branched or unbranched alkyl optionally substituted by one or more halogen atoms, nitrile, morpholinyl, piperidinyl, piperazinyl, imidazolyl, phenyl, pyridinyl, tetrazolyl, or C$_{1-4}$ branched or unbranched alkylamino optionally substituted by one or more halogen atoms;

R$_2$ is independently:
a C$_{1-6}$ branched or unbranched alkyl optionally partially or fully halogenated, acetyl, aroyl, C$_{1-4}$ branched or unbranched alkoxy optionally partially or fully halogenated, halogen, methoxycarbonyl or phenylsulfonyl;
hydroxy, amino, or mono- or di-(C$_{1-4}$ alkyl)amino, cyano, halogen;
OR$_5$;
nitro; or
mono- or di-(C$_{1-4}$ alkyl)amino-S(O)$_2$ optionally partially or fully halogenated, or H$_2$NSO$_2$;

each R$_3$ is independently:
(J)$_p$—L'—S(O)$_m$—NH— or (J)$_p$—L'—O—C(O)—NH—, wherein for R$_3$:
L' is a bond or
C$_{1-10}$ saturated or unsaturated branched or unbranched carbon chain;
wherein one or more carbon atoms are optionally independently replaced by heteroatoms chosen from O, N and S(O)$_m$; and
wherein said L' is optionally substituted with 0–2 oxo groups, one or more C$_{1-4}$ branched or unbranched alkyl optionally substituted by one or more halogen atoms, hydroxy, amino or imino;

J is:
cyclopropyl, cyclobutyl, cyclopentyl, cyclohexyl, cycloheptyl, bicyclopentanyl, bicyclohexanyl or bicycloheptanyl;
cyclobutenyl, cyclopentenyl, cyclohexenyl, cyclohexadienyl, cycloheptenyl, cycloheptadienyl, bicyclohexenyl or bicycloheptenyl;
phenyl, naphthyl, morpholinyl, pyridinyl, piperidinyl, piperazinyl, pyrimidinyl, pyrazinyl, pyridazinyl, pyrrolyl, pyrrolidinyl, imidazolyl, pyrazolyl, thiazolyl, oxazoyl, [1,3,4]oxadiazol, triazolyl, tetrazolyl, thienyl, furyl, dioxolanyl, tetrahydrofuryl, isoxazolyl, isothiazolyl, quinolinyl, isoquinolinyl, indolyl, benzimidazolyl, benzofuranyl, benzoxazolyl, benzisoxazolyl, benzopyrazolyl, benzothiofuranyl, cinnolinyl, pterindinyl, phthalazinyl, naphthypyridinyl, quinoxalinyl, quinazolinyl, purinyl or indazolyl, a fused aryl selected from benzocyclobutanyl, indanyl, indenyl, dihydronaphthyl, tetrahydronaphthyl, benzocycloheptanyl and benzocycloheptenyl, or J is a fused heteroaryl selected from cyclopentenopyridinyl, cyclohexanopyridinyl, cyclopentanopyrimidinyl, cyclohexanopyrimidinyl, cyclopentanopyrazinyl, cyclohexanopyrazinyl, cyclopentanopyridazinyl, cyclohexanopyridazinyl, cyclopentanoquinolinyl, cyclohexanoquinolinyl, cyclopentanoisoquinolinyl, cyclohexanoisoquinolinyl, cyclopentanoindolyl, cyclohexanoindolyl, cyclopentanobenzimidazolyl, cyclohexanobenzimidazolyl, cyclopentanobenzoxazolyl, cyclohexanobenzoxazolyl, cyclopentanoimidazolyl, cyclohexanoimidazolyl, cyclopentanothienyl and cyclohexanothienyl;
each J is optionally substituted by one to three R$_4$;
each R$_4$ is independently
C$_{1-6}$ alkyl, arylC$_{0-6}$ alkyl, heterocycleC$_{0-6}$ alkyl, heteroarylC$_{0-6}$ alkyl each optionally substituted by halogen, hydroxy, carboxy, oxo, nitro or nitrile, or R$_4$ is amino optionally mono- or di-substituted by C$_{1-6}$ alkyl, C$_{0-6}$ alkylaryl, C$_{0-6}$ alkylheterocycle or C$_{0-6}$ alkylheteroaryl, halogen, hydroxy, carboxy, oxo, nitro or nitrile;
wherein if p is 0, then L' cannot be a bond;

each R$_5$ or R$_6$ is independently:
hydrogen, arylC$_{0-3}$ alkyl optionally subtituted by halogen, C$_{1-3}$ alkyl or diC$_{1-5}$ alkyl amino, or R$_5$ or R$_6$ are C$_{1-3}$ acyl, aroyl or C$_{1-6}$ branched or unbranched alkyl optionally substituted by C$_{1-5}$ alkoxy, hydroxy, mono- or di-C$_{1-3}$alkylaminocarbonyl or mono or diC$_{1-3}$ alkyl amino wherein said C$_{1-6}$ alkyl optionally partially or fully halogenated;
or R$_5$ and R$_6$ taken together optionally form a heterocyclic or heteroaryl ring;

Y, which covalently attached to Q, is
a bond, —O—, >C(O), —NH—, —C(O)—NH—, —S—, C$_{1-5}$ alkyl branched or unbranched, C$_{1-3}$ alkyl(OH), C$_{2-5}$ alkenyl, C$_{1-3}$ acyl, heterocycle selected from morpholinyl, piperzinyl, piperidinyl, pyrrolidinyl or tetrahydrofuryl, heteroaryl selected from pyridinyl, pyrimidinyl, pyrazinyl, pyridazinyl, pyrrolyl, imidazolyl, pyrazolyl, thienyl, furyl, isoxazolyl, thiazolyl, oxazolyl, triazolyl, tetrazolyl, isothiazolyl, quinolinyl, isoquinolinyl, indolyl, benzimidazolyl, benzofuranyl, benzoxazolyl, benzisoxazolyl, benzopyrazolyl, benzothiofuranyl, quinoxalinyl, quinazolinyl or indazolyl or aryl each alkyl, alkenyl, acyl, heterocycle, heteroaryl and aryl are optionally substituted by one to three hydroxy, oxo, C$_{1-4}$ alkyl, C$_{1-3}$ alkoxy, C$_{1-4}$ acyl, C$_{1-5}$ alkoxycarbonyl, NR$_5$R$_6$ or NR$_5$R$_6$—C(O)—;
wherein each Y is optionally further covalently attached to NR$_5$R$_6$, C$_{1-4}$ alkyl, C$_{3-7}$ cycloalkylC$_{0-4}$ alkyl, C$_{1-4}$ alkoxy, aryloxy, hydroxy, arylC$_{0-4}$ alkyl, heteroarylC$_{0-4}$ alkyl or heterocycleC$_{0-4}$ alkyl as wherein the heteroaryl and heterocycle moieties are as hereinabove described for Y and the heterocycle, heteroaryl and aryl moieties are optionally substituted by one to three hydroxy, oxo, C$_{1-3}$ alkyl, C$_{1-3}$ alkoxy, C$_{1-5}$ alkoxycarbonyl, NR$_5$R$_6$ or NR$_5$R$_6$—C(O)—;
m, n and p are each independently 0, 1 or 2;
X is O or S; and
the pharmaceutically acceptable derivatives thereof.

2. The compound according to claim 1 wherein:
ring A and the phenyl ring to which it is fused form:

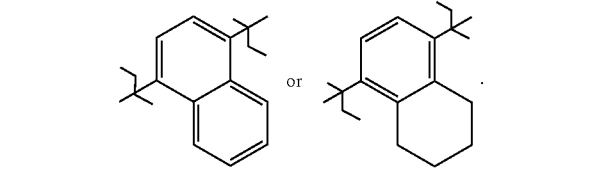

3. The compound according to claim 2 wherein:
n is 0;
ring A and the phenyl ring to which it is fused form:

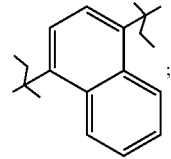

L is:
—O—, >C(O), >C(S), —OCH$_2$—, —CH$_2$—, —CH$_2$CH$_2$—, —CH$_2$CH$_2$CH$_2$—, —C(CH$_3$)$_2$—, —CH(OH)—, —CH$_2$CH(OH)—, —CH(OH)CH$_2$—,

—OCH$_2$CH$_2$—, —OCH$_2$CH$_2$CH$_2$—, —OCH$_2$CH$_2$(CH$_3$)—, —OCH$_2$(CH$_3$)CH$_2$—, —OCH$_2$C(O)—, —CH=CH—CH$_2$— or —CH=CHCH$_2$CH$_2$, —NH—, —NHCH$_2$—, —NHCH$_2$CH$_2$—, —S(O)$_m$—, —S(O)$_m$CH$_2$—, —S(O)$_m$CH$_2$CH$_2$ and —S(O)$_m$CH$_2$CH$_2$CH$_2$—;

Q is:
pyrimidinyl mono- or disubstituted by C$_{1-3}$ alkyl or phenyl;
R$_1$ is independently:
C$_{3-5}$ branched or unbranched alkyl optionally partially or fully halogenated and optionally substituted with one to three C$_{3-6}$ cycloalkyl, hydroxy or phenyl; N-morpholinyl; cyclopropyl, cyclobutyl, cyclopentanyl, cyclohexanyl, bicyclopentanyl or bicyclohexanyl optionally partially or fully halogenated and optionally substituted with one to three C$_{1-3}$ alkyl groups optionally partially or fully halogenated, cyano, hydroxyC$_{1-3}$ alkyl or phenyl;
R$_2$ is independently:
a C$_{1-6}$ branched or unbranched alkyl optionally partially or fully halogenated or C$_{1-4}$ branched or unbranched alkoxy optionally partially or fully halogenated
R$_3$ is
(J)$_{0-1}$—L'—S(O)$_m$—NH— or (J)$_{0-1}$—L'—O—C(O)—NH—,
wherein for R$_3$;
L' is
a bond, C$_{1-5}$ alkyl, hydroxy C$_{1-5}$ alkyl, C$_{2-4}$ alkenyl, amidoC$_{1-5}$ alkyl;
J is:
cyclopropyl, cyclobutyl, cyclopentyl, cyclohexyl, cycloheptyl, bicyclopentanyl, bicyclohexanyl or bicycloheptanyl, phenyl, naphthyl, morpholinyl, piperidinyl, piperazinyl, pyridinyl, pyrimidinyl, pyrazinyl, pyridazinyl, pyrrolyl, pyrrolidinyl, imidazolyl, pyrazolyl, thiazolyl, oxazolyl, thienyl, furyl, dioxolanyl, tetrahydrofuryl, isoxazolyl and isothiazolyl,
cyclobutenyl, cyclopentenyl, cyclohexenyl, cyclohexadienyl, cycloheptenyl, cycloheptadienyl, bicyclohexenyl or bicycloheptenyl;
each of the above J is optionally substituted by one to two R$_4$;
R$_4$ is oxo or mono- or di-C$_{1-3}$ alkylamino;
Y is not present;
m is 2;
and
X is O.

4. The compound according to claim 3 wherein:
G is
phenyl, or naphthyl, wherein G is substituted by one R$_3$ and further substituted by one to three R$_1$ or R$_2$;
L' is
a bond, C$_{1-5}$ alkyl, hydroxy C$_{1-5}$ alkyl, C$_{2-4}$ alkenyl, amidoC$_{1-5}$ alkyl.

5. The compound according to claim 4 wherein:
G is phenyl wherein G is substituted by one R$_3$ and further substituted by one to three R$_1$ or R$_2$;
L is: —O—, >C(O), —C(CH$_3$)$_2$—, —O—CH$_2$—, —CH$_2$—, —OCH$_2$CH$_2$—, —OCH$_2$CH$_2$CH$_2$—, —OCH$_2$CH$_2$(CH$_3$)—, —OCH$_2$(CH$_3$)CH$_2$—, —NH—, —NHCH$_2$—, —NHCH$_2$CH$_2$—, —S(O)$_m$—, —S(O)$_m$CH$_2$—, —S(O)$_m$CH$_2$CH$_2$—, —S(O)$_m$CH$_2$CH$_2$CH$_2$—, —CH$_2$CH$_2$—, —CH$_2$CH$_2$CH$_2$— or —OCH$_2$C(O)—;
each R$_1$ is independently:
C$_{3-5}$ branched or unbranched alkyl optionally partially or fully halogenated and optionally substituted with phenyl or R$_1$ is N-morpholinyl;

cyclopropyl, cyclopentanyl, cyclohexanyl or bicyclopentanyl optionally substituted with one to three methyl groups optionally be partially or fully halogenated, cyano, hydroxymethyl or phenyl.

6. The compound according to claim 5 wherein:
G is phenyl substituted by one R$_3$ and further independently substituted by one to two R$_1$ or R$_2$;
and
L is:
—O—, >C(O) or —C(CH$_3$)$_2$—;
R$_3$ is
L'—S(O)$_2$—NH or (J)$_{0-1}$—L'—O—C(O)—NH wherein L' is C$_{1-5}$alkyl.

7. The compound according to claim 6 wherein:
R$_1$ is
tert-butyl optionally partially or fully halogenated;
R$_2$ is independently:
C$_{1-3}$ alkyl or C$_{1-3}$ alkoxy;
Q is pyrimidin-4-yl each mono- or di-substituted by methyl or phenyl.

8. The compound according to claim 7 wherein
L is —O—, >C(O) or -C(CH$_3$)$_2$—;
and
R$_3$ is C$_{1-3}$ alkyl-S(O)$_2$—NH— or C$_{1-3}$ alkyl-O—C(O)—NH—.

9. The compound according to claim 8 wherein R$_3$ is CH$_3$—S(O)$_2$—NH— or CH$_3$—O—C(O)—NH—.

10. The compound according to claim 2 wherein:
n is 1;
ring A and the phenyl ring to which it is fused form:

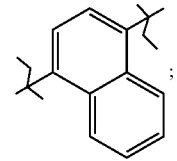

L is:
—O—, —OCH$_2$—, —CH$_2$—, —CH(OH)—, —CH$_2$—CH(OH)—, —CH(OH)CH$_2$—, —OCH$_2$CH$_2$—, —O—CH$_2$CH$_2$CH$_2$—, —OCH$_2$CH$_2$(CH$_3$)—, —OCH$_2$(CH$_3$)CH$_2$—, —CH$_2$CH$_2$—, —CH$_2$CH$_2$CH$_2$—, —OCH$_2$C(O)—, —CH=CHCH$_2$— or —CH=CHCH$_2$CH$_2$—, —NH—, —NHCH$_2$—, —NHCH$_2$CH$_2$—, —S(O)$_m$—, —S(O)$_m$CH$_2$—, —S(O)$_m$CH$_2$CH$_2$— and —S(O)$_m$CH$_2$CH$_2$CH$_2$—;
Q is:
pyrimidinyl;
R$_1$ is independently:
C$_{3-5}$ branched or unbranched alkyl optionally partially or fully halogenated, and optionally substituted with one to three C$_{3-6}$ cycloalkyl, hydroxy and phenyl;
N-morpholinyl;
cyclopropyl, cyclobutyl, cyclopentanyl, cyclohexanyl, bicyclopentanyl or bicyclohexanyl optionally partially or fully halogenated and optionally substituted with one to three C$_{1-3}$ alkyl groups optionally partially or fully halogenated, cyano, hydroxyC$_{1-3}$ alkyl or phenyl;
R$_2$ is independently:
a C$_{1-6}$ branched or unbranched alkyl optionally partially or fully halogenated or C$_{1-4}$ branched or unbranched alkoxy optionally partially or fully halogenated;
R$_3$ is $(J)_{0-1}$—L'—S(O)$_m$NH— or $(J)_{0-1}$—L'—O—C(O)—NH—, wherein for $R_3$:

L' is a bond, $C_{1-5}$ alkyl, hydroxy $C_{1-5}$ alkyl, $C_{2-4}$ alkenyl, amido$C_{1-5}$ alkyl;

J is:

cyclopropyl, cyclobutyl, cyclopentyl, cyclohexyl, cycloheptyl, bicyclopentanyl, bicyclohexanyl or bicycloheptanyl, phenyl, naphthyl, morpholinyl, piperidinyl, piperazinyl, pyridinyl, pyrimidinyl, pyrazinyl, pyridazinyl, pyrrolyl, pyrrolidinyl, imidazolyl, pyrazolyl, thiazolyl, oxazolyl, thienyl, furyl, dioxolanyl, tetrahydrofuryl, isoxazolyl and isothiazolyl, cyclobutenyl, cyclopentenyl, cyclohexenyl, cyclohexadienyl, cycloheptenyl, cycloheptadienyl, bicyclohexenyl or bicycloheptenyl;

each of the above J is optionally substituted by one to two $R_4$;

$R_4$ is oxo or mono- or di-$C_{1-3}$ alkylamino;

Y is a bond, —O—, >C(O), —NH—, —C(O)—NH—, —S—, $C_{1-5}$ alkyl branched or unbranched, $C_{2-5}$ alkenyl, $C_{1-3}$ acyl, $C_{1-3}$ alkyl(OH), heterocycle selected from morpholinyl, piperazinyl, piperidinyl, pyrrolidinyl and tetrahydrofuranyl, heteroaryl selected from pyridinyl, pyrimidinyl, pyrazinyl, pyridazinyl, pyrrolyl, imidazolyl, pyrazolyl, thienyl, furyl, isoxazolyl, thiazolyl, oxazolyl and isothiazolyl or aryl each alkyl, alkenyl, acyl, heterocycle, heteroaryl and aryl are optionally substituted by one to three hydroxy, oxo, $C_{1-3}$ alkyl, $C_{1-3}$ alkoxy, $C_{1-5}$ alkoxycarbonyl, $NR_5R_6$ or $NR_5R_6$—C(O)—;

wherein each Y is further covalently attached to $NR_5R_6$, $C_{1-3}$ alkyl, $C_{3-6}$ cycloalkyl$C_{0-2}$alkyl, hydroxy, $C_{1-3}$ alkoxy, phenoxy, phenyl$C_{0-4}$ alkyl, piperazinyl$C_{0-4}$ alkyl, piperidinyl $C_{0-4}$alkyl, pyrrolidinyl$C_{0-4}$ alkyl, morpholinyl$C_{0-4}$ alkyl, tetrahydrofuranyl$C_{0-4}$ alkyl or pyridinyl $C_{0-4}$alkyl, each abovelisted heterocycle, heteroaryl and phenyl is optionally substituted by one to three hydroxy, oxo, $C_{1-4}$ alkyl, $C_{1-3}$ alkoxy, $C_{1-5}$ alkoxycarbonyl, $NR_5R_6$—C(O)— or $C_{1-4}$ acyl, each $R_5$ and $R_6$ are independently hydrogen, phenyl$C_{0-3}$alkyl optionally subtituted by halogen, $C_{1-3}$ alkyl or di$C_{1-5}$ alkyl amino, or $R_5$ and $R_6$ are $C_{1-2}$ acyl, benzoyl or $C_{1-4}$ branched or unbranched alkyl optionally substituted by $C_{1-4}$ alkoxy, hydroxy or mono or di$C_{1-3}$ alkyl amino;

m is 2;

and

X is O.

11. The compound according to claim 10 wherein: G is phenyl or naphthyl, wherein G is substituted by one $R_3$ and further substituted by one to three $R_1$ or $R_2$;

L' is a bond, $C_{1-5}$ alkyl, hydroxy $C_{1-5}$ alkyl, $C_{2-4}$ alkenyl, amido$C_{1-5}$ alkyl.

12. The compound according to claim 11 wherein:

L is:

—O—, —OCH$_2$—, —CH$_2$—, —CH$_2$CH$_2$—, —CH$_2$CH$_2$CH$_2$—, —OCH$_2$CH$_2$—, —OCH$_2$CH$_2$CH$_2$—, —OCH$_2$CH$_2$(CH$_3$)—, —OCH$_2$(CH$_3$)CH$_2$—, —NH—, —NHCH$_2$—, —NHCH$_2$CH$_2$—, —S(O)$_m$—, —S(O)$_m$CH$_2$—, S(O)$_m$CH$_2$CH$_2$—, —S(O)$_m$CH$_2$CH$_2$CH$_2$— or —OCH$_2$C(O)—;

each $R_1$ is independently:

$C_{3-5}$ branched or unbranched alkyl optionally partially or fully halogenated, and optionally substituted with phenyl;

N-morpholinyl;

cyclopropyl, cyclopentanyl, cyclohexanyl or bicyclopentanyl optionally substituted with one to three methyl groups optionally partially or fully halogenated, cyano, hydroxymethyl or phenyl;

Y is a bond, —O—, —S—, >C(O), —NH—, —C(O)—NH—, —CH(C$_{1-2}$ alkyl)—;

or Y is $C_{1-2}$ alkyl, $C_{1-2}$ alkyl(OH), $C_{2-4}$ alkenyl, $C_{1-2}$ acyl, imidazolyl, pyrazolyl, pyrrolidinyl, thienyl, isoxazolyl, thiazolyl, oxazolyl, isothiazolyl or phenyl each optionally substituted by one to two hydroxy, oxo, $C_{1-3}$ alkyl, $C_{1-3}$ alkoxy, $C_{1-5}$ alkoxycarbonyl, $NR_5R_6$ or $NR_5R_6$—C(O)—;

wherein each Y is further covalently attached to $NR_5R_6$, $C_{1-3}$ alkyl, $C_{3-6}$ cycloalkyl$C_{0-2}$alkyl, hydroxy, $C_{1-3}$ alkoxy, phenoxy, phenyl$C_{0-4}$ alkyl, piperazinyl$C_{0-4}$ alkyl, piperidinyl$C_{0-4}$ alkyl, pyrrolidinyl$C_{0-4}$ alkyl, morpholinyl$C_{0-4}$ alkyl, tetrahydrofuranyl$C_{0-4}$ alkyl or pyridinyl$C_{0-4}$ alkyl each abovelisted heterocycle, heteroaryl or phenyl is optionally substituted by one to two $C_{1-5}$ alkoxycarbonyl, $NR_5R_6$—C(O)—, $C_{1-4}$ alkyl, $C_{1-4}$ acyl or hydroxy;

each $R_5$ and $R_6$ are independently hydrogen, phenyl$C_{0-3}$ alkyl optionally subtituted by halogen or $C_{1-3}$ alkyl, acetyl, benzoyl or $C_{1-4}$ branched or unbranched alkyl optionally substituted by $C_{1-3}$ alkoxy, hydroxy, mono or di$C_{1-3}$ alkyl amino.

13. The compound according to claim 2 wherein:

n is 2;

ring A and the phenyl ring to which it is fused form:

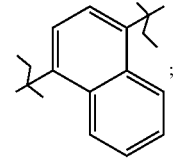

G is phenyl or naphthyl, wherein G is substituted by one $R_3$ and further substituted by one or more $R_1$ or $R_2$;

L is:

—O—, >C(O), —OCH$_2$—, —CH$_2$—, —CH(OH)—, —CH$_2$—CH(OH)—, —CH(OH)CH$_2$—, —OCH$_2$CH$_2$—, —OCH$_2$CH$_2$CH$_2$—, —OCH$_2$CH$_2$(CH$_3$)—, —OCH$_2$(CH$_3$)CH$_2$—, —CH$_2$CH$_2$—, —CH$_2$CH$_2$CH$_2$—, —OCH$_2$C(O)—, —CH═CHCH$_2$— or —CH═CHCH$_2$CH$_2$—, —NH—, —NHCH$_2$—, —NHCH$_2$CH$_2$—, —S(O)$_m$—, —S(O)$_m$CH$_2$—, —S(O)$_m$CH$_2$CH$_2$— and —S(O)$_m$CH$_2$CH$_2$CH$_2$—;

Q is:

pyrimidinyl optionally substituted by one $C_{1-6}$ alkyl or phenyl;

$R_1$ is independently:

$C_{3-5}$ branched or unbranched alkyl optionally partially or fully halogenated, and optionally substituted with one to three $C_{3-6}$ cycloalkyl, hydroxy and phenyl;

N-morpholinyl cyclopropyl, cyclobutyl, cyclopentanyl, cyclohexanyl, bicyclopentanyl or bicyclohexanyl optionally partially or fully halogenated and optionally substituted with one to three $C_{1-3}$ alkyl groups optionally partially or fully halogenated, cyano, hydroxy$C_{1-3}$ alkyl or phenyl;

$R_2$ is independently:

a $C_{1-6}$ branched or unbranched alkyl optionally partially or fully halogenated or $C_{1-4}$ branched or unbranched alkoxy optionally partially or fully halogenated;

R₃ is
(J)₀₋₁—L'—S(O)ₘ—NH— or (J)₀₋₁—L'—O—C(O)—NH—,
wherein for R₃:
L' is
a bond, $C_{1-5}$ alkyl, hydroxy $C_{1-5}$ alkyl, $C_{2-4}$ alkenyl, amido$C_{1-5}$ alkyl;
J is:
cyclopropyl, cyclobutyl, cyclopentyl, cyclohexyl, cycloheptyl, bicyclopentanyl, bicyclohexanyl or bicycloheptanyl, phenyl, naphthyl, morpholinyl, piperidinyl, piperazinyl, pyridinyl, pyrimidinyl, pyrazinyl, pyridazinyl, pyrrolyl, pyrrolidinyl, imidazolyl, pyrazolyl, thiazolyl, oxazolyl, thienyl, furyl, dioxolanyl, tetrahydrofuryl, isoxazolyl and isothiazolyl,
cyclobutenyl, cyclopentenyl, cyclohexenyl, cyclohexadienyl, cycloheptenyl, cycloheptadienyl, bicyclohexenyl or bicycloheptenyl;
each of the above J is optionally substituted by one to two R₄;
R₄ is oxo or mono- or di-$C_{1-3}$ alkylamino;
Y is
a bond, —O—, >C(O), —NH—, —C(O)—NH—, —S—, $C_{1-5}$ alkyl branched or unbranched, $C_{2-5}$ alkenyl, $C_{1-3}$ acyl, $C_{1-3}$ alkyl(OH), heterocycle selected from morpholinyl, piperazinyl, piperidinyl, pyrrolidinyl or tetrahydrofuryl, heteroaryl selected from pyridinyl, pyrimidinyl, pyrazinyl, pyridazinyl, pyrrolyl, imidazolyl, pyrazolyl, thienyl, furyl, isoxazolyl, thiazolyl, oxazolyl, indolyl or isothiazolyl or aryl each alkyl, alkenyl, acyl, heterocycle, heteroaryl and aryl are optionally substituted by one to three hydroxy, oxo, $C_{1-3}$ alkyl, $C_{1-3}$ alkoxy, $C_{1-5}$ alkoxycarbonyl, NR₅R₆ or NR₅R₆—C(O)—;
wherein each Y is optionally further covalently attached to phenyl$C_{0-4}$ alkyl,
each R₅ and R₆ are independently hydrogen, phenyl$C_{0-3}$alkyl optionally subtituted by halogen, $C_{1-3}$ alkyl or di$C_{1-5}$ alkyl amino, $C_{1-2}$ acyl, benzoyl or $C_{1-4}$ branched or unbranched alkyl optionally substituted by $C_{1-4}$ alkoxy, hydroxy or mono or di$C_{1-3}$ alkyl amino;
m is 2;
and
X is O.

14. The compound according to claim 13 wherein:
G is phenyl or naphthyl wherein G is substituted by one R₃ and further substituted by one to three R₁ or R₂;
L' is
a bond, $C_{1-5}$ alkyl, hydroxy $C_{1-5}$ alkyl, $C_{2-4}$ alkenyl or amido$C_{1-5}$ alkyl.

15. The compound according to claim 14 wherein
L is:
—O—, >C(O), —OCH₂—, —CH₂—, —OCH₂CH₂—, —OCH₂CH₂CH₂—, —OCH₂CH₂(CH₃)—, —OCH₂(CH₃)CH₂—, —NH—, —NHCH₂—, —NHCH₂CH₂—, —S(O)ₘ—, —S(O)ₘCH₂—, —S(O)ₘCH₂CH₂—, —S(O)ₘCH₂CH₂CH₂—, —CH₂CH₂—, —CH₂CH₂CH₂— or —OCH₂C(O)—;
each R₁ is independently:
$C_{3-5}$ branched or unbranched alkyl optionally partially or fully halogenated and optionally substituted with phenyl or R₁ is N-morpholinyl;
cyclopropyl, cyclopentanyl or bicyclopentanyl optionally substituted with one to three methyl groups optionally be partially or fully halogenated, cyano, hydroxymethyl or phenyl;
substituted by methyl;

Q is
pyrimidinyl optionally substituted by one $C_{1-3}$ alkyl or phenyl;
Y is
a bond, —O—, —S—, >C(O), —NH—, —C(O)—NH—, —CH($C_{1-2}$ alkyl)-;
or Y is $C_{1-2}$ alkyl, $C_{1-2}$ alkyl(OH), $C_{2-4}$ alkenyl, $C_{1-2}$ acyl, imidazolyl, pyrazolyl, thienyl, pyrrolidinyl, pyrrolyl, indolyl, isoxazolyl, thiazolyl, oxazolyl, isothiazolyl or phenyl each optionally substituted by one to two hydroxy, oxo, $C_{1-3}$ alkyl, $C_{1-3}$ alkoxy, $C_{1-5}$ alkoxycarbonyl, NR₅R₆ or NR₅R₆—C(O)—;
wherein each Y is optionally further covalently attached to phenyl$C_{0-4}$ alkyl;
each R₅ and R₆ are independently hydrogen, phenyl$C_{0-3}$ alkyl optionally subtituted by halogen or $C_{1-3}$ alkyl, acetyl, benzoyl or $C_{1-4}$ branched or unbranched alkyl optionally substituted by $C_{1-3}$ alkoxy, hydroxy, mono or di$C_{1-3}$ alkyl amino.

16. The compound according to claim 2 wherein:
n is 0 or 1;
ring A and the phenyl ring to which it is fused form:

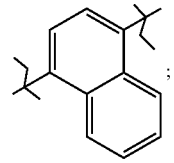

L is
>CRₓRᵧ wherein
Rₓ and Rᵧ are each independently hydrogen, heterocycle$C_{0-4}$ alkyl wherein the heterocyclic moiety is chosen from piperidinyl, morpholinyl and piperazinyl, imidazolyl$C_{0-4}$ alkyl or phenyl$C_{0-4}$ alkyl;
G is
phenyl or naphthyl wherein G is substituted by one R₃ and further substituted by one or more R₁ or R₂;
Q is:
pyrimidinyl;
R₁ is independently:
$C_{3-5}$ branched or unbranched alkyl optionally partially or fully halogenated, and optionally substituted with one to three $C_{3-6}$ cycloalkyl, hydroxy and phenyl;
N-morpholinyl;
cyclopropyl, cyclobutyl, cyclopentanyl, cyclohexanyl, bicyclopentanyl or bicyclohexanyl optionally partially or fully halogenated and optionally substituted with one to three $C_{1-3}$ alkyl groups optionally partially or fully halogenated, cyano, hydroxy$C_{1-3}$ alkyl or phenyl;
R₂ is independently:
a $C_{1-6}$ branched or unbranched alkyl optionally partially or fully halogenated or $C_{1-4}$ branched or unbranched alkoxy optionally partially or fully halogenated;
R₃ is
(J)₀₋₁—L'—S(O)ₘ—NH— or (J)₀₋₁—L'—O—C(O)—NH—,
wherein for R₃:
L' is
a bond, $C_{1-5}$ alkyl, hydroxy $C_{1-5}$ alkyl, $C_{2-4}$ alkenyl, amido$C_{1-5}$ alkyl;
J is:
cyclopropyl, cyclobutyl, cyclopentyl, cyclohexyl, cycloheptyl, bicyclopentanyl, bicyclohexanyl or bicycloheptanyl, phenyl, naphthyl, morpholinyl, piperidinyl, piperazinyl, pyridinyl, pyrimidinyl, pyrazinyl, pyridazinyl, pyrrolyl, pyrrolidinyl, imidazolyl, pyrazolyl, thiazolyl, oxazolyl, thienyl, furyl, dioxolanyl, tetrahydrofuryl, isoxazolyl and isothiazolyl,
cyclobutenyl, cyclopentenyl, cyclohexenyl, cyclohexadienyl, cycloheptenyl, cycloheptadienyl, bicyclohexenyl or bicycloheptenyl;
each of the above J is optionally substituted by one to two $R_4$;
  $R_4$ is oxo or mono- or di-$C_{1-3}$ alkylamino;
  Y is
a bond or >C(O),
further covalently attached to $NR_5R_6$, $C_{1-3}$ alkyl, $C_{3-6}$ cycloalkyl$C_{0-2}$alkyl, hydroxy, $C_{1-3}$ alkoxy, phenoxy, phenyl$C_{0-4}$ alkyl, piperazinyl$C_{0-4}$ alkyl, piperidinyl $C_{0-4}$alkyl, pyrrolidinyl$C_{0-4}$ alkyl, morpholinyl$C_{0-4}$ alkyl, tetrahydrofuranyl$C_{0-4}$ alkyl or pyridinyl $C_{0-4}$alkyl, each abovelisted heterocycle, heteroaryl and phenyl are optionally substituted by one to three hydroxy, oxo, $C_{1-4}$ alkyl, $C_{1-3}$ alkoxy, $C_{1-5}$ alkoxycarbonyl, $NR_5R_6$—C(O)— or $C_{1-4}$ acyl,
  each $R_5$ and $R_6$ are independently hydrogen, phenyl$C_{0-3}$ alkyl optionally subtituted by halogen, $C_{1-3}$ alkyl or di$C_{1-5}$ alkyl amino, $C_{1-2}$ acyl, benzoyl or $C_{1-4}$ branched or unbranched alkyl optionally substituted by $C_{1-4}$ alkoxy, hydroxy or mono or di$C_{1-3}$ alkyl amino;
m is 2;
and
X is O.

17. The compound according to claim 16 G is phenyl or naphthyl wherein G is substituted by one $R_3$ and further substituted by one to three $R_1$ or $R_2$;
and
  L' is a bond, $C_{1-5}$ alkyl, hydroxy $C_{1-5}$ alkyl, $C_{2-4}$ alkenyl or amido$C_{1-5}$ alkyl.

18. The compound according to claim 17 wherein:
L is:
>$CR_xR_y$ wherein
one of $R_x$ and $R_y$ is hydrogen and the other is heterocycle wherein the heterocyclic moiety is chosen from piperidinyl, morpholinyl and piperazinyl, imidazolyl or benzyl;
  each $R_1$ is independently:
$C_{3-5}$ branched or unbranched alkyl optionally partially or fully halogenated and optionally substituted with phenyl or $R_1$ is N-morpholinyl;
cyclopropyl, cyclopentanyl, cyclohexanyl or bicyclopentanyl optionally substituted with one to three methyl groups optionally be partially or fully halogenated, cyano, hydroxymethyl or phenyl;
cyclopentyloxy or cyclohexyloxy which are optionally partially or fully halogenated;
2-tetrahydrofuranyl substituted by methyl;
  Y is
a bond or >C(O),
further covently attached to $NR_5R_6$, piperazinyl$C_{1-2}$ alkyl, piperidinyl$C_{1-2}$ alkyl, pyrrolidinyl$C_{1-2}$ alkyl, morpholinyl$C_{1-2}$ alkyl, tetrahydrofuranyl$C_{1-2}$ alkyl or pyridinyl$C_{1-2}$ alkyl;
each $R_5$ and $R_6$ are independently hydrogen or $C_{1-4}$branched or unbranched alkyl optionally substituted by $C_{1-3}$ alkoxy, hydroxy, mono or di$C_{1-3}$ alkyl amino.

19. A compound selected from the group consisting of:
  N-(5-tert-Butyl-3-{3-[4-(2-isopropyl-6-methyl-pyrimidin-4-yloxy)-naphthalen-1-yl]-ureido}-2-methoxy-phenyl)-methanesulfonamide;
  N-(5-tert-Butyl-3-{3-[4-(2,6-dimethyl-pyrimidin-4-yloxy)-naphthalen-1-yl]-ureido}-2-methoxy-phenyl)-methanesulfonamide;
  N-(5-tert-Butyl-2-methoxy-3-{3-[4-(pyrimidin-4-yloxy)-naphthalen-1-yl]-ureido}-phenyl)-methanesulfonamide;
  (5-tert-Butyl-2-methoxy-3-{3-[4-(pyrimidin-4-yloxy)-naphthalen-1-yl]-ureido}-phenyl)-carbamic acid methyl ester;
  N-(5-tert-Butyl-2methoxy-3-{3-[4-(2-methoxy-6-methyl-pyrimidin-4-yloxy)-naphthalen-1-yl]-ureido}-phenyl)-methanesulfonamide;
  N-(5-tert-Butyl-3-{3-[4-(2-isopropoxy-6-methyl-pyrimidin-4-yloxy)-naphthalen-1-yl]-ureido}-2-methoxy-phenyl)-methanesulfonamide;
  N-(5-tert-Butyl-3-{3-[4-(2-methanesulfinyl-pyrimidin-4-yloxy)-naphthalen-1-yl]-ureido}-2-methoxy-phenyl)-methanesulfonamide;
  N-(5-tert-Butyl-3-{3-[4-(2-methanesulfonyl-pyrimidin-4-yloxy)-naphthalen-1-yl]-ureido}-2-methoxy-phenyl)-methanesulfonamide;
  N-(3-{3-[4-(2-Amino-pyrimidin-4yloxy)-naphthalen-1-yl]-ureido}-5-tert-butyl-2-methoxy-phenyl)-methanesulfonamide;
  N-[5-tert-Butyl-3-(3-{4-[2-(cyclopropylmethyl-amino)-pyrimidin-4-yloxy]-naphthalen-1-yl}-ureido)-2-methoxy-phenyl]-methanesulfonamide;
  N-(3-{3-[4-(2-Benzylamino-pyrimidin-4-yloxy)-naphthalen-1-yl]-ureido}-5-tert-butyl-2-methoxy-phenyl)-methanesulfonamide;
  N-[5-tert-Butyl-2-methoxy-3-(3-{4-[2-(1-(R)-phenyl-ethylamino)-pyrimidin-4-yloxy]-naphthalen-1-yl}-ureido)-phenyl]-methanessulfonamide;
  N-[5-tert-Butyl-2-methoxy-3-(3-{4-[2-(1-(S)-phenyl-ethylamino)-pyrimidin-4-yloxy]-naphthalen-1-yl}-ureido)-phenyl]-methanesulfonamide;
  N-(5-tert-Butyl-3-{3-[4-(2-isobutylamino-pyrimidin-4-yloxy)-naphthalen-1-yl]-ureido}-2-methoxy-phenyl)-methanesulfonamide;
  N-(5-tert-Butyl-2-methoxy-3-{3-[4-(2-methylamino-pyrimidin-4-yloxy)naphthalen-1-yl]-ureido}-phenyl)-methanesulfonamide
  N-(5-tert-Butyl-3-{3-[4-(2-ethylamino-pyrimidin-4-yloxy)-naphthalen-1-yl]-ureido}-2-methoxy-phenyl)-methanesulfonamide;
  N-(5-tert-Butyl-3-{3-[4-(2-isopropylamino-pyrimidin-4-yloxy)-naphthalen-1-yl]-ureido}-2-methoxy-phenyl)-methanesulfonamide;
  N-(5-tert-Butyl-2-methoxy-3-{3-[4-(2-propylamino-pyrimidin-4-yloxy)-naphthalen-1-yl]-ureido}-phenyl)-methanesulfonamide
  N-[5-tert-Butyl-3-(3-{4-[2-(cyclopentylmethyl-amino)-pyrimidin-4-yloxy]-naphthalen-1-ureido)-2-methoxy-phenyl]-methanesulfonamide;
  N-{5-tert-Butyl-2-methoxy-3-[3-(4-{2[(thiophen-2-ylmethyl)-amino]-pyrimidin-4-yloxy}-naphthalen-1-yl)-ureido]-phenyl}-methanesulfonamide;
  N-{5-tert-Butyl-3-[3-(4-{2-[(furan-2-ylmethyl)-amino]-pyrimidin-4-yloxy}-naphthalen-1-yl)-ureido]-2-methoxy-phenyl}-methanesulfonamide;
  N-{5-tert-Butyl-2-methoxy-3-[3-(4-{2-[(tetrahydro-furan-2-ylmethyl)-amino]-pyrimidin-4-yloxy}-naphthalen-1-yl)-ureido]-phenyl}-methanesulfonamide;
  N-(5-tert-Butyl-3-{3-[4-(2-butylamino-pyrimidin-4-yloxy)-naphthalen-1-yl]-ureido}-2-methoxy-phenyl)-methanesulfonamide;

N-(5-tert-Butyl-2-methoxy-3-{3-[4-(2-phenethylamino-pyrimidin-4-yloxy)-naphthalen-1-yl]-ureido}-phenyl)-methanesulfonamide;

N-{5-tert-Butyl-2-methoxy-3-[3-(4-{2-[pyridin-2-ylmethyl)-amino]-pyrimidin-4-yloxy}-naphthalen-1-yl)-ureido]-phenyl}-methanesulfonamide;

N-{5-tert-Butyl-2-methoxy-3-[3-(4-{2-[(pyridin-3-ylmethyl)-amino]-pyrimidin-4-yloxy}-naphthalen-1-yl)-ureido]-phenyl}-methanesulfonamide;

N-(5-tert-Butyl-3-{3-[4-(2-cyclopentylamino-pyrimidin-4-yloxy)-naphthalen-1-yl]-ureido}-2-methoxy-phenyl)-methanesulfonamide;

N-(5-tert-Butyl-3-{3-[4-(2-cyclohexylamino-pyrimidin-4-yloxy)-naphthalen-1-yl]-ureido}-2-methoxy-phenyl)-methanesulfonamide;

N-(5-tert-Butyl-2-methoxy-3-{3-[4-(2-morpholin-4-yl-pyrimidin-4-yloxy)-naphthalen-1-yl]-ureido}-phenyl)-methanesulfonamide;

N-(5-tert-Butyl-3-{3-[4-(2-dimethylamino-pyrimidin-4-yloxy)-naphthalen-1-yl]-ureido}-2methoxy-phenyl)-methanesulfonamide;

N-[3-(3-{4-[2-(Benzyl-methyl-amino)-pyrimidin-4-yloxy]-naphthalen-1-yl}-ureido-5-tert-butyl-2-methoxy-phenyl]-methanesulfonamide N-{5-tert-Butyl-2-methoxy-3-[3-(4-{2-[(pyridin-4-ylmethyl)-amino]-pyrimidin-4-yloxy}-naphthalen-1-yl)-ureido]-phenyl}-methanesulfonamide N-(5-tert-Butyl-3-{3-[4-(2-diethylamino-pyrimidin-4-yloxy)-naphthalen-1-yl]-ureido}-2-methoxy-phenyl)-methanesulfonamide;

N-(5-tert-Butyl-2-methoxy-3-{3-[4-(2-phenylamino-pyrimidin-4-yloxy)-naphthalen-1-yl]-ureido}-phenyl)-methanesulfonamide;

N-(5-tert-Butyl-2-methoxy-3-{3-[4-(2-pyrrolidin-1-yl-pyrimidin-4-yloxy)-naphthalen-1-yl]-ureido}-phenyl)-methanesulfonamide;

(3-{3-[4-(2-Benzylamino-Pyrimidin-4-yloxy)-naphthalen-1-yl]-ureido}-5-tert-butyl-2-methoxy-phenyl)-carbamic acid methyl ester;

[5-tert-Butyl-2-methoxy-3-(3-{4-[2-(1-(R)-phenyl-ethylamino)-pyrimidin-4-yloxy]-naphthalen-1-yl}-ureido)-phenyl]-carbamic acid methyl ester;

[5-tert-Butyl-2-methoxy-3-(3-{4-[2-(1-(S)-phenyl-ethylamino)-Pyrimidin-4yloxy]-naphthalen-1-yl}-ureido)-phenyl]-carbamic acid methyl ester;

[5-tert-Butyl-3-(3-{4-[2-(cyclopropylmethyl-amino)-pyrimidin-4-yloxy]-naphthalen-1-yl}-ureido)-2-methoxy-phenyl]-carbamic acid methyl ester;

{5-tert-Butyl-2-methoxy-3-[3-(4-{2-[(tetrahydro-furan-2-ylmethyl)-amino]-pyrimidin-4-yloxy-}-naphthalen-1-yl)-ureido]-phenyl}-carbamic acid methyl ester;

(3-{3-[4-(2-Amino-pyrimidin-4-yloxy)-naphthalen-1-yl]-ureido}-5-tert-butyl-2-methoxy-phenyl)-carbamic acid methyl ester;

1-[4-(2-Amino-pyrimidin-4-yloxy)-naphthalen-1-yl]-3-[5-tert-butyl-3-(4,5-dihydro-oxazol-2-ylamino)-2-methoxy-phenyl]-urea;

1-[5-tert-Butyl-3-(4,5-dihydro-oxazol-2-ylamino)-2-methoxy-phenyl]-3-{4-[2-(1-phenyl-ethylamino)-pyrimidin-4-yloxy]-naphthalen-1-yl}-urea;

N-[5-tert-Butyl-2-methoxy-3-(3-{4-[2-(2-methoxy-ethylamino)-6-methyl-pyrimidin-4-yloxy]-naphthalen-1-yl}-ureido)-phenyl]-methanesulfonamide;

N-[5-tert-Butyl-3-(3-{4-[2-(2-dimethylamino-ethylamino)-6-methyl-pyrimidin-4-yloxy]-naphthalen-1-yl}-ureido)-2-methoxy-phenyl]-methanesulfonamide;

N-[5-tert-Butyl-2-methoxy-3-(3-{4-[6-methyl-2-(2-pyrrolidin-1-yl-ethylamino)-pyrimidin-4-yloxy]-naphthalen-1-yl}-ureido)-phenyl]-methanesulfonamide;

N-[5-tert-Butyl-2-methoxy-3-(3-{4-[6-methyl-2-(2-morpholin-4-yl-ethylamino)-pyrimidin-4-yloxy]-naphthalen-1-yl}-ureido)-phenyl]-methanesulfonamide;

N-(5-tert-Butyl-2-methoxy-3-{3-[4-(6-methyl-2-pyrrolidin-1-yl-pyrimidin-4-yloxy)-naphthalen-1-yl]-ureido}-phenyl)-methanesulfonamide;

N-[5-tert-Butyl-3-(3-{4-[2-(2-dimethylamino-ethoxy)-6-methyl-pyrimidin-4-yloxy]-naphthalen-1-yl}-ureido)-2-methoxy-phenyl]-methanesulfonamide;

N-(5-tert-Butyl-2-methoxy-3-{3-[4-(2-phenoxy-pyrimidin-4-yloxy)-naphthalen-1-yl]-ureido}-phenyl)-methanesulfonamide;

N-(5-tert-Butyl-3-{3-[4-(2-isopropylamino-6-methyl-pyrimidin-4-yloxy)-naphthalen-1-yl]-ureido}-2-methoxy-phenyl)-methanesulfonamide;

N-(5-tert-Butyl-3-{3-[4-(2-methanesulfonylamino-6-methyl-pyrimidin-4-yloxy)-naphthalen-1-yl]-ureido}-2-methoxy-phenyl)-methanesulfonamide;

N-(5-tert-Butyl-3-{3-[4-(2-isobutylamino-6-methyl-pyrimidin-4-yloxy)-naphthalen-1-yl]-ureido}-2-methoxy-phenyl)-methanesulfonamide;

N-{5-tert-Butyl-2-methoxy-3-[3-(4-{6-methyl-2-[(tetrahydro-furan-2-ylmethyl)-amino]-pyrimidin-4-yloxy}-naphthalen-1-yl)-ureido]-phenyl}methanesulfonamide, and N-(5-tert-Butyl-2-methoxy-3-{3-[4-(6-methyl-2-methylamino-pyrimidin-4-yloxy)-naphthalen-1-yl]-ureido}-phenyl)-methanesulfonamide;

or the pharmaceutically acceptable derivatives thereof.

20. A pharmaceutical composition comprising a pharmaceutically effective amount of a compound according to claim 1.

21. A method of treating a disease or condition selected from rheumatoid arthritis, osteoarthritis, Crohn's disease, ulcerative colitis, multiple sclerosis, Guillain-Barre syndrome, psoriasis, graft versus host disease, systemic lupus erythematosus, diabetes, toxic shock syndrome, acute and chronic pain, contact dermatitis, atherosclerosis, traumatic arthritis, glomerulonephritis, reperfusion injury, sepsis, bone resorption diseases, chronic obstructive pulmonary disease, congestive heart failure, asthma, myocardial infarction, thermal injury, adult respiratory distress syndrome (ARDS), dermatoses with acute inflammatory components, acute purulent meningitis, necrotizing entrerocolitis and syndromes associated with hemodialysis, leukopherisis and granulocyte transfusion comprising administering to a patient in need of such treatment a therapeutically effective amount of a compound according to claim 1.

22. The method according to claim 21 wherein the disease is selected from rheumatoid arthritis, osteoarthritis, Crohn's disease, psoriasis, ulcerative colitis, osteoporosis, chronic obstructive pulmonary disease and congestive heart failure.

23. The method according to claim 22 wherein the disease is selected from rheumatoid arthritis, Crohn's disease, psoriasis, chronic obstructive pulmonary disease and congestive heart failure.

24. A method of making a compound of the formula(I):

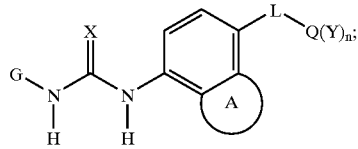
(I)

wherein X is O and G, Ar, L, Q, n and Y are as defined in claim 1, said method comprising:

a) reacting an arylamine with phenyl chloroformate in a suitable solvent with a suitable base at 0–85° C. for 2–24 hours:

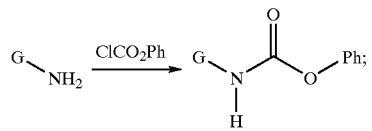

b) reacting the product of step a) with an arylamine shown below in a non-protic anhydrous at 0–110° C., for 2–24 hours, to produce a compound of the formula (I):

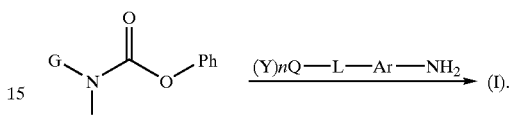

* * * * *

UNITED STATES PATENT AND TRADEMARK OFFICE
CERTIFICATE OF CORRECTION

PATENT NO. : 6,765,009 B2
DATED : July 20, 2004
INVENTOR(S) : Pier Francesco et al.

It is certified that error appears in the above-identified patent and that said Letters Patent is hereby corrected as shown below:

<u>Title page,</u>
Item [75], Inventors, the correct name should be listed as -- Pier Francesco Cirillo --

Signed and Sealed this

Sixteenth Day of November, 2004

JON W. DUDAS
*Director of the United States Patent and Trademark Office*